United States Patent
Mills et al.

(10) Patent No.: US 8,361,756 B2
(45) Date of Patent: Jan. 29, 2013

(54) BIFIDOBACTERIAL GENE SEQUENCES AND THEIR USE

(75) Inventors: David A. Mills, Davis, CA (US); Carlito B. Lebrilla, Davis, CA (US); J. Bruce German, Davis, CA (US); David Sela, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 619 days.

(21) Appl. No.: 12/441,272

(22) PCT Filed: Sep. 14, 2007

(86) PCT No.: PCT/US2007/020032
§ 371 (c)(1),
(2), (4) Date: Dec. 4, 2009

(87) PCT Pub. No.: WO2008/033520
PCT Pub. Date: Mar. 20, 2008

(65) Prior Publication Data
US 2010/0113383 A1    May 6, 2010

Related U.S. Application Data

(60) Provisional application No. 60/845,130, filed on Sep. 15, 2006.

(51) Int. Cl.
C12P 19/04 (2006.01)
C12N 9/24 (2006.01)
C07H 21/02 (2006.01)

(52) U.S. Cl. .................... 435/101; 435/200; 536/23.2

(58) Field of Classification Search ................ None
See application file for complete search history.

(56) References Cited

U.S. PATENT DOCUMENTS

| | | | |
|---|---|---|---|
| 6,555,348 B2 | 4/2003 | Jørgensen et al. | |
| 7,081,355 B2 | 7/2006 | Jørgensen et al. | |
| 2002/0086358 A1 | 7/2002 | Jørgensen et al. | |
| 2005/0089956 A1 | 4/2005 | Endo et al. | |
| 2005/0175759 A1 | 8/2005 | Singhal | |
| 2006/0057247 A1 | 3/2006 | Nguyen et al. | |

OTHER PUBLICATIONS

Supplementary Partial European Search Report from EP 07838265 dated Apr. 7, 2010 (8 pages).
Communication under Rule 71(3) from EP 07838265 dated Nov. 12, 2010, Intention to Grant European Patent (4 pages).
Bode, Lars; "Recent advances on structure, metabolism, and function of human milk oligosaccharides"; *J. Nutr.*; 136(8):2127-2130 (Aug. 2006).
Boehm at al.; "Prebiotic concept for infant nutrition"; *Acta Paediatr Suppl.*; 441:64-67 (Sep. 2003).
Coppa et al.; "The first prebiotics in humans Human milk oligosaccharides"; *J. Clin. Gastroentrol.*; 38(Suppl. 2):S80-S83 (Jul. 2004).
Database UniProt; Database Accession No. Q9K6M7; *Beta-galactosidase*, Oct. 2000 (1 page).
Hung et al.; "Molecular and Biochemical Analysis of Two b-Galactosidases from *Bifidobacterium infantis* HL96"; *Appl. Environ. Microbiol.*; 67(9):4256-42636 (2001).
Katayama et al.; "Novel Bifidobacterial glycosidases acting on sugar chains of mucin glycoproteins"; *J. Biosci. Bioeng.*; 99(5):457-465 (May 2005).
Kitaoka Motomitsu et al: "Novel putative galactose operon involving lacto-N-biose phosphorylase in *Bifidobacterium longum*"; *Appl. Environ. Microbiol.*; 71(6):3158-3162 (Jun. 2005).
Matsuo et al.; "ICloning and overexpression of β-N-acetylglucosaminidase encoding gene *nagA* from *Aspergillus oryzae* and enzyme-catalyzed synthesis of human milk oligosaccharide"; *Biosci. Biotechnol. Biochem.*; 67(3):646-650 (Mar. 2003).
Priem et al.; "A new fermentation process allows large-scale production of human milk oligosaccharides by metabolically engineered bacteria"; *Glycobiology*; 12(4):235-240 (Apr. 2002).
Vos et al.; "A specific prebiotic oligosaccharide mixture stimulates delayed-type hypersensitivity in a murine influenza vaccination model"; *International Immunopharmacology*; 6(8): 1277-1286 (Aug. 2006).
Ward et al.; "In vitro fermentation of breast milk oligosaccharides by *Bifidobacterium infantis* and *Lactobacillus gasseri*"; *Appl. Environ. Microbiol.*; 72(6): 4497-4499 (Jun. 2006).
Katayama, T., et al.; "Molecular Cloning and Characterization of *Bifidobacterium bifidum* 1,2-α-L-Fucosidase (AfcA), a Novel Inverting Glycosidase (Glycoside Hydrolase Family 95)" *Journal of Bacteriology*; 186(15):4885-93 (2004).
Sakurada, K., et al.; "Cloning, Expression, and Characerization of the *Micromonospora viridifaciens* Neuraminidase Gene in *Streptomyces lividans*" *Journal of Bacteriology*; 174(21):6896-6903 (1992).

*Primary Examiner* — Tekchand Saidha
*Assistant Examiner* — Md. Younus Meah
(74) *Attorney, Agent, or Firm* — Kilpatrick Townsend & Stockton LLP

(57) ABSTRACT

This invention provides nucleic acids and proteins involved in oligosaccharide modification in the species *Bifidobacteria*. The invention provides methods for utilizing the proteins of the invention to generate human milk oligosaccharides or oligosaccharide mimics. The invention also provides compositions containing the human milk oligosaccharides or oligosaccharide mimics and methods for use.

13 Claims, 91 Drawing Sheets

Fig. 1 (sheet 1)

Sialidase I (EC:3.2.1.18 COG4409) Contig23 Gene 826

| Name | Evalue | Percent identity |
|---|---|---|
| Sialidase or Neuraminidase, Large 68 kd Form gi|1942644|pdb|1EUT| Sialidase, Large 68 kd Form, Complexed with Galactose | 5e-97 | 55 |

Refresh BLAST results

Best Blast vs SwissProt/TREMBL Hit

| Name | Evalue | Percent identity |
|---|---|---|
| Q02834 Sialidase precursor (EC:3.2.1.18) (Neuraminidase). Micromonospora viridifaciens. | 5e-97 | 55 |

PFam Model Comparison

| Model | Description | Evalue | Score |
|---|---|---|---|
| BNR | BNR/Asp-box repeat | 5.8e-15 | 60.3 |

Refresh PFAM results

TIGRfam Model Comparison

No TIGRfam model hits

Fig. 1 (sheet 2)

COGS Comparison

| Group | COG ID | COG Name | Top Hit | Score | Evalue |
|---|---|---|---|---|---|
| G | COG4409 | Neuraminidase (sialidase) | NanH | 139 | 5e-34 |

All genes with COG4409

Best KEGG Hit

| Name | Evalue | Percent Identity |
|---|---|---|
| nanH, secreted sialidase [EC:3.2.1.18] [KO:K01186] | 1e-89 | 51 |

PRIAM EC Number Assignment and Map

| Evalue | EC Number |
|---|---|
| 6e-43 | 3.2.1.18 |

| Pathway(s) | Map Number |
|---|---|
| Exo-alpha-sialidase. | map00511 |
| Exo-alpha-sialidase. | map00600 |
| Exo-alpha-sialidase. | map01032 |

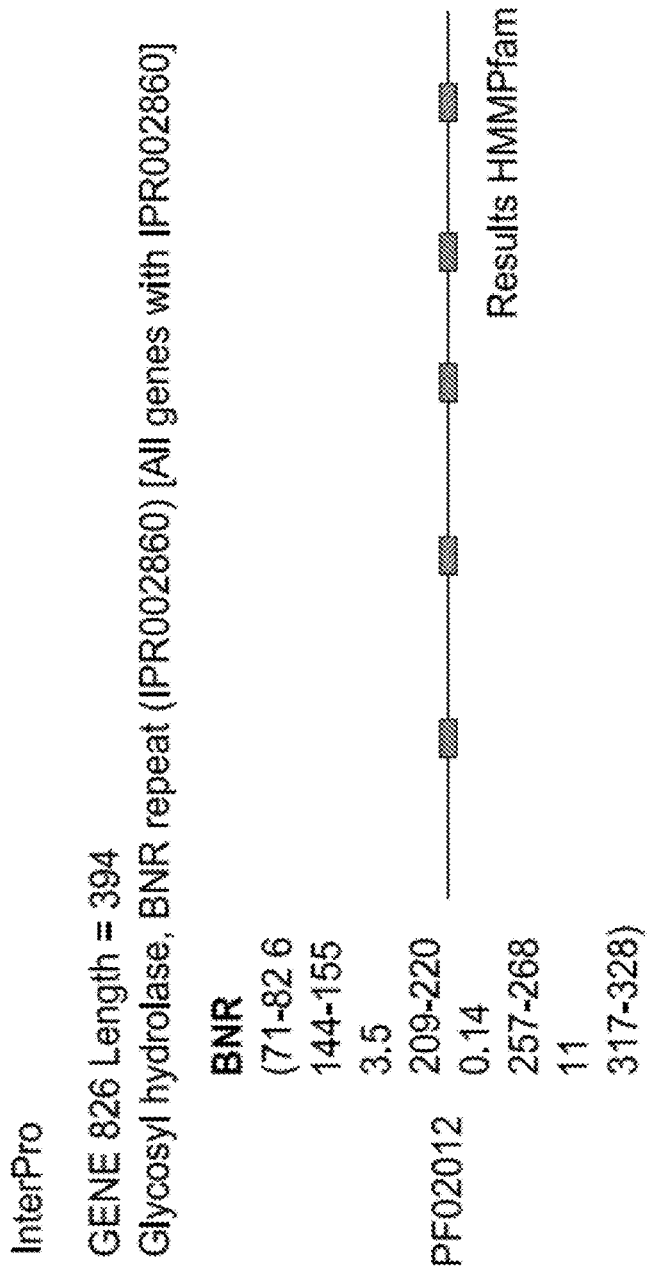
Fig. 1 (sheet 3)

Fig. 2 (sheet 1)

Sialidase II (EC:3.2.1.18 COG4409) Contig30 Gene 1562

Best Blast vs NR Hit

| Name | Evalue | Percent Identity |
|---|---|---|
| sialidase A precursor [Propionibacterium acnes KPA171202] gi\|50839774\|gb\|AAT82441.1\| sialidase A precursor [Propionibacterium acnes KPA171202] Refresh BLAST results | 1e-170 | 44 |

Best Blast vs SwissProt/TREMBL Hit

| Name | Evalue | Percent Identity |
|---|---|---|
| Q6A9X5 Sialidase A (EC:3.2.1.18) Propionibacterium acnes. | 1e-170 | 44 |

PFam Model Comparison

| Model | Description | Evalue | Score |
|---|---|---|---|
| BNR | BNR/Asp-box repeat | 7.9e-13 | 53.2 |

Refresh PFAM results

Fig. 2 (sheet 2)

TIGRfam Model Comparison

No TIGRfam model hits

COGS Comparison

| Group | COG ID | COG Name | Top Hit | Score | Evalue |
|---|---|---|---|---|---|
| G | COG4409 | Neuramindase (sialidase) | NanH | 71.2 | 2e-13 |

All genes with COG4409

Best KEGG Hit

| Name | Evalue | Percent Identity |
|---|---|---|
| sialidase A precursor [EC:3.2.1.18] [KO:K01186] | 1e-170 | 44 |

PRIAM EC Number Assignment and Map

| Evalue | EC Number |
|---|---|
| 1e-24 | 4.2.2.15 |

| Pathway(s) | Map Number |
|---|---|
| | None |

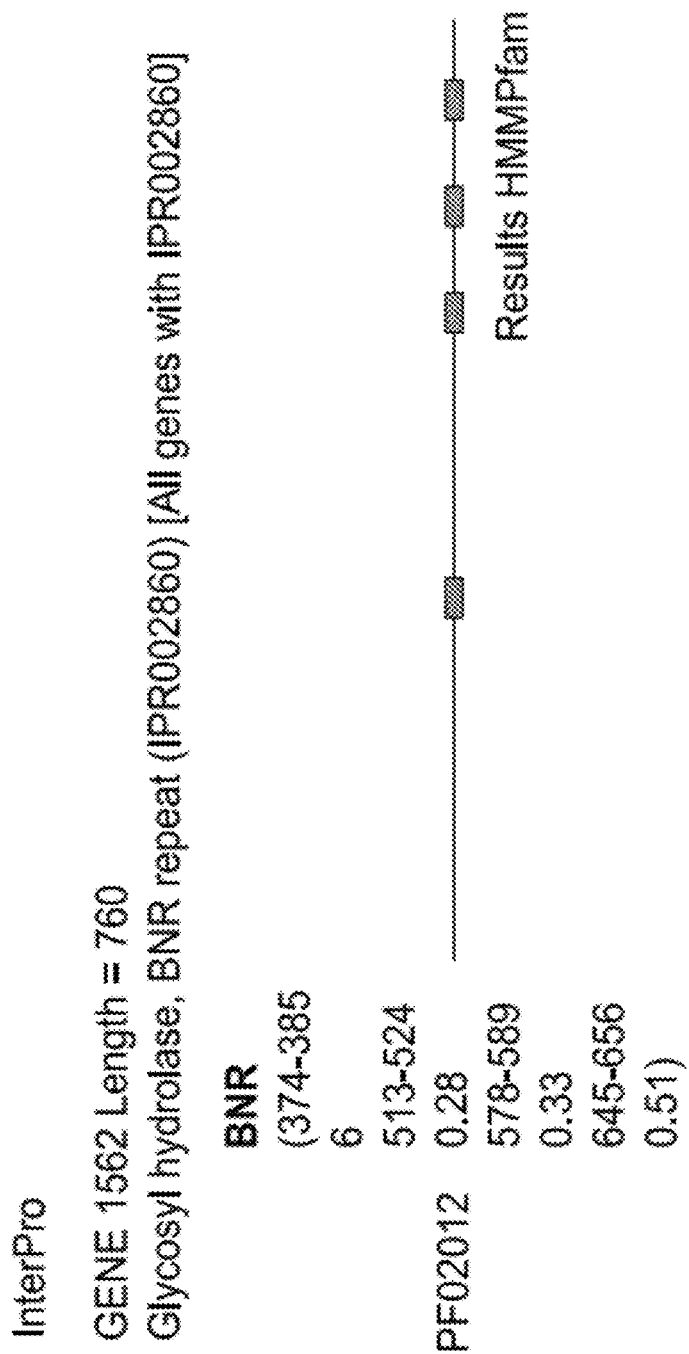
Fig. 2 (sheet 3)

Fig. 3 (sheet 1)

Alpha-L-fucosidase I (EC:3.2.1.51 COG3669) Contig22 Gene 815

Best Blast vs NR Hit

| Name | Evalue | Percent Identity |
|---|---|---|
| alpha-1,3/4-fucosidase, putative [Porphyromonas gingivalis W83] gi|34541374|ref|NP_905853.1| alpha-1,3/4-fucosidase, putative [Porphyromonas gingivalis W83] | 1e-111 | 46 |

Refresh BLAST results

Best Blast vs SwissProt/TREMBL Hit

| Name | Evalue | Percent Identity |
|---|---|---|
| Q7MU22 Alpha-1,3/4-fucosidase, putative. Porphyromonas gingivalis (Bacteroides gingivalis). | 1e-111 | 46 |

PFam Model Comparison

No Pfam model hits
Refresh PFAM results

*Fig. 3 (sheet 2)*

TIGRfam Model Comparison

No TIGRfam model hits

COGS Comparison

| Group | COG ID | COG Name | Top Hit | Score | Evalue |
|---|---|---|---|---|---|
| G | COG3669 | Alpha-L-fucosidase | COG3669 | 207 | 2e-54 |

All genes with COG3669

Best KEGG Hit

| Name | Evalue | Percent Identity |
|---|---|---|
| alpha-1,3/4-fucosidase, putative [EC:3.2.1.51] [KO:K01206] | 1e-111 | 46 |

PRIAM EC Number Assignment and Map

No EC Pathway hits

InterPro

No InterPro hits

Fig. 4 (sheet 1)

Alpha-L-fucosidase II (EC:3.2.1.51 COG3669) Contig25 Gene 1206

Best Blast vs NR Hit

| Name | Evalue | Percent identity |
|---|---|---|
| alpha-L-fucosidase, putative [Thermotoga maritima MSB8] gi¦4980806¦gb¦AAD 35394.1¦alpha-L-fucosidase, putative [Thermotoga maritima MSB8] gi¦42543189¦pdb¦1ODU¦B Chain B, Crystal structure of Thermotoga maritima A-TRUNCATED Refresh BLAST results | 6e-84 | 47 |

Best Blast vs SwissProt/TREMBL Hit

| Name | Evalue | Percent identity |
|---|---|---|
| Q9WYE2 Alpha-L-fucosidase, putative. Thermotoga maritima. | 6e-84 | 47 |

PFam Model Comparison

| Model | Description | Evalue | Score |
|---|---|---|---|
| Alpha_L_fucos | Alpha-L-fucosidase | 2.6e-26 | 98.0 |

Refresh PFAM results

Fig. 4 (sheet 2)

TIGRfam Model Comparison

No TIGRfam model hits

COGS Comparison

| Group | COG ID | COG Name | Top Hit | Score | Evalue |
|---|---|---|---|---|---|
| G | COG3669 | Alpha-L-fucosidase | COG3669 | 185 | 6e-48 |

All genes with COG3669

Best KEGG Hit

| Name | Evalue | Percent Identity |
|---|---|---|
| alpha-L-fucosidase, putative [EC:3.2.1.51] [KO:K01206] | 3e-84 | 47 |

PRIAM EC Number Assignment and Map

| Evalue | EC Number |
|---|---|
| 4e-43 | 3.2.1.51 |

| Pathway(s) | Map Number |
|---|---|
| Alpha-L-fucosidase. | map00511 |
| Alpha-L-fucosidase. | map01032 |

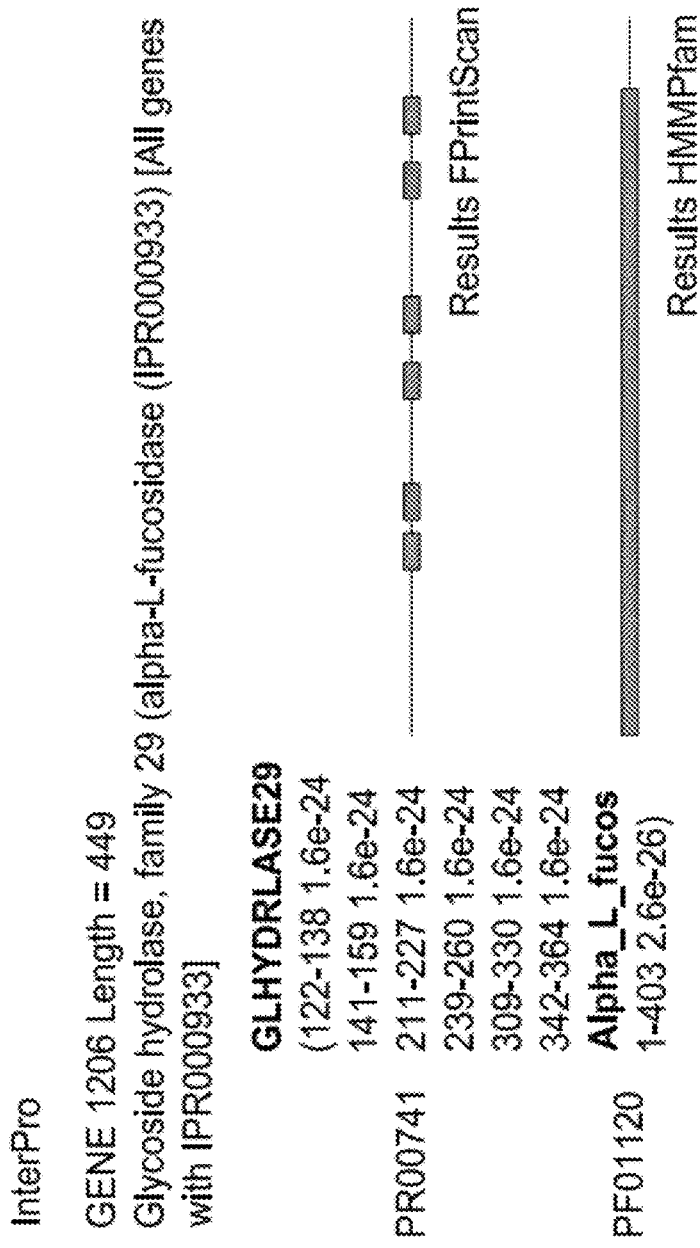
Fig. 4 (sheet 3)

Fig. 5 (sheet 1)

Alpha-L-fucosidase III (EC:3.2.1.51 COG3669) Contig29 Gene 1394

Best Blast vs NR Hit

| Name | Evalue | Percent Identity |
|---|---|---|
| alpha-L-fucosidase precursor [Propionibacterium acnes KPA171202] gi| 50841114|gb| AAT83781.1| alpha-L-fucosidase precursor [Propionibacterium acnes KPA171202] | 2e-27 | 43 |

Refresh BLAST results

Best Blast vs SwissProt/TREMBL Hit

| Name | Evalue | Percent Identity |
|---|---|---|
| Q6A632 Alpha-L-fucosidase (EC:3.2.1.51) Propionibacterium acnes. | 2e-27 | 43 |

Pfam Model Comparison

No Pfam model hits
Refresh PFAM results

Fig. 5 (sheet 2)

TIGRfam Model Comparison

No TIGRfam model hits

COGS Comparison

| Group | COG ID | COG Name | Top Hit | Score | Evalue |
|---|---|---|---|---|---|
| G | COG3669 | Alpha-L-fucosidase | COG3669 | 80.5 | 9e-17 |

All genes with COG3669

Best KEGG Hit

| Name | Evalue | Percent Identity |
|---|---|---|
| alpha-L-fucosidase precursor [EC:3.2.1.51] [KO:K01206] | 1e-27 | 43 |

PRIAM EC Number Assignment and Map

| Evalue | EC Number |
|---|---|
| 9e-14 | 3.2.1.51 |

| Pathway(s) | Map Number |
|---|---|
| Alpha-L-fucosidase. | map00511 |
| Alpha-L-fucosidase. | map01032 |

Fig. 5 (sheet 3)

Fig. 6 (sheet 1)

N-acetyl-beta-hexosaminidase I (EC:3.2.1.52 COG3525) Contig23 Gene 833

Best Blast vs NR Hit

| Name | Evalue | Percent Identity |
|---|---|---|
| possible beta-hexosaminidase A [Bifidobacterium longum NCC2705] gi\|23325247\|gb\|AAN23923.1\| possible beta-hexosaminidase A [Bifidobacterium longum NCC2705] | 1e-144 | 48 |

Refresh BLAST results

Best Blast vs SwissProt/TREMBL Hit

| Name | Evalue | Percent Identity |
|---|---|---|
| Q8G826 Possible beta-hexosaminidase A. Bifidobacterium longum. | 1e-144 | 48 |

PFam Model Comparison

| Model | Description | Evalue | Score |
|---|---|---|---|
| Glyco_hydro_20 | Glycosyl hydrolase family 20, catalytic | 5.3e-53 | 186.7 |

Refresh PFAM results

Fig. 6 (sheet 2)

TIGRfam Model Comparison

No TIGRfam model hits

COGS Comparison

| Group | COG ID | COG Name | Top Hit | Score | Evalue |
|---|---|---|---|---|---|
| G | COG3525 | N-acetyl-beta-hexosaminidase | Chb | 92.0 | 1e-19 |

All genes with COG3525

Best KEGG Hit

| Name | Evalue | Percent Identity |
|---|---|---|
| possible beta-hexosaminidase A | 1e-144 | 48 |

Fig. 6 (sheet 3)

PRIAM EC Number Assignment and Map

| Evalue | EC Number |
|---|---|
| 9e-17 | 3.2.1.52 |

| Pathway(s) | Map Number |
|---|---|
| Beta-N-acetylhexosaminidase. | map00511 |
| Beta-N-acetylhexosaminidase | map00530 |
| Beta-N-acetylhexosaminidase | map00531 |
| Beta-N-acetylhexosaminidase | map00603 |
| Beta-N-acetylhexosaminidase | map01032 |

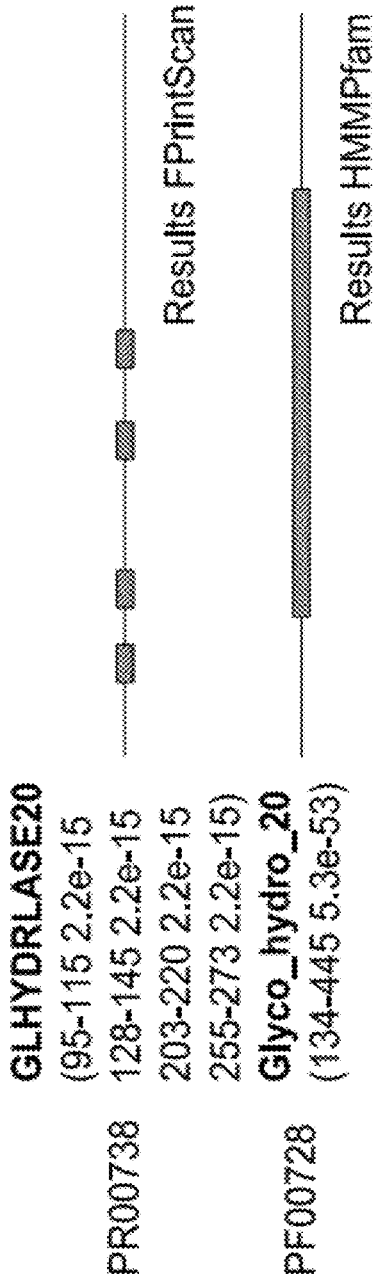
Fig. 6 (sheet 4)

Fig. 7 (sheet 1)

N-acetyl-beta-hexosaminidase II (EC:3.2.1.52 COG3525) Contig30 Gene 1414

Best Blast vs NR Hit

| Name | Evalue | Percent Identity |
|---|---|---|
| possible beta-hexosaminidase A [Bifidobacterium longum NCC2705] gi|23325247|gb|AAN23923.1| possible beta-hexosaminidase A [Bifidobacterium longum NCC2705] | 1e-141 | 45 |

Refresh BLAST results

Best Blast vs SwissProt/TREMBL Hit

| Name | Evalue | Percent Identity |
|---|---|---|
| Q8G826 Possible beta-hexosaminidase A [Bifidobacterium longum] | 1e-141 | 45 |

PFam Model Comparison

| Model | Description | Evalue | Score |
|---|---|---|---|
| Glyco_hydro_20 | Glycosyl hydrolase family 20, catalytic | 4.8e-41 | 146.9 |
| Glyco_hydro_20b | Glycosyl hydrolase family 20, domain | 0.00041 | 7.2 |

Refresh PFAM results

Fig. 7 (sheet 2)

TIGRfam Model Comparison

No TIGRfam model hits

COGS Comparison

| Group | COG ID | COG Name | Top Hit | Score | Evalue |
|---|---|---|---|---|---|
| G | COG3525 | N-acetyl-beta-hexosaminidase | Chb | 84.7 | 2e-17 |

All genes with COG3525

Best KEGG Hit

| Name | Evalue | Percent Identity |
|---|---|---|
| possible beta-hexosaminidase A | 1e-141 | 45 |

Fig. 7 (sheet 3)

PRIAM EC Number Assignment and Map

| Evalue | EC Number |
|---|---|
| 1e-12 | 3.2.1.52 |

| Pathway(s) | Map Number |
|---|---|
| Beta-N-acetylhexosaminidase. | map00511 |
| Beta-N-acetylhexosaminidase | map00530 |
| Beta-N-acetylhexosaminidase | map00531 |
| Beta-N-acetylhexosaminidase | map00603 |
| Beta-N-acetylhexosaminidase | map01032 |

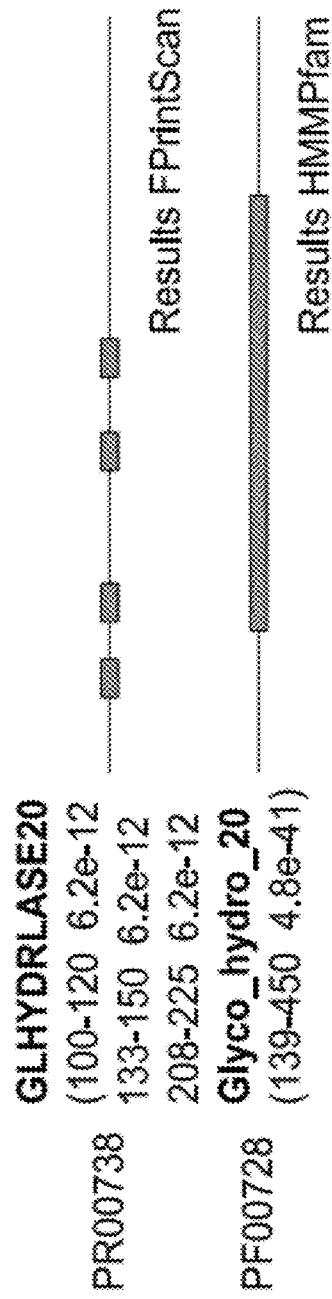
Fig. 7 (sheet 4)

Fig. 8 (sheet 1)

N-acetyl-beta-hexosaminidase III (EC:3.2.1.52 COG3525) Contig30 Gene 1639

Best Blast vs NR Hit

| Name | Evalue | Percent Identity |
|---|---|---|
| possible beta-hexosaminidase A [Bifidobacterium longum NCC2705] gi 23325247 gb AAN23923.1 possible beta-hexosaminidase A [Bifidobacterium longum NCC2705] | 0.0 | 75 |

Refresh BLAST results

Best Blast vs SwissProt/TREMBL Hit

| Name | Evalue | Percent Identity |
|---|---|---|
| Q8G826 Possible beta-hexosaminidase A. Bifidobacterium longum. | 0.0 | 75 |

PFam Model Comparison

| Model | Description | Evalue | Score |
|---|---|---|---|
| Glyco_hydro_20 | Glycosyl hydrolase family 20, catalytic | 1.2e-68 | 238.6 |

Refresh PFAM results

Fig. 8 (sheet 2)

TIGRfam Model Comparison

No TIGRfam model hits

COGS Comparison

| Group | COG ID | COG Name | Top Hit | Score | Evalue |
|---|---|---|---|---|---|
| G | COG3525 | N-acetyl-beta-hexosaminidase | Chb | 92.4 | 1e-19 |

All genes with COG3525

Best KEGG Hit

| Name | Evalue | Percent Identity |
|---|---|---|
| possible beta-hexosaminidase A | 0.0 | 75 |

Fig. 8 (sheet 3)

PRIAM EC Number Assignment and Map

| Evalue | EC Number |
|--------|-----------|
| 4e-19  | 3.2.1.52  |

| Pathway(s) | Map Number |
|------------|------------|
| Beta-N-acetylhexosaminidase. | map00511 |
| Beta-N-acetylhexosaminidase. | map00530 |
| Beta-N-acetylhexosaminidase. | map00531 |
| Beta-N-acetylhexosaminidase. | map00603 |
| Beta-N-acetylhexosaminidase. | map01032 |

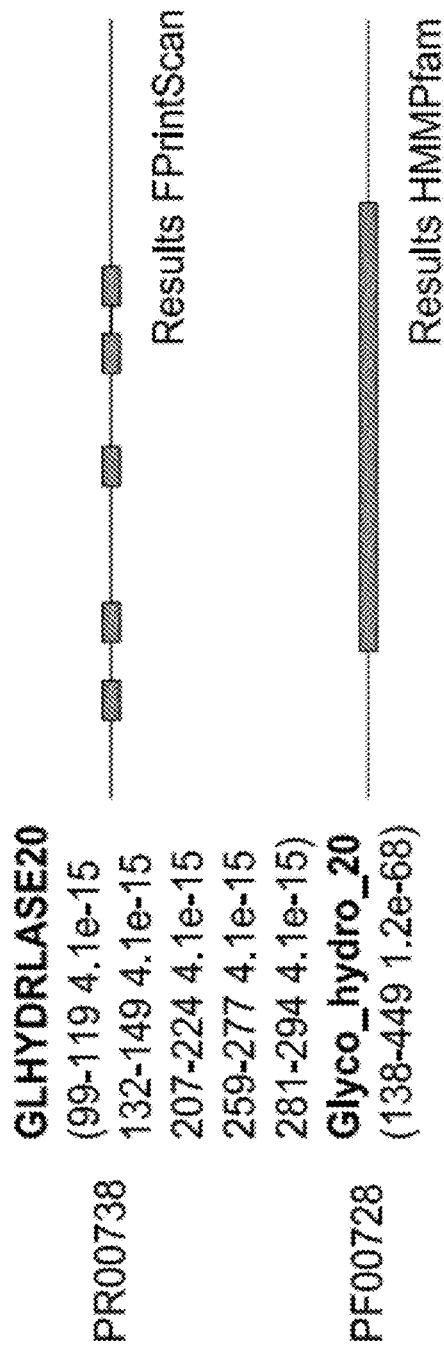
Fig. 8 (sheet 4)

Fig. 9 (sheet 1)

Beta-galactosidase I (EC:3.2.1.23 COG1874) Contig15 Gene 480

Best Blast vs NR Hit

| Name | Evalue | Percent identity |
|---|---|---|
| beta-galactosidase III [Bifidobacterium infantis] | 0.0 | 99 |

Refresh BLAST results

Best Blast vs SwissProt/TREMBL Hit

| Name | Evalue | Percent identity |
|---|---|---|
| Q93GI5 beta-galactosidase III. Bifidobacterium longum bv. Infantis. | 0.0 | 99 |

PFam Model Comparison

| Model | Description | Evalue | Score |
|---|---|---|---|
| Glyco_hydro_42 | Beta-galactosidase | 3e-220 | 742.3 |
| Glyco_hydro_42M | Beta-galactosidase trimerisation domain | 7.4e-79 | 273.3 |
| Glyco_hydro_42C | Beta-galactosidase C-terminal domain | 0.0016 | 25.6 |

Refresh PFAM results

Fig. 9 (sheet 2)

TIGRfam Model Comparison

No TIGRfam model hits

COGS Comparison

| Group | COG ID | COG Name | Top Hit | Score | Evalue |
|---|---|---|---|---|---|
| G | COG1874 | Beta-galactosidase | LacA | 393 | 1e-110 |

All genes with COG1874

Best KEGG Hit

| Name | Evalue | Percent Identity |
|---|---|---|
| bga: beta-galactosidase I [EC:3.2.1.23] [KO:K01190] | 0.0 | 95 |

Fig. 9 (sheet 3)

PRIAM EC Number Assignment and Map

| Evalue | EC Number |
|---|---|
| 1e-113 | 3.2.1.23 |

| Pathway(s) | Map Number |
|---|---|
| Beta-galactosidase. | map00052 |
| Beta-galactosidase. | map00511 |
| Beta-galactosidase. | map00531 |
| Beta-galactosidase. | map00561 |
| Beta-galactosidase. | map00600 |
| Beta-galactosidase. | map01032 |

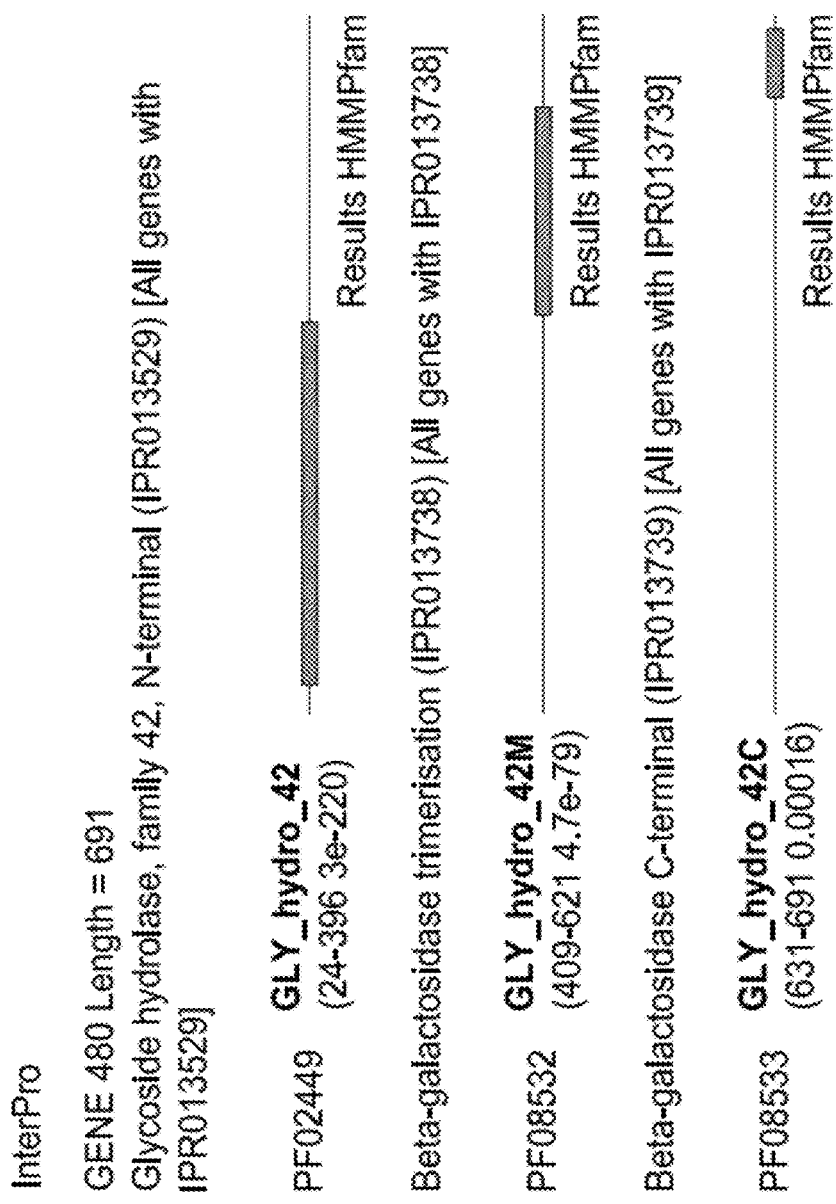
Fig. 9 (sheet 4)

Fig. 10 (sheet 1)

Beta-galactosidase II (EC:3.2.1.23 COG1874) Contig18 Gene 584

Best Blast vs NR Hit

| Name | Evalue | Percent Identity |
|---|---|---|
| beta-galactosidase III [Bifidobacterium adolescentis] | 0.0 | 82 |

Refresh BLAST results

Best Blast vs SwissProt/TREMBL Hit

| Name | Evalue | Percent Identity |
|---|---|---|
| Q5J883 beta-galactosidase. Bifidobacterium adolescentis. | 0.0 | 82 |

PFam Model Comparison

| Model | Description | Evalue | Score |
|---|---|---|---|
| Glyco_hydro_42 | Beta-galactosidase | 3.7e-211 | 712.1 |
| Glyco_hydro_42M | Beta-galactosidase trimerisation domain | 3.8e-67 | 233.7 |

Refresh PFAM results

Fig. 10 (sheet 2)

TIGRfam Model Comparison

No TIGRfam model hits

COGS Comparison

| Group | COG ID | COG Name | Top Hit | Score | Evalue |
|---|---|---|---|---|---|
| G | COG1874 | Beta-galactosidase | LacA | 322 | 8e-89 |

All genes with COG1874

Best KEGG Hit

| Name | Evalue | Percent Identity |
|---|---|---|
| bgaB; beta-galactosidase I [EC:3.2.1.23] [KO:K01190] | 0.0 | 69 |

Fig. 10 (sheet 3)

PRIAM EC Number Assignment and Map

| Evalue | EC Number |
|---|---|
| 1e-106 | 3.2.1.23 |

| Pathway(s) | Map Number |
|---|---|
| Beta-galactosidase. | map00052 |
| Beta-galactosidase. | map00511 |
| Beta-galactosidase. | map00531 |
| Beta-galactosidase. | map00561 |
| Beta-galactosidase. | map00600 |
| Beta-galactosidase. | map01032 |

Transmembrane TMHHMM 2.0

| Length | Helix Count | Topology |
|---|---|---|
| 826 | 1 | i34-56o |

Source: http://www.cbs.dtu.dk/services/TMHMM/

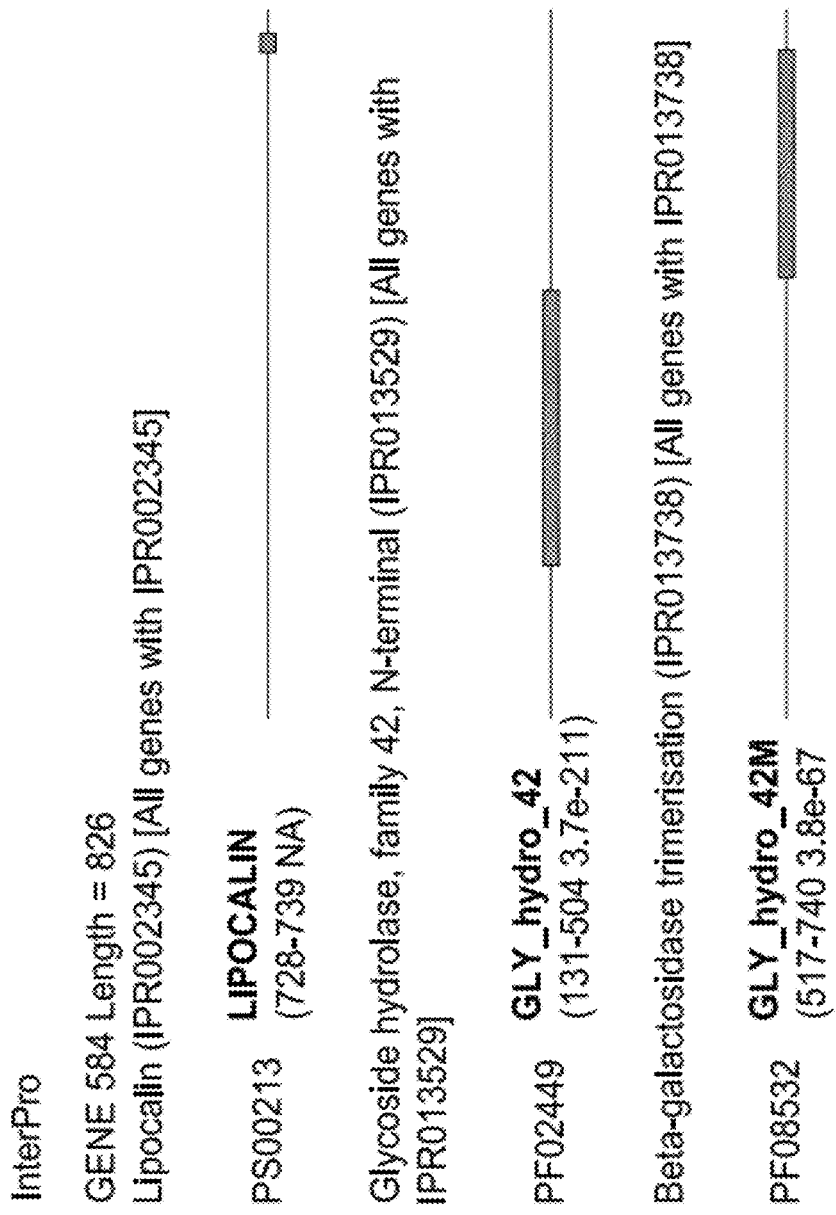
Fig. 10 (sheet 4)

Fig. 11 (sheet 1)

Beta-galactosidase III (EC:3.2.1.23 COG1874) Contig23 Gene 887

Best Blast vs NR Hit

| Name | Evalue | Percent Identity |
|---|---|---|
| beta-galactosidase [Bacillus halodurans C-125] gi\|15616263\|ref\|NP_244568.1\| beta-galactosidase [Bacillus halodurans C-125] gi\|25289543\|pir\|E84112 beta-galactosidase [imported] - Bacillus halodurans (strain TRUNCATED) | 1e-168 | 45 |

Refresh BLAST results

Best Blast vs SwissProt/TREMBL Hit

| Name | Evalue | Percent Identity |
|---|---|---|
| Q9K6M7 Beta-galactosidase. Bacillus halodurans. | 1e-168 | 45 |

PFam Model Comparison

| Model | Description | Evalue | Score |
|---|---|---|---|
| Glyco_hydro_42 | Beta-galactosidase | 2e-184 | 623.3 |
| Glyco_hydro_42M | Beta-galactosidase trimerisation domain | 2.1e-52 | 184.7 |

Refresh PFAM results

Fig. 11 (sheet 2)

TIGRfam Model Comparison

No TIGRfam model hits

COGS Comparison

| Group | COG ID | COG Name | Top Hit | Score | Evalue |
|---|---|---|---|---|---|
| G | COG1874 | Beta-galactosidase | LacA | 435 | 1.0e-123 |

All genes with COG1874

Best KEGG Hit

| Name | Evalue | Percent Identity |
|---|---|---|
| beta-galactosidase [EC:3.2.1.23] [KO:K01190] | 1e-168 | 45 |

*Fig. 11 (sheet 3)*

PRIAM EC Number Assignment and Map

| Evalue | EC Number |
|---|---|
| e-118 | 3.2.1.23 |

| Pathway(s) | Map Number |
|---|---|
| Beta-galactosidase. | map00052 |
| Beta-galactosidase. | map00511 |
| Beta-galactosidase. | map00531 |
| Beta-galactosidase. | map00561 |
| Beta-galactosidase. | map00600 |
| Beta-galactosidase. | map01032 |

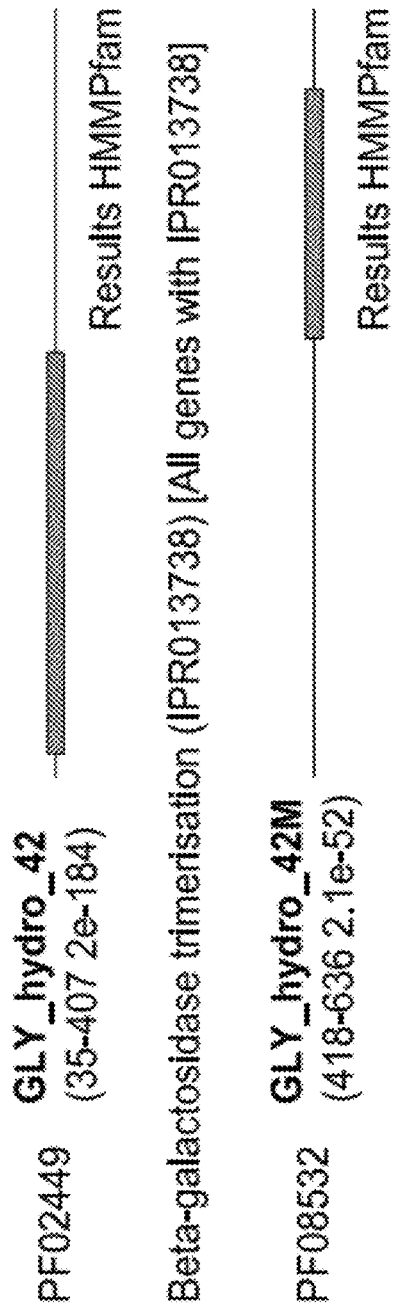
Fig. 11 (sheet 4)

*Fig. 12 (sheet 1)*

Beta-galactosidase IV (EC:3.2.1.23 COG1874) Contig28 Gene 1314

Best Blast vs NR Hit

| Name | Evalue | Percent Identity |
|---|---|---|
| hypothetical protein AcidDRAFT_2702 [Solibacter usitatus Ellin6076] gi|67861445|gb|EAM56476.1| hypothetical protein AcidDRAFT_2702 [Solibacter usitatus Ellin6076] | 2e-89 | 32 |

Refresh BLAST results

Best Blast vs SwissProt/TREMBL Hit

| Name | Evalue | Percent Identity |
|---|---|---|
| Q43UL1 Hypothetical protein. Solibacter usitatus Ellin6076. | 2e-89 | 32 |

PFam Model Comparison

No PFam model hits
Refresh PFAM results

*Fig. 12 (sheet 2)*

TIGRfam Model Comparison

No TIGRfam model hits

COGS Comparison

| Group | COG ID | COG Name | Top Hit | Score | Evalue |
|---|---|---|---|---|---|
| G | COG1874 | Beta-galactosidase | LacA | 45.7 | 1e-05 |

All genes with COG1874

Best KEGG Hit

| Name | Evalue | Percent identity |
|---|---|---|
| hypothetical protein | 5e-09 | 22 |

PRIAM EC Number Assignment and Map

No EC Pathway hits

*Fig. 13 (sheet 1)*

Beta-galactosidase V (EC:3.2.1.23 COG1874) Contig29 Gene 1402

Best Blast vs NR Hit

| Name | Evalue | Percent Identity |
|---|---|---|
| COG1874: Beta-galactosidase [Bifidobacterium longum DJO10A] | 1e-25 | 47 |

Refresh BLAST results

Best Blast vs SwissProt/TREMBL Hit

| Name | Evalue | Percent Identity |
|---|---|---|
| Q8G7K5 Beta-galactosidase I. Bifidobacterium longum. | 1e-25 | 47 |

PFam Model Comparison

No PFam model hits
Refresh PFAM results

Fig. 13 (sheet 2)

TIGRfam Model Comparison

No TIGRfam model hits

COGS Comparison

| Group | COG ID | COG Name | Top Hit | Score | Evalue |
|---|---|---|---|---|---|
| G | COG1874 | Beta-galactosidase | LacA | 37.3 | 8e-04 |

All genes with COG1874

Best KEGG Hit

| Name | Evalue | Percent Identity |
|---|---|---|
| bgaB; beta-galactosidase I [EC:3.2.1.23] [KO:K01190] | 7e-26 | 47 |

PRIAM EC Number Assignment and Map

No EC Pathway hits

Fig. 14 (sheet 1)

Fucose dissimilation pathway protein I (COG4154) Contig20 Gene 785

Best Blast vs NR Hit

| Name | Evalue | Percent Identity |
|---|---|---|
| Si:ch211-217g15.2 [Danio rerio] gi|27802779|emb|CAD60840.1| novel protein [Danio rerio] gi|54633338|ref|NP_001004530.1| hypothetical protein LOC 447896 [Danio rerio] | 3e-33 | 51 |

Refresh BLAST results

Best Blast vs SwissProt/TREMBL Hit

| Name | Evalue | Percent Identity |
|---|---|---|
| Q7ZZ03 Novel protein (Si:ch211-217g15.2). Brachydanio rerio (Zebrafish) (Danio rerio) | 3e-33 | 51 |

PFam Model Comparison

| Model | Description | Evalue | Score |
|---|---|---|---|
| RbsD_FucU | RbsD/FucU transport protein family | 4e-23 | 87.4 |

Refresh PFAM results

Fig. 14 (sheet 2)

TIGRfam Model Comparison

No TIGRfam model hits

COGS Comparison

| Group | COG ID | COG Name | Top Hit | Score | Evalue |
|---|---|---|---|---|---|
| G | COG4154 | Fucose dissimilation pathway protein FucU | FucU | 159 | 7e-41 |

All genes with COG4154

Best KEGG Hit

| Name | Evalue | Percent Identity |
|---|---|---|
| Sich211-217g15.2 | 2e-33 | 51 |

PRIAM EC Number Assignment and Map

No EC Pathway hits

Fig. 14 (sheet 3)

InterPro

GENE 785 Length = 148
RbsD or FucU transport (IPR007721) [All genes with IPR007721]

PF05025 RbsD_FucU
(3-145 4e-23)

Results HMMPfam

Fig. 15 (sheet 1)

Fucose dissimilation pathway protein II (COG4154) Contig22 Gene 816

Best Blast vs NR Hit

| Name | Evalue | Percent identity |
|---|---|---|
| COG4154: Fucose dissimilation pathway protein FucU [Actinobacillus pleuropneumoniae serovar. 1 str. 4074] | 1e-32 | 50 |

Refresh BLAST results

Best Blast vs SwissProt/TREMBL Hit

| Name | Evalue | Percent identity |
|---|---|---|
| Q4RQE5 Chromosome 17 SCAF 15006, whole genome shotgun sequence (Fragment). Tetraodon nigroviridis (Green puffer). | 5e-31 | 46 |

PFam Model Comparison

| Model | Description | Evalue | Score |
|---|---|---|---|
| RbsD_FucU | RbsD/FucU transport protein family | 3.7e-21 | 80.9 |

Refresh PFAM results

*Fig. 15 (sheet 2)*

TIGRfam Model Comparison

No TIGRfam model hits

COGS Comparison

| Group | COG ID | COG Name | Top Hit | Score | Evalue |
|---|---|---|---|---|---|
| G | COG4154 | Fucose dissimilation pathway protein FucU | FucU | 166 | 5e-43 |

All genes with COG4154

Best KEGG Hit

| Name | Evalue | Percent Identity |
|---|---|---|
| LOC613571: hypothetical protein LOC613571 | 5e-32 | 46 |

PRIAM EC Number Assignment and Map

No EC Pathway hits

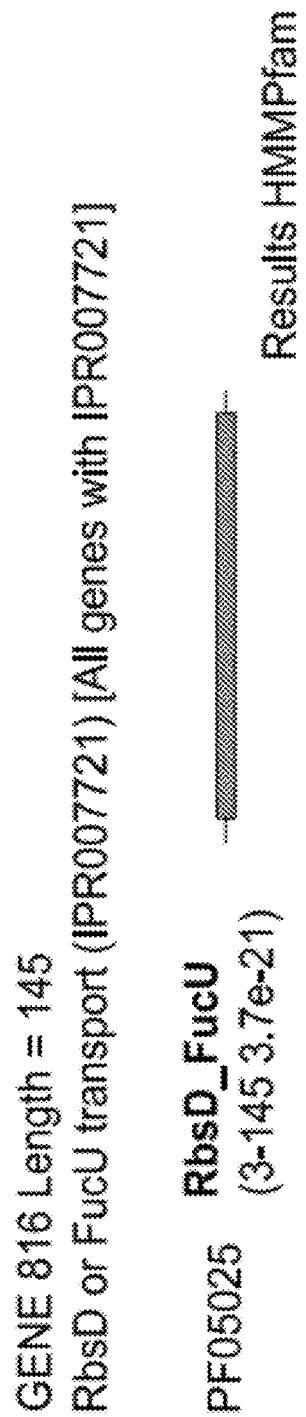
Fig. 15 (sheet 3)

Fig. 16 (sheet 1)

N-acetylmannosamine-6-phosphate 2-epimerase I (EC:5.1.3.9 COG3010)
Contig23 Gene 875

Best Blast vs NR Hit

| Name | Evalue | Percent Identity |
|---|---|---|
| N-acetylmannosamine-6-phosphate 2-epimerase [Propionibacterium acnes KPA171202] gi|50841046|gb|AAT83713.1| N-acetylmannosamine-6-phosphate 2-epimerase [Propionibacterium acnes KPA171202] gi|67460804|sp|Q6A6A0|NANE: PRO- TRUNCATED | 3e-74 | 59 |

Refresh BLAST results

Best Blast vs SwissProt/TREMBL Hit

| Name | Evalue | Percent Identity |
|---|---|---|
| Q6A6A0 Putative N-acetylmannosamine-6-P epimerase (EC:5.1.3.9) (ManNAc-6-P epimerase). Propionibacterium acnes. | 3e-74 | 59 |

Fig. 16 (sheet 2)

PFam Model Comparison

| Model | Description | Evalue | Score |
|---|---|---|---|
| NanE | Putative N-acetylmannosamine-6-phosphate epimerase | 1.1e-65 | 228.8 |

Refresh PFAM results

TIGRfam Model Comparison

No TIGRfam model hits

COGS Comparison

| Group | COG ID | COG Name | Top Hit | Score | Evalue |
|---|---|---|---|---|---|
| G | COG3010 | Putative N-acetylmannosamine-6-phosphate epimerase | NanE | 238 | 2e-64 |

All genes with COG3010

Fig. 16 (sheet 3)

Best KEGG Hit

| Name | Evalue | Percent Identity |
|---|---|---|
| N-acetylmannosamine-6-phosphate 2-epimerase [EC:5.1.3.9] [KO:K01788] | 2e-74 | 59 |

PRIAM EC Number Assignment and Map

| Evalue | EC Number |
|---|---|
| 2e-61 | 5.1.3.9 |

| Pathway(s) | Map Number |
|---|---|
| N-acylglucosamine-6-phosphate 2-epimerase | map00530 |

Fig. 16 (sheet 4)

InterPro

GENE 875 Length = 231
FMN/related compound-binding core (IPR003009) [All genes with IPR003009]

PS50264  FMN_ENZYMES
(182-217  12.329)

Results ProfileScan

Putative N-acetylmannosamine-6-phosphate epimerase (IPR007260) [All genes with IPR007260]

PF04131  NanE
(37-231  1.1e-65)

Results HMMPfam

Fig. 17 (sheet 1)

N-acetylmannosamine-6-phosphate 2-epimerase II (EC:5.1.3.9 COG3010)
Contig30 Gene 1561

Best Blast vs NR Hit

| Name | Evalue | Percent Identity |
|---|---|---|
| N-acetylmannosamine-6-phosphate 2-epimerase [Propionibacterium acnes KPA171202] gi|50841046|gb|AAT83713.1| N-acetylmannosamine-6-phosphate 2-epimerase [Propionibacterium acnes KPA171202] gi|67460804|sp|Q6A6A0|NANE: PRO- TRUNCATED | 2e-76 | 64 |

Refresh BLAST results

Best Blast vs SwissProt/TREMBL Hit

| Name | Evalue | Percent Identity |
|---|---|---|
| Q6A6A0 Putative N-acetylmannosamine-6-phosphate 2-epimerase (EC:5.1.3.9) (ManNAc-6-P epimerase). Propionibacterium acnes. | 2e-76 | 64 |

Fig. 17 (sheet 2)

PFam Model Comparison

| Model | Description | Evalue | Score |
|---|---|---|---|
| NanE | Putative N-acetylmannosamine-6-phosphate epimerase | 4.6e-65 | 226.8 |

Refresh PFAM results

TIGRFAM Model Comparison

No TIGRfam model hits

COGS Comparison

| Group | COG ID | COG Name | Top Hit | Score | Evalue |
|---|---|---|---|---|---|
| G | COG3010 | Putative N-acetylmannosamine-6-phosphate epimerase | NanE | 244 | 4e-66 |

All genes with COG3010

Fig. 17 (sheet 3)

Best KEGG Hit

| Name | Evalue | Percent identity |
|---|---|---|
| N-acetylmannosamine-6-phosphate 2-epimerase [EC:5.1.3.9] [KO:K01788] | 1e-76 | 64 |

PRIAM EC Number Assignment and Map

| Evalue | EC Number |
|---|---|
| 3e-65 | 5.1.3.9 |

| Pathway(s) | Map Number |
|---|---|
| N-acylglucosamine-6-phosphate 2-epimerase | map00530 |

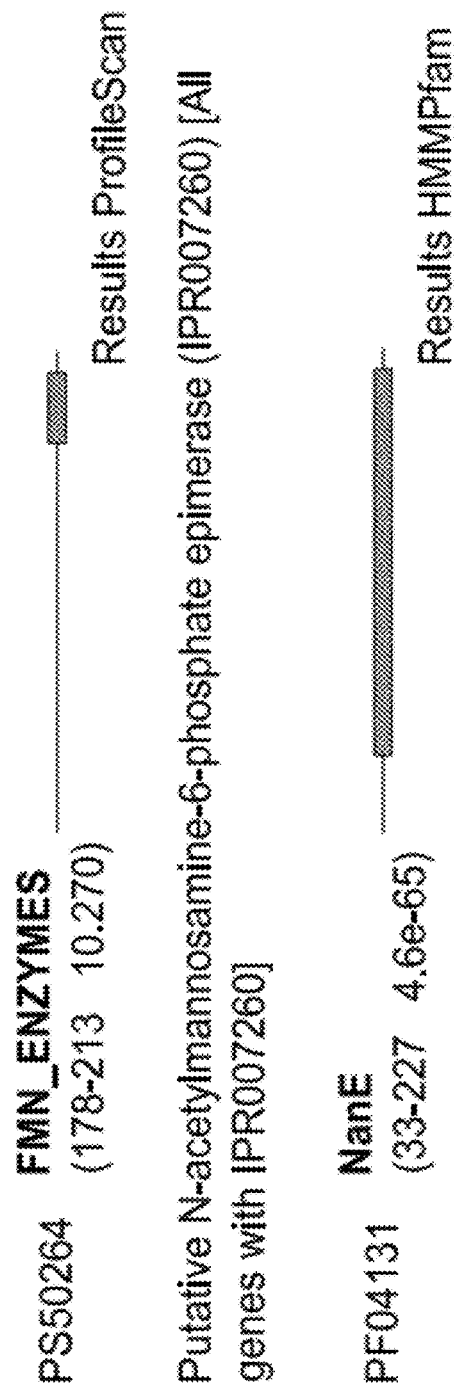
Fig. 17 (sheet 4)

Fig. 18 (sheet 1)

Sialate O-acetylesterase (EC:3.1.1.53) Contig15 Gene 377

Best Blast vs NR Hit

| Name | Evalue | Percent Identity |
|---|---|---|
| Sialate O-acetylesterase [Solibacter usitatus Ellin6076] gi| 67863722|gb|EAM58732.1| Sialate O-acetylesterase [Solibacter usitatus Ellin6076] | 2e-59 | 30 |

Refresh BLAST results

Best Blast vs SwissProt/TREMBL Hit

| Name | Evalue | Percent Identity |
|---|---|---|
| Q440Z0 Sialate O-acetylesterase precursor (EC:3.1.1.53). Solibacter usitatus Ellin6076. | 2e-59 | 30 |

Fig. 18 (sheet 2)

PFam Model Comparison

| Model | Description | Evalue | Score |
|---|---|---|---|
| DUF303 | Domain of unknown function (DUF303) | 1.1e-35 | 129.2 |

Refresh PFAM results

TIGRfam Model Comparison

No TIGRfam model hits

COGS Comparison

No COGS model hits

Fig. 18 (sheet 3)

Best KEGG Hit

| Name | Evalue | Percent Identity |
|---|---|---|
| sialate O-acetylesterase (EC:3.1.1.53) | 7e-50 | 28 |

PRIAM EC Number Assignment and Map

| Evalue | EC Number |
|---|---|
| 1e-18 | 3.1.1.53 |

| Pathway(s) | Map Number |
|---|---|
| Sialate O-acetylesterase | -- |

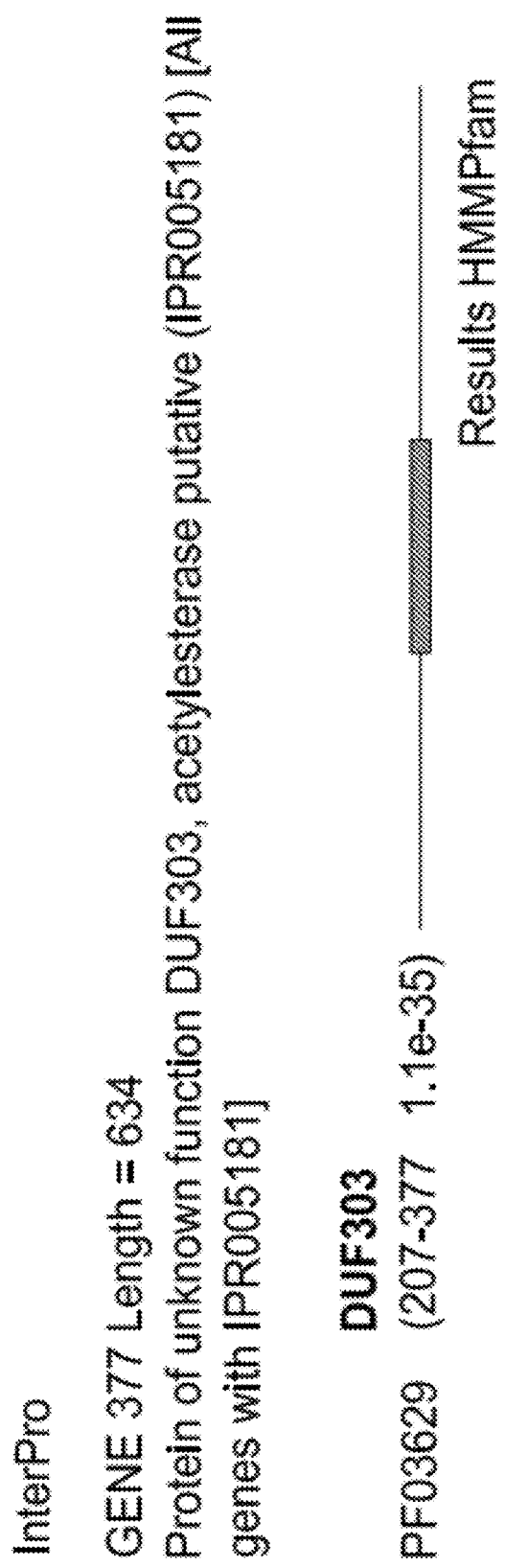
Fig. 18 (sheet 4)

Fig. 19 (sheet 1)

N-acetylneuraminate lyase I (EC:4.2.1.52 COG0329) Contig15 Gene 498

Best Blast vs NR Hit

| Name | Evalue | Percent Identity |
|---|---|---|
| Dihydrodipicolinate synthase (DHDPS) gi\|23465759\|ref\| NP696362.1\| dihydrodipicolinate synthase [Bifidobacterium longum NCC2705]\|gi\|23326445\|gb\|AAN24998.1\| dihydrodipicolinate synthase [Bifidobacterium longum] - TRUNCATED Refresh BLAST results | 1e-164 | 98 |

Best Blast vs SwissProt/TREMBL Hit

| Name | Evalue | Percent Identity |
|---|---|---|
| Q8G527 Dihydrodipicolinate synthase (EC:4.2.1.52) (DHDPS). Bifidobacterium longum. | 1e-164 | 98 |

Fig. 19 (sheet 2)

PFam Model Comparison

| Model | Description | Evalue | Score |
|---|---|---|---|
| DHDPS | Dihydrodipicolinate synthase family | 1.4e-83 | 288.2 |

Refresh PFAM results

TIGRfam Model Comparison

| Model | Description | Evalue | Score |
|---|---|---|---|
| dapA | dapA: dihydrodipicolinate synthase | 7e-80 | 274.3 |

COGS Comparison

| Group | COG ID | COG Name | Top Hit | Score | Evalue |
|---|---|---|---|---|---|
| E | COG0329 | Dihydrodipicolinate synthase/ N-acetylneuraminate lyase | DapA | 248 | 4e-67 |
| M | COG0329 | Dihydrodipicolinate synthase/ N-acetylneuraminate lyase | DapA | 248 | 4e-67 |

All Genes with COG0329

Fig. 19 (sheet 3)

Best KEGG Hit

| Name | Evalue | Percent Identity |
|---|---|---|
| dapA; dihydrodipicolinate synthase [EC:4.2.1.52] [KO:K01714] | 1e-164 | 98 |

PRIAM EC Number Assignment and Map

| Evalue | EC Number |
|---|---|
| 1e-16 | 4.2.1.52 |

| Pathway(s) | Map Number |
|---|---|
| Dihydrodipicolinate synthase | map00300 |

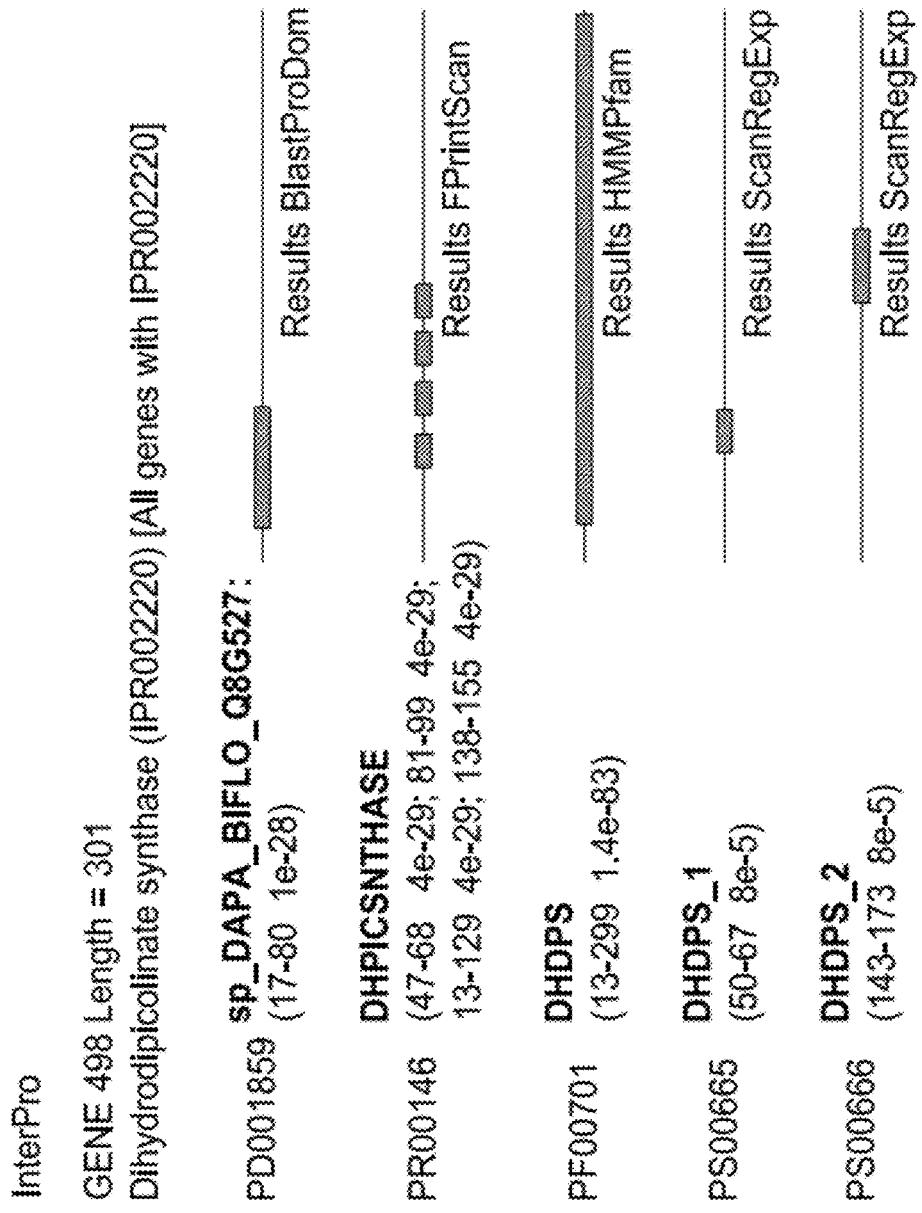
Fig. 19 (sheet 4)

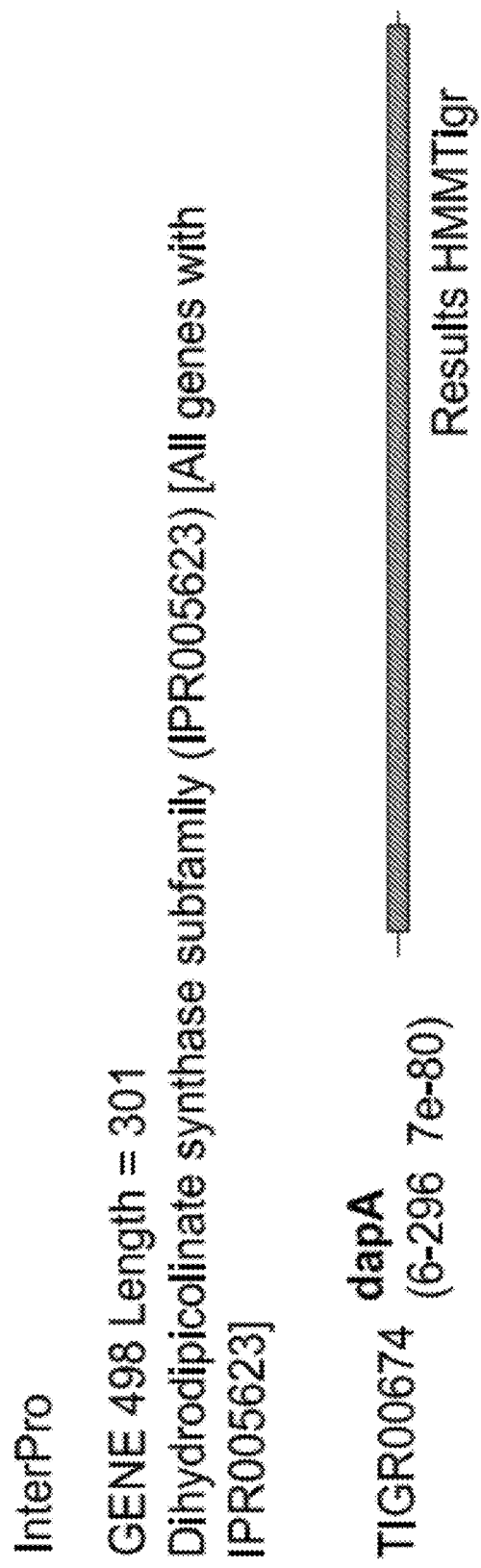
Fig. 19 (sheet 5)

*Fig. 20 (sheet 1)*

N-acetylneuraminate lyase II (EC:4.2.1.52 COG0329) Contig22 Gene 817

Best Blast vs NR Hit

| Name | Evalue | Percent Identity |
|---|---|---|
| KpLE2 phage-like element; putative synthase [Escherichia coli K12] gi|1790751|gb|AAC77254.1| putative lyase/synthase; KpLE2 phage-like element; putative synthase [Escherichia coli K12] gi|537139|gb|AAA97194.1| ORF f31 - TRUNCATED | 2e-54 | 37 |

Refresh BLAST results

Best Blast vs SwissProt/TREMBL Hit

| Name | Evalue | Percent Identity |
|---|---|---|
| Q3AClO Dihydrodipicolinate synthase (EC:4.2.1.52). Carboxydothermus hydrogenoformans (strain Z-2901/DSM 6008). | 2e-54 | 37 |

Fig. 20 (sheet 2)

PFam Model Comparison

| Model | Description | Evalue | Score |
|---|---|---|---|
| DHDPS | Dihydrodipicolinate synthase family | 9.7e-56 | 195.8 |

Refresh PFAM results

TIGRfam Model Comparison

No TIGRfam model hits

COGS Comparison

| Group | COG ID | COG Name | Top Hit | Score | Evalue |
|---|---|---|---|---|---|
| E | COG0329 | Dihydrodipicolinate synthase/ N-acetylneuraminate lyase | DapA | 233 | 2e-62 |
| M | COG0329 | Dihydrodipicolinate synthase/ N-acetylneuraminate lyase | DapA | 233 | 2e-62 |

All genes with COG0329

Fig. 20 (sheet 3)

Best KEGG Hit

| Name | Evalue | Percent Identity |
|---|---|---|
| dapA2; dihydrodipicolinate synthase [EC:4.2.1.52] [KO:K01714] | 9e-55 | 37 |

PRIAM EC Number Assignment and Map

| Evalue | EC Number |
|---|---|
| 3e-27 | 4.2.1.52 |

| Pathway(s) | Map Number |
|---|---|
| Dihydrodipicolinate synthase | map00300 |

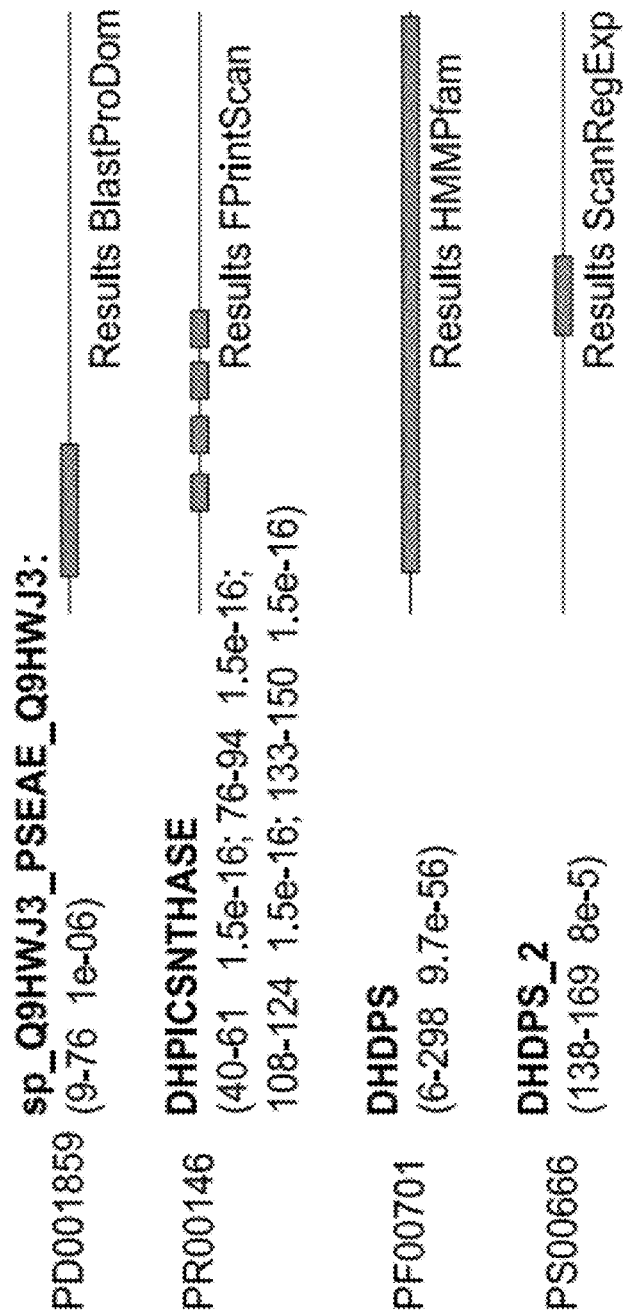
Fig. 20 (sheet 4)

Fig. 21 (sheet 1)

N-acetylneuraminate lyase III (EC:4.2.1.52 COG0329) Contig23 Gene 827

Best Blast vs NR Hit

| Name | Evalue | Percent Identity |
|---|---|---|
| dihydrodipicolinate synthase [Propionibacterium acnes KPA171202] gi|50841047|gb|AAT83714.1| dihydrodipicolinate synthase [Propionibacterium acnes KPA171202] | 1e-97 | 61 |

Refresh BLAST results

Best Blast vs SwissProt/TREMBL Hit

| Name | Evalue | Percent Identity |
|---|---|---|
| Q6A699 Dihydrodipicolinate synthase (EC:4.2.1.52). Propionibacterium acnes. | 1e-97 | 61 |

Fig. 21 (sheet 2)

PFam Model Comparison

| Model | Description | Evalue | Score |
|---|---|---|---|
| DHDPS | Dihydrodipicolinate synthase family | 1.9e-20 | 78.5 |

Refresh PFAM results

TIGRfam Model Comparisoned

No TIGRfam model hits

COGS Comparison

| Group | COG ID | COG Name | Top Hit | Score | Evalue |
|---|---|---|---|---|---|
| E | COG0329 | Dihydrodipicolinate synthase/ N-acetylneuraminate lyase | DapA | 210 | 1e-55 |
| M | COG0329 | Dihydrodipicolinate synthase/ N-acetylneuraminate lyase | DapA | 210 | 1e-55 |

All genes with COG0329

*Fig. 21 (sheet 3)*

Best KEGG Hit

| Name | Evalue | Percent Identity |
|---|---|---|
| dihydrodipicolinate synthase [EC:4.2.1.52] [KO:K01714] | 6e-98 | 61 |

PRIAM EC Number Assignment and Map

| Evalue | EC Number |
|---|---|
| 4e-12 | 4.2.1.52 |

| Pathway(s) | Map Number |
|---|---|
| Dihydrodipicolinate synthase | map00300 |

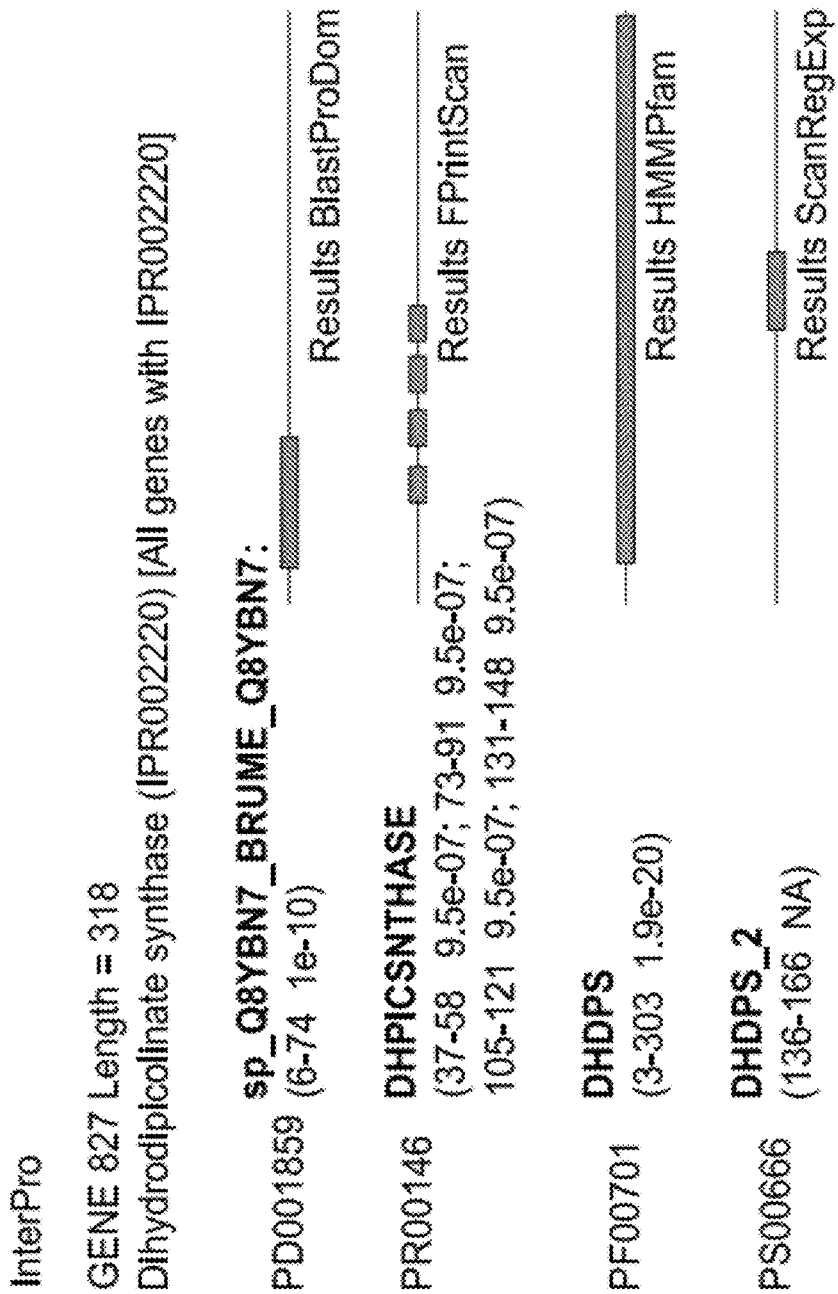
Fig. 21 (sheet 4)

Fig. 22 (sheet 1)

N-acetylneuraminate lyase IV (EC:4.2.1.52 COG0329) Contig30 Gene 1567

Best Blast vs NR Hit

| Name | Evalue | Percent Identity |
|---|---|---|
| dihydrodipicolinate synthase [Propionibacterium acnes KPA171202] gi\|50841047\|gb AAT83714.1\| dihydrodipicolinate synthase [Propionibacterium acnes KPA171202] | 5e-99 | 60 |

Refresh BLAST results

Best Blast vs SwissProt/TREMBL Hit

| Name | Evalue | Percent Identity |
|---|---|---|
| Q6A699 Dihydrodipicolinate synthase (EC:4.2.1.52). Propionibacterium acnes. | 5e-99 | 60 |

Fig. 22 (sheet 2)

PFam Model Comparison

| Model | Description | Evalue | Score |
|---|---|---|---|
| DHDPS | Dihydrodipicolinate synthase family | 1.3e-17 | 69.1 |

Refresh PFAM results

TIGRfam Model Comparison

No TIGRfam model hits

COGS Comparison

| Group | COG ID | COG Name | Top Hit | Score | Evalue |
|---|---|---|---|---|---|
| E | COG0329 | Dihydrodipicolinate synthase/ N-acetylneuraminate lyase | DapA | 203 | 2e-53 |
| M | COG0329 | Dihydrodipicolinate synthase/ N-acetylneuraminate lyase | DapA | 203 | 2e-53 |

All genes with COG0329

Fig. 22 (sheet 3)

Best KEGG Hit

| Name | Evalue | Percent Identity |
|---|---|---|
| dihydrodipicolinate synthase [EC:4.2.1.52] [KO:K01714] | 3e-99 | 60 |

PRIAM EC Number Assignment and Map

| Evalue | EC Number |
|---|---|
| 4e-13 | 4.2.1.52 |

| Pathway(s) | Map Number |
|---|---|
| Dihydrodipicolinate synthase | map00300 |

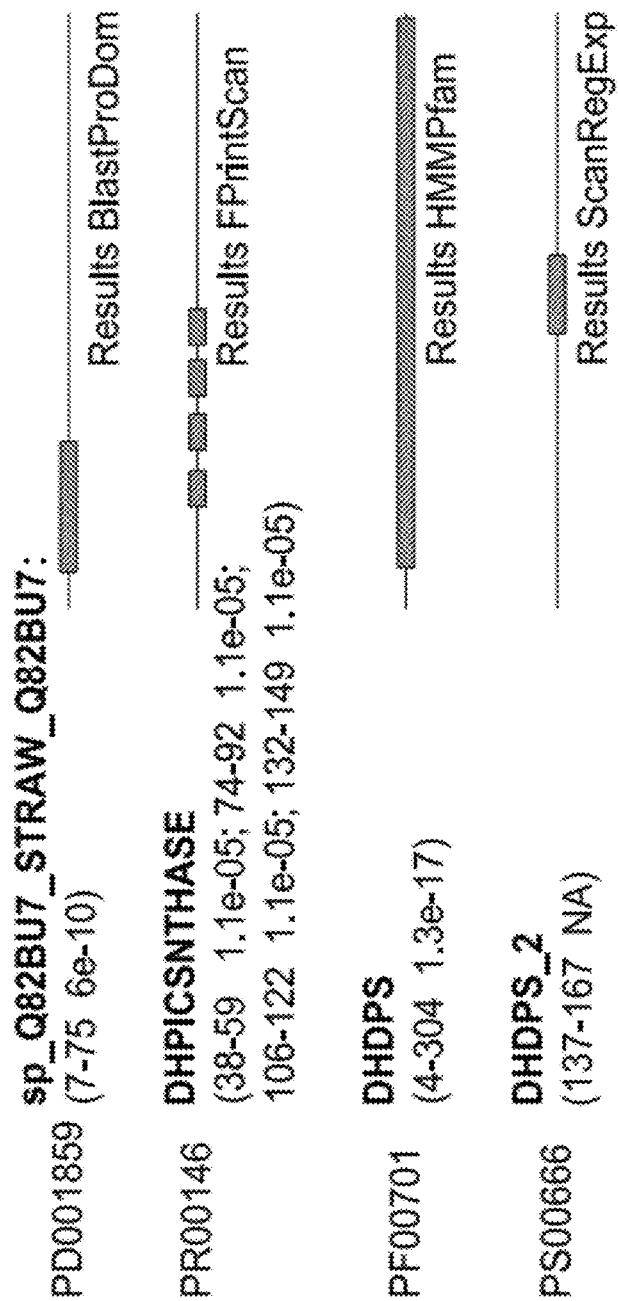
Fig. 22 (sheet 4)

Fig. 23 (sheet 1)

N-acetyl-beta-hexosaminidase III (EC:3.2.1.52 COG3525) Contig30 Gene 1639 - 75% >gi|23464684|ref|NP_695287.1| possible beta-hexosaminidase A Bifidobacterium longum NCC2705] gi|23325247|gb|AAN23923.1| possible beta-hexosaminidase A Bifidobacterium longum NCC2705]
Length = 711

Score = 1051 bits (2718), Expect = 0.0
Identities = 536/711 (75%), Positives = 570/711 (80%),
Gaps = 60/711 (8%)

```
Query: 1    VPTSEHKADDATRHLTLIPAPVTLEYTHGTALIGPLVTIE----------DADQSWETLP 50
            +PT E+KAD AT   LTLIPAPVTLEYTHGTA+IG LVTIE         DAD++WETLP
Sbjct: 1    MPTFEYKADAATPCLTLIPAPVTLEYTHGTAMIGSLVTIEKRIPEYAVTEDADETWETLP 60

Query: 51   IEQLSDELRHRYGVTVLRRRT---------------------------------HGTVI 76
            IEQLS EL    GV V  RR                                  +GTVI
Sbjct: 61   IEQLSSELERYCGVAVRTRRVLTATDEADAGANAAEKARDAGVGAGAGAGAPAAMNGTVI 120
```

Fig. 23 (sheet 2)

```
Query:  77 SLGLDSRLAHDEYTLDVSESEGIRVRGGGESGLRYGLQTLRQIIGQTSRAIPCLHIQDKP 136
            L +D+RLAHDEYTLDV  S+ I VRGG ESGLRYG+QTLRQ+I QTSR +PCLHIQDKP
Sbjct: 121 LLCVDARLAHDEYTLDVFASDTIAVRGGSESGLRYGMQTLRQMIRQTSRTLPCLHIQDKP 180

Query: 137 AFAVRAYSLDVTRGRVPTMEFLTWFVDQLALYKYNQFQLYVEHAFAFVELSEAWRGTDPL 196
            AFAVRAYSLDVTRGRVPTM FLTWF+DQLALYKYNQFQLYVEHAFAF ELSEAWRGTDPL
Sbjct: 181 AFAVRAYSLDVTRGRVPTMAFLTWFIDQLALYKYNQFQLYVEHAFAFGELSEAWRGTDPL 240

Query: 197 TAADITYLDEYCARRGIELVPSLATFGHMYMNLRTREHRGLGEFPEDADRPFSFIERMEH 256
            TA DI +LDEYCA   GIELVPSLATFGHMYMNLRTREHRGLGEFPEDADRPFSFIERMEH
Sbjct: 241 TADDIMFLDEYCAHHGIELVPSLATFGHMYMNLRTREHRGLGEFPEDADRPFSFIERMEH 300

Query: 257 HTLNAADPKAHDFASRLIEEYAPLFRSKSFNIGGDETFDLGRGRSAQDAPEAGRDELYAG 316
            HTLNAA+PK+HDFASRLIEEYAPLFRS+SFNIGGDETFDLGRGRS  QD+P A RDELYA
Sbjct: 301 HTLNAANPKSHDFASRLIEEYAPLFRSRSFNIGGDETFDLGRGRSVQDSPGASRDELYAD 360
```

Fig. 23 (sheet 3)

```
Query: 317 FVRDLCETLARHGRQPMLWADIALESPRTMDLLPGDITMLNWMYEPQIDESKIQTIATQG 376
            FV+DLC TLA G QPMLWADIALE+P TMDLLPGDITMLNWMYEP IDESKIQTIA+QG
Sbjct: 361 FVKDLCSTLAHRGLQPMLWADIALENPHTMDLLPGDITMLNWMYEPDIDESKIQTIASQG 420

Query: 377 RRQFVCPAVRAWSRFFPDYAGAWLNTYHMALAGTKYDAEGMVVTDWGDYGHVNDPRLSVP 436
            RRQFVCPAVRAWSRFFPDY GAWLNTY MA+AG KY AEGMVVTDWGDYGHVNDPRLSVP
Sbjct: 421 RRQFVCPAVRAWSRFFPDYDGAWLNTYRMAVAGLKYGAEGMVVTDWGDYGHVNDPRLSVP 480

Query: 437 GLCYGAQNAWNPIEIDAHEMNRRIISALVYGDESGRIMDCLARIDSDGVSFPWDLAVQVLE 496
            GLCYGAQNAWNP+ IDA EMN RIS L YGDESG +MD LARIDSDGVSFPWDLAVQVLE
Sbjct: 481 GLCYGAQNAWNPVAIDACEMNHRISNLAYGDESGWLMDSLARIDSDGVSFPWDLAVQVLE 540

Query: 497 LEYGSGTGALNMDVAACMERSSGGKLTLDRTLGCDDARRRMLQWNRERIERRRDCDQVLR 556
            LEYGSGTG LN DVA+C+ERS GG+L DRTLGC DARRR+L N R+ERRRDCD+ L
Sbjct: 541 LEYGSGTGMLNTDVASCVERSCGGELVFDRTLGCADARRRLLLRNHARLERRRDCDRALI 600
```

Fig. 23 (sheet 4)

```
Query: 557 DCGDAFA-----GLDKGGLTAEFLSVMLDGQRLFNELGEELLALADGKDV------------ 601
            DCG A        G  +GGL    E L VMLDGQRLFN LGEELL LA  G+D
Sbjct: 601 DCGSAVVAVLDGSARGGLNPELLWVMLDGQRLFNRLGEELLVLAGGEDACDTKDVTGRAL 660

Query: 602 -GSGANRLAADLELWFERYRAQWLSVGRHAELARIAHVVWSLADILRRGAL 651
            S    RLAADLELWFERYR  QWLS+GR+AELARIAHVVWS ADILRRGAL
Sbjct: 661 DASRRARLAADLELWFERYRVQWLSIGRYAELARIAHVVWSFADILRRGAL 711
```

Fig. 24 (sheet 1)

Beta-galactosidase II (EC: 3.2.1.23 COG1874) Contig18 Gene 584 - 82%
>gi|51339205|gb|AAR24113.1| beta-galactosidase
Bifidobacterium adolescentis]
          Length = 701

Score = 1227 bits (3175), Expect = 0.0
Identities = 588/714 (82%), Positives = 628/714 (87%),
Gaps = 16/714 (2%)

Query: 109  ARRDFAWPKLLTADGRGIAFGGDYNPDQWPEDVWDDDIRLMGQAGVNTVALAIFSWDRLQ  168
            ARR+F   WP+LLTADGRGIAFGGDYNPDQW ED+WDDDIRLM QAGVNTVALAIFSWDR+Q
Sbjct: 3    ARRNFEWPELLTADGRGIAFGGDYNPDQWSEDIWDDDIRLMKQAGVNTVALAIFSWDRIQ  62

Query: 169  PTEDHWNFDWLDRIIDKLGQAGIAVDLASATATAPLWLYENHPEVLPRDKYGHPVNAGSR  22
            PTED W+F  WLDRIIDKLG  AGI VDLASATATAPLWLYE+HPEVLPRDKYGHPVNAGSR
Sbjct: 63   PTEDRWDFGWLDRIIDKLGNAGIVDLASATATAPLWLYESHPEVLPRDKYGHPVNAGSR  122

Fig. 24 (sheet 2)

```
Query: 229 QSWSPTSPVFKEYALTLCRKLAERYGTNPYVTAWHMGNEYGWNNRDDYSDNALEAFRAWC 288
           QSWSPTSPVFKEYALTLCRKLAERYGTNPYVTAWHMGNEYGWNNR+DYSDNALEAFRAWC
Sbjct: 123 QSWSPTSPVFKEYALTLCRKLAERYGTNPYVTAWHMGNEYGWNNREDYSDNALEAFRAWC 182

Query: 289 RRKYGTIDALNQAWGTTFWGQEMTGFDEVLIPRFMGAD-SMVNPGQKLDFERFGNDMLLD 347
           RRKYGTIDALNQAWGTTFWGQEM GFDEVL P   G    P  +    FERFGNDMLLD
Sbjct: 183 RRKYGTIDALNQAWGTTFWGQEMNGFDEVLHPTVHGRRLRWSTPARSSTFERFGNDMLLD 242

Query: 348 FYKAERDAIAEICPDKPFTTNFMISTDQCCMDYAAWAEEVNFVSNDHYFHEGESHLDELA 407
           FYKAERDAIAEICPDKPFTTNFM+STDQCCMDYAAWA+EVNFVSNDHYFHEGESHLDELA
Sbjct: 243 FYKAERDAIAEICPDKPFTTNFMVSTDQCCMDYAAWAKEVNFVSNDHYFHEGESHLDELA 302

Query: 408 CSDALVDSLALGKPWYVMEHSTSAVQWKPLNTRKRNGETVRDSLAHVAMGADAINFFQWR 467
           CSDAL+DSLALGKPWYVMEHSTSAVQWKPLNTRKR  GETVRDSLAHVAMGADAINFFQWR
Sbjct: 303 CSDALMDSLALGKPWYVMEHSTSAVQWKPLNTRKRKGETVRDSLAHVAMGADAINFFQWR 362
```

Fig. 24 (sheet 3)

```
Query: 468 ASAFGAEAFHSAMVPHAGENTKLFRQVCELGATLQALADAGVQGSELAHADTAILFSAES 527
            ASAFGAEAFHSAMVPHAGE+TKLFRQVCELGA+L   LADAGVQG+ELAH+DTAILFSAES
Sbjct: 363 ASAFGAEAFHSAMVPHAGEDTKLFRQVCELGASLHTLADAGVQGTELAHSDTAILFSAES 422

Query: 528 EWATRSETLPSMKLNHWHDVRDWYRAFLNAGARADIVPLAYDWSSYKTIVLPTVLMLSDA 587
            EWATRS+TLPSMKLNHWHDVRDWYRAFL+AG+RADIVPLAYDWSSYKT+VLPTVL+LS A
Sbjct: 423 EWATRSQTLPSMKLNHWHDVRDWYRAFLDAGSRADIVPLAYDWSSYKTVVLPTVLILSAA 482

Query: 588 DTRRLAGFVQDGGRVVVGYATGLLDERFHTWLGGYPGAGDGLLRSMLGVRGEEFNILGTE 647
            DT+RLA F   GGRVVVGYATGL+DE FHTWLGGYPGAGDGLLRSMLGVRGEEF ILG E
Sbjct: 483 DTQRLADFAAAGGRVVVGYATGLIDEHFHTWLGGYPGAGDGLLRSMLGVRGEEFTILGAE 542

Query: 648 TEDEPSEIRLASTGDSPTMDGAVTRLWQNDVTVAGPHVQVLAAYAGEEANEWELDGTAAI 707
            E EP EIRL+S  DS   +DG   TRLWQNDV V G H  QVLA  YAGEEA+EWELDGTAA+
Sbjct: 543 AEGEPGEIRLSSADDSAALDGTTTRLWQNDVNVTGEHAQVLATYAGEEADEWELDGTAAV 602
```

Fig. 24 (sheet 4)

```
Query: 708 TRNTYGEGEAYFLGCDLGVSDLTRFVGGWLAARPQDGRQPEANLRSPASGVTSDVLHTVR 767
             TRN YG GEAYF+GCDL V+DLT+ V   +LAA  Q+                +DVLHTVR
Sbjct: 603 TRNPYGSGEAYFVGCDLDVADLTKLVRAYLAASSQE--------------NADVLHTVR 647

Query: 768 QSDDAIFDFYLTRGKSDVELRDIAGEPIVLFRAERGSDGGAYTVHRNGVLVMKR 821
             S  DA  FDFYL RGK   VEL+  I GEP++LF+  +R      G+YTV  RNGVLV++R
Sbjct: 648 ASADATFDFYLPRGKKTVELQGIEGEPVILFQTDREEKPGSYTVRRNGVLVVRR 701
```

Fig. 25 (sheet 1)

```
N-acetylmannosamine-6-phosphate 2-epimerase II (EC:5.1.3.9 COG3010)
Contig30 Gene 1561 - 64% >gi|50843444|ref|YP_056671.1| N-acetyl-
mannosamine-6-phosphate 2-epimerase [Propionibacterium acnes
KPA171202] gi|50841046|gb|AAT83713.1| N-acetylmannosamine-6-phosphate
2-epimerase [Propionibacterium acnes KPA171202]gi|67460804|sp|Q6A6A0|
NANE_PROAC Putative N-acetylmannosamine-6-phosphate 2-epimerase
(ManNAc-6-P epimerase)
       Length = 229

Score = 287 bits (734), Expect = 2e-76
Identities = 140/217 (64%), Positives = 167/217 (76%),
Gaps = 2/217 (0%)

Query: 7    VIERVKGGLIVSCQAYPGEPLRHPETMAQMAMAAVEGGAVGIRCQGLADIAAIKGQVDVP  66
            +I + GGL+VSCQAYPGEPLRHPETMAQMA A   GGAV +R QGL+D++A+KG+V VP
Sbjct: 8    IIASMAGGLVVSCQAYPGEPLRHPETMAQMAAAVEAGGAVAVRAQGLSDVSAVKGRVSVP  67
```

Fig. 25 (sheet 2)

```
Query:  67 VIGIWKDGSQGVYITPTLRHARCCAAAGADIVALDATGRPRPDGRTYAQTVQALHDE-GV 125
            V+GIWK+G  +G+YITPTLRHARC  +AAGAD+VALD T R R DG + A+T++ L  E  V
Sbjct:  68 VVGIWKEGDEGIYITPTLRHARCVSAAGADVVALDGTRRERADGLSLAETIERLKREYDV 127

Query: 126 TVMADCGSFDDARRAVDAGSDIISTTLSGYTGEREKTDGPDLELLEYMVSSFP-DTPVLC 184
            VMADCGS DD   A  +AG+D+I TTL GYTGER KTDGPD E++E  +V    D PV+
Sbjct: 128 VVMADCGSVDDGLFAAEAGADLIGTTLCGYTGERPKTDGPDYEVIEALVKKLDGDRPVIA 187

Query: 185 EGRIHTPEQLHDVMSRGAWAAVVGTAITHPTSITRWF 221
            EGRIHTP+Q    M   GA A  VVGTAITHPTSIT WF
Sbjct: 188 EGRIHTPDQARRAMDLGAHAVVVGTAITHPTSITGWF 224
```

Fig. 26 (sheet 1)

```
N-acetylneuraminate lyase 1 (EC:4.2.1.52 COG0329) Contig15 Gene 498 -
98% >gi|30172864|sp|Q8G527|DAPA_BIFLO Dihydrodipicolinate synthase
(DHDPS) gi|23465759|ref|NP_696362.1| dihydrodipicolinate synthase
[Bifidobacterium longum NCC2705] gi|23326445|gb|AAN24998.1|
dihydrodipicolinate synthase [Bifidobacterium longum NCC2705]
          Length = 301

Score =  578 bits (1491), Expect = e-164
Identities = 297/301 (98%), Positives = 298/301 (99%)

Query: 1    MSEHDMHLLEPAPFGRILPAMVTPMKSDGSVDFAAAQKLAKYLVADGADGLVVNGTTGES   60
            MSEHDMHLL+ APFGRILPAMVTPMKSDGSVDFAAAQKLAKYLVADGADGLVVNGTTGES
Sbjct: 1    MSEHDMHLLDSAPFGRILPAMVTPMKSDGSVDFAAAQKLAKYLVADGADGLVVNGTTGES   60

Query: 61   PVTHMDEKVELVRAVKEVVDVPVISGAGSNDTAHTVRMVEQTQEAGADAVLVVMPYYSRP  120
            PVTHMDEKVELVRAVKEVVDVPVISGAGSNDTAHTVRMVEQTQEAGADAVLVVMPYYSRP
Sbjct: 61   PVTHMDEKVELVRAVKEVVDVPVISGAGSNDTAHTVRMVEQTQEAGADAVLVVMPYYSRP  120
```

Fig. 26 (sheet 2)

```
Query: 121 SQDGIVGHYKAVDESAEKPIIVYDVPGRTGLKVKVETYDRLAGLEHVKAVKDATGDLAAA 180
           SQDGIVGHYKAVDESAEKPIIVYDVPGRTGLKVKV TYDRLA  LEHVKAVKDATGDLAAA
Sbjct: 121 SQDGIVGHYKAVDESAEKPIIVYDVPGRTGLKVKVGTYDRLAELEHVKAVKDATGDLAAA 180

Query: 181 VEKQQRTGLAWYSGDDGLFLPFLSIGAVGIISVIAHVASNPMQQLVQAFDRGDITTARRL 240
           VEKQQRTGLAWYSGDDGLFLPFLSIGAVGIISVIAHVASNPMQQLVQAFDRGDITTARRL
Sbjct: 181 VEKQQRTGLAWYSGDDGLFLPFLSIGAVGIISVIAHVASNPMQQLVQAFDRGDITTARRL 240

Query: 241 ANQLAPLVHALNGDGYQAVMAKAALKVKGVIPSTTMRLPNIGPDATQLDKAEEGMRAAGL 300
           ANQLAPLVHALNGDGYQAVMAKAALKVKGVIPSTTMRLPNIGPDATQLDKAEEGMRAAGL
Sbjct: 241 ANQLAPLVHALNGDGYQAVMAKAALKVKGVIPSTTMRLPNIGPDATQLDKAEEGMRAAGL 300

Query: 301 L 301
           L
Sbjct: 301 L 301
```

*Fig. 27 (sheet 1)*

```
N-acetylneuraminate lyase III (EC:4.2.1.52 COG0329) Contig23 Gene 827
- 61% >gi|50843445|ref|YP_056672.1| dihydrodipicolinate synthase
[Propionibacterium acnes KPA171202] gi|50841047|gb|AAT83714.1|
dihydrodipicolinate synthase [Propionibacterium acnes KPA171202]
         Length = 306

Score =  358 bits (920), Expect = 1e-97
 Identities = 186/301 (61%), Positives = 222/301 (73%),
 Gaps = 1/301 (0%)

Query: 3    QFRGVIPPVVTPLTADHRLDVESYRRSIDRMIAAGVNGLFVLGSSSEVVFSTDERRREIL  62
            +F  GVIPPVVTPLT +   LDV SY + I+R+I  GV+GLFVLGS+SEV F  DE R  +L
Sbjct: 4    KFHGVIPPVVTPLTPNGDLDVASYEKLINRLIGQQVDGLFVLGSTSEVAFFDDEMRGRVL  63

Query: 63   AAAIEIAGGRVPVLAGCIDTDTETNRVIEHARAAREMGAAAIVATAPFYALGGVAEIERHFR 122
            + A I  GRVP+LAG IDTET  RVI H   A E+G  A+VATAPFYA+ G  EIE HFR
Sbjct: 64   SEAKRIIDGRVPLLAGVIDTETLRVIRHIGQAEEIGVDAVVATAPFYAITGPTEIENHFR 123
```

Fig. 27 (sheet 2)

```
Query: 123 LIHAAVPELPLFAYDIPVCVHTKLPNDLLIRLGRDGVLAGVKDSSNDDVAFRFLIGDNEE 182
            +H A  +LPLF YDIPVCVH K+P DL+++LGR+GV+AG KDSS DDV+FR L    N
Sbjct: 124 ALHEAT-DLPLFVYDIPVCVHVKVPVDLMMKLGREGVIAGCKDSSADDVSFRRLALANRA 182

Query: 183 NGHPLTLLTGQEVVVDGAYMAGADGSVPGLANVDPYGYVAMWNAYRNGDWDSVRKEQNKL 242
            G PL+L TG EVVVDGA+M+GADG VPGLANVD   YVAM+ AYR  GDW+++VR EQ+K
Sbjct: 183 AGSPLSLFTGHEVVVDGAFMSGADGVVPGLANVDATSYVAMYKAYREGDWETVRIEQDKA 242

Query: 243 AALMRIVLAPSGVQGFGSGVGAFKTAMALLGVFDTNQMPEPVLALHGDNVKAIADVLRAC 302
            A LM I   AP GV G  +GVGAFKTAM LLG+ +TN M  P+  L  GDNV+ +A+VLR
Sbjct: 243 AELMEIAFAPQGVVGPAAGVGAFKTAMQLLGIIETNTMSVPLPTLTGDNVERVAEVLRRV 302

Query: 303 G 303
            G
Sbjct: 303 G 303
```

BIFIDOBACTERIAL GENE SEQUENCES AND THEIR USE

CROSS-REFERENCES TO RELATED APPLICATIONS

The present application is the U.S. National Stage entry of International Application No. PCT/US2007/020032, filed Sep. 14, 2007, which claims priority to U.S. Application No. 60/845,130, filed Sep. 15, 2006, the disclosures of each are herein incorporated by reference in their entirety.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

The adult human has about $10^{14}$ microorganisms that normally reside in the digestive tract called the gut flora or intestinal bacteria. The bacteria that make up the normal flora of the digestive tract have a symbiotic or mutualistic relationship with their human hosts by performing a variety of beneficial functions such as breaking down and aiding in the absorption of otherwise undigestible food, stimulating cell growth, repressing the growth of harmful bacteria, training the immune system to respond to pathogens, and defending against some diseases.

As an important example, without the gut flora, humans would be unable to break down and use some of the carbohydrates they consume, because some species of intestinal bacteria have enzymes that human cells lack for breaking down polysaccharides. As another example, intestinal bacteria play an important role in promoting the early development and later functioning of the gut's mucosal immune system. These bacteria stimulate lymphoid tissue associated with the gut mucosa to produce antibodies to pathogens. During this process, the immune system is trained to recognize harmful bacteria, while leaving helpful species of bacteria unaffected, a tolerance developed in infancy.

The human infant is born with a digestive tract essentially free of bacteria. However, soon after birth, bacteria begin colonizing an infant's digestive tract. The first bacteria to be established in the gut affect the immune response making it more favorable to their own survival and less favorable to competing species; thus the first bacteria to colonize the gut are important in determining the person's lifelong gut flora makeup.

Among the bacterial genera found in the gut are *Bacteroides, Clostridium, Fusobacterium, Eubacterium, Ruminococcus, Peptococcus, Peptostreptococcus, Bifidobacterium, Escherichia*, and *Lactobacillus*, among others. Among these species, *Bifidobacteria* are noteworthy because it has recently been found that this genera of bacteria is responsible for digesting unique oligosaccharides found in human milk. Estimates indicate that about 40-97% of these oligosaccharides pass through the human infant digestive tract undigested. It has been suggested that these oligosaccharides found in human milk serve as a prebiotic: a non-digestible food ingredient that beneficially affects the host by selectively stimulating the growth and/or the activity of one or a limited number of bacteria in the gastrointestinal tract. Thus, the one function of the oligosaccharides in human milk is to promote the colonization of the infant gut by beneficial bacteria such as *Bifidobacteria*.

Cow's milk and commercially available formulas, however, are lacking the oligosaccharides found in human breast milk. Because of the widespread use of cow's milk and commercially available formulas in the feeding of new born infants, it would be beneficial to provide infants with a source of human milk oligosaccharides which are lacking in these forms of nourishment. Other classes of individuals such as the elderly or patients treated with certain antibiotics and others who have compromised gut flora would also benefit.

BRIEF SUMMARY OF THE INVENTION

A first embodiment of the invention provides an isolated nucleic acid encoding a polypeptide involved in oligosaccharide modification that hybridizes under high stringency conditions to a sequence that can be SEQ ID NO: 1, 2, 3, 4, 5, 6, 7, 8, 9, 10, 11, 12, 13, 14, 15, 16, 17, 18, 19, 20, 21, or 22. In an aspect of the first embodiment, the invention provides an expression vector comprising a nucleic acid, which can be SEQ ID NO: 1, 2, 3, 4, 5, 6, 7, 8, 9, 10, 11, 12, 13, 14, 15, 16, 17, 18, 19, 20, 21, or 22 under the control of an expression control sequence. In another aspect of the first embodiment, a host cell comprising an expression vector as described above is provided, in which the host cell can be, e.g., *E. coli*.

A second embodiment of the invention provides polypeptides involved in oligosaccharide modification that have an amino acid sequence at least 90% identical to the amino acid sequence encoded by a nucleic acid that can be SEQ ID NO: 1, 2, 3, 4, 5, 6, 7, 8, 9, 10, 11, 12, 13, 14, 15, 16, 17, 18, 19, 20, 21, or 22.

In a third embodiment, the invention provides a method of synthesizing human milk oligosaccharides or oligosaccharide mimics by contacting an oligosaccharide containing precursor with a polypeptide of a sequence at least 90% identical to the amino acid sequence encoded by a nucleic acid that can be SEQ ID NO: 1, 2, 3, 4, 5, 6, 7, 8, 9, 10, 11, 12, 13, 14, 15, 16, 17, 18, 19, 20, 21, and 22 and then isolating a modified oligosaccharide containing precursor. In various aspects of the third embodiment, the oligosaccharide containing precursor can be a carbohydrate, a glycoprotein, or glycolipid. In other aspects of this embodiment, the oligosaccharide containing precursor has a terminal sialic acid, fucose, or N-acetyllactosamine. Furthermore, the oligosaccharide containing precursor can be plant, animal, or human derived.

A fourth embodiment of the invention provides a human milk oligosaccharide or oligosaccharide mimic derived by contacting an oligosaccharide containing precursor with a polypeptide of amino acid sequence at least 90% identical to the amino acid sequence encoded by a nucleic acid that can be SEQ ID NO: 1, 2, 3, 4, 5, 6, 7, 8, 9, 10, 11, 12, 13, 14, 15, 16, 17, 18, 19, 20, 21, and 22, and isolating the resultant modified oligosaccharide precursor. In various aspects of the fourth embodiment, a baby formula, baby food, or supplemented milk product containing the human oligosaccharide or oligosaccharide mimic is provided. The milk product of this aspect can be bovine or human derived.

A fifth embodiment of the invention provides a milk product enriched for human milk oligosaccharides or oligosaccharide mimics derived by contacting a starting milk product with a polypeptide of amino acid sequence at least 90% identical to the amino acid sequence encoded by a nucleic acid that can be SEQ ID NO: 1, 2, 3, 4, 5, 6, 7, 8, 9, 10, 11, 12, 13, 14, 15, 16, 17, 18, 19, 20, 21, and 22. In an aspect of this embodiment, the starting milk product is animal or human derived.

In a sixth embodiment of the invention, a method of promoting growth of *Bifidobacteria* in the gastrointestinal tract of a human by administering to the human a human milk oligosaccharide or mimic made by the methods of this invention is provided.

In a seventh embodiment of the invention, a method of promoting growth of *Bifidobacteria* in the gastrointestinal tract of an infant by administering to the infant a baby formula made by the methods of this invention is provided.

In a eighth embodiment of the invention, a method of promoting growth of *Bifidobacteria* in the gastrointestinal tract of a human by administering to the human the supplemented milk product of made by the methods of this invention is provided.

In an ninth embodiment of the invention, a method of promoting growth of *Bifidobacteria* in the gastrointestinal tract of a human by administering to the human the enriched milk product made by the methods of this invention is provided.

BRIEF DESCRIPTION OF THE DRAWINGS

FIG. 1 illustrates SEQ ID NO: 1 percent homology alignments across several different databases that represent protein sequence, protein domain and motif identifiers, as well as protein functional patterns.

FIG. 2 illustrates SEQ ID NO: 2 percent homology alignments across several different databases that represent protein sequence, protein domain and motif identifiers, as well as protein functional patterns.

FIG. 3 illustrates SEQ ID NO: 18 percent homology alignments across several different databases that represent protein sequence, protein domain and motif identifiers, as well as protein functional patterns.

FIG. 4 illustrates SEQ ID NO: 19 4 percent homology alignments across several different databases that represent protein sequence, protein domain and motif identifiers, as well as protein functional patterns.

FIG. 5 illustrates SEQ ID NO: 2 percent homology alignments across several different databases that represent protein sequence, protein domain and motif identifiers, as well as protein functional patterns.

FIG. 6 illustrates SEQ ID NO: 8 percent homology alignments across several different databases that represent protein sequence, protein domain and motif identifiers, as well as protein functional patterns.

FIG. 7 illustrates SEQ ID NO: 9 percent homology alignments across several different databases that represent protein sequence, protein domain and motif identifiers, as well as protein functional patterns.

FIG. 8 illustrates SEQ ID NO: 10 percent homology alignments across several different databases that represent protein sequence, protein domain and motif identifiers, as well as protein functional patterns.

FIG. 9 illustrates SEQ ID NO: 11 percent homology alignments across several different databases that represent protein sequence, protein domain and motif identifiers, as well as protein functional patterns.

FIG. 10 illustrates SEQ ID NO: 12 percent homology alignments across several different databases that represent protein sequence, protein domain and motif identifiers, as well as protein functional patterns.

FIG. 11 illustrates SEQ ID NO: 13 percent homology alignments across several different databases that represent protein sequence, protein domain and motif identifiers, as well as protein functional patterns.

FIG. 12 illustrates SEQ ID NO: 14 percent homology alignments across several different databases that represent protein sequence, protein domain and motif identifiers, as well as protein functional patterns.

FIG. 13 illustrates SEQ ID NO: 15 percent homology alignments across several different databases that represent protein sequence, protein domain and motif identifiers, as well as protein functional patterns.

FIG. 14 illustrates SEQ ID NO: 21 percent homology alignments across several different databases that represent protein sequence, protein domain and motif identifiers, as well as protein functional patterns.

FIG. 15 illustrates SEQ ID NO: 22 percent homology alignments across several different databases that represent protein sequence, protein domain and motif identifiers, as well as protein functional patterns.

FIG. 16 illustrates SEQ ID NO: 16 percent homology alignments across several different databases that represent protein sequence, protein domain and motif identifiers, as well as protein functional patterns.

FIG. 17 illustrates SEQ ID NO: 17 percent homology alignments across several different databases that represent protein sequence, protein domain and motif identifiers, as well as protein functional patterns.

FIG. 18 illustrates SEQ ID NO: 3 percent homology alignments across several different databases that represent protein sequence, protein domain and motif identifiers, as well as protein functional patterns.

FIG. 19 illustrates SEQ ID NO: 4 percent homology alignments across several different databases that represent protein sequence, protein domain and motif identifiers, as well as protein functional patterns.

FIG. 20 illustrates SEQ ID NO: 5 percent homology alignments across several different databases that represent protein sequence, protein domain and motif identifiers, as well as protein functional patterns.

FIG. 21 illustrates SEQ ID NO: 6 percent homology alignments across several different databases that represent protein sequence, protein domain and motif identifiers, as well as protein functional patterns.

FIG. 22 illustrates SEQ ID NO: 7 percent homology from alignments across several different databases that represent protein sequence, protein domain and motif identifiers, as well as protein functional patterns.

FIG. 23 illustrates the alignment of the protein encoded by SEQ ID NO:10 (SEQ ID NO:23) with the amino acid sequence of beta-hexosaminidase A from *Bifidobacterium longum* (SEQ ID NO:24). Consensus peptides=SEQ ID NOS:25-59.

FIG. 24 illustrates the alignment of the protein encoded by SEQ ID NO: 12 (SEQ ID NO:60) with the amino acid sequence of beta-galactosidase from *Bifidobacterium adolescentis* (SEQ ID NO:61). Consensus peptides=SEQ ID NOS: 62-94.

FIG. 25 illustrates the alignment of the protein encoded by SEQ ID NO: 17 (SEQ ID NO:95) with the amino acid sequence of N-acetylmannosamine-6-phosphate 2-epimerase from *Propionibacterium acnes* (SEQ ID NO:96). Consensus peptides=SEQ ID NOS:97-107.

FIG. 26 illustrates the alignment of the protein encoded by SEQ ID NO: 4 (SEQ ID NO:108) with the amino acid sequence of dihydrodipicolinate synthase from *Bifidobacterium longum* (SEQ ID NO:109). Consensus peptides=SEQ ID NOS:110-113.

FIG. 27 illustrates the alignment of the protein encoded by SEQ ID NO: 6 (SEQ ID NO:114) with the amino acid sequence of dihydrodipicolinate synthase from *Propionibacterium acnes* (SEQ ID NO:115). Consensus peptides=SEQ ID NOS:116-129.

DETAILED DESCRIPTION

Definitions

The term *Bifidobacteria* and its adjectives refers to a genus of anaerobic bacteria having beneficial properties for humans. *Bifidobacteria* is one of the major strains of bacteria that make up the gut flora, the bacteria that reside in the gastrointestinal tract and have health benefits for their hosts. See, e.g., Guarner F and Malagelada J R., Gut flora in health and disease. Lancet, 361, 512-519 (2003) for a further description of *Bifidobacteria* in the normal gut flora.

The term human milk oligosaccharide (HMO) refers generally to a number of complex carbohydrates found in human milk. Among the monomers of milk oligosaccharides are D-glucose (Glc), D-galactose (Gal), N-acetylglucosamine (GlcNAC), L-fucose (Fuc), and sialic acid [N-acetylneuraminic acid (NeuAc)]. Elongation may be achieved by attachment of GlcNAc residues linked in (β1-3 or (β1-4 linkage to a Gal residue followed by further addition of Gal in a β-1-3 or β-1-4 bond. Most HMOs carry lactose at their reducing end. From these monomers, a large number of core structures may be formed. Further variations may occur due to the attachment of lactosamine, Fuc, and/or NeuAc. See, e.g., Kunz, C. et al., Annual. Rev. Nutri., 20:699-722 (2000) for a further description of HMOs.

The term oligosaccharide mimic refers generally to any compound that is able mimic the physical, chemical, or physiological effects of complex carbohydrates found in human milk. Such effects may include, but are not limited, to serving as a carbon source or growth factor for microorganisms such as *Bifidobateria*, binding to receptors on cells, inhibition of bacterial cell binding to the mucosal surface of the gastrointestinal tract, promotion of development of the intestinal flora in infants, the elderly, or others with impaired intestinal flora, serving as a prebiotic nutrient, among other functions for HMOs known in the art.

A prebiotic or prebiotic nutrient is generally a non-digestible food ingredient that beneficially affects a host when ingested by selectively stimulating the growth and/or the activity of one or a limited number of bacteria in the gastrointestinal tract.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

General

The inventors have identified gene sequences that are associated with a bifidobacterial strain, *Bifidobacterium longum* bv. *infantis*. The gene sequences disclosed herein encode activities related to the catabolism of HMOs. Thus, the sequences of this invention encode proteins with the capacity to cleave and metabolize complex milk carbohydrates. Accordingly, these genes would provide a significant growth advantage to the cognate *bifidobacterial* strain for growth on milk oligosaccharides, or milk oligosaccharide mimics, and thus provide a means for selective *bifidobacterial* strain enrichment within animal gastrointestinal tracts. Among other uses, these gene sequences enable rationale screens for new *bifidobacterial* strains that can be selectively enriched through growth on milk oligosaccharides, or milk oligosaccharide mimics.

The proteins encoded by these gene sequences can also be used in the construction of HMO mimics by promoting the reverse reactions catalyzed by these catabolic enzymes. In particular, these enzymes can be used to synthesize particular oligosaccharide structures. For instance, once a complex oligosaccharide structure present in a biological sample, such as human breast milk, has been identified as having a beneficial use, these enzymes can be used to synthesize these structures from a variety of starting materials including lactose or other milk derived materials including simpler oligosaccharide structures or by decorating plant derived oligosaccharides.

Embodiments of the Invention

Gene Sequences Encoding HMO Catabolic Proteins

In view of the above, in one aspect, the present invention provides nucleic acids and their encoded proteins involved in the catabolism of HMOs. As demonstrated in greater detail below, a bioinformatics approach was used to identify gene sequences homologous to the sequences of genes known to be involved with oligosaccharide catabolism by searching a draft *Bifidobacterium longum* bv. *infantis* UCD272 (ATCC15697) genome sequence using the ClustalW program using known oligosaccharide catabolic genes as the query sequence. Genes (SEQ ID NO: 1-22) were identified based on their extent of homology to the known genes used as query sequences.

A number of programs are known in the art to determine extents of homology. Optimal alignment of sequences for comparison can use any means to analyze sequence identity (homology) known in the art, e.g., by the progressive alignment method termed "PILEUP" (see below); by the local homology algorithm of Smith & Waterman, Adv. Appl. Math. 2: 482 (1981); by the homology alignment algorithm of Needleman & Wunsch, J. Mol. Biol. 48:443 (1970); by the search for similarity method of Pearson (1988) Proc. Natl. Acad. Sci. USA 85: 2444; by computerized implementations of these algorithms (GAP, BESTFIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by Higgins (1988) Gene, 73: 237-244; Corpet (1988) Nucleic Acids Res. 16:10881-90; Huang (1992) Computer Applications in the Biosciences 8:155-65, and Pearson (1994) Methods in Molec. Biol. 24:307-31), TreeAlign, MALIGN, and SAM sequence alignment computer programs; or, by inspection. See also Morrison (1997) Mol. Biol. Evol. 14:428-441, as an example of the use of PILEUP. PILEUP, creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987). The method used is similar to the method described by Higgins & Sharp (1989) CABIOS 5: 151-153. The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

Another example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

Other useful programs, as shown below, include the EasyGene 1.0 server which produces a list of predicted genes given a sequence of prokaryotic DNA. Each prediction is attributed with a significance score (R-value) indicating how likely it is to be just a non-coding open reading frame rather than a real gene. The user needs only to specify the organism hosting the query sequence. Two more parameters (start codon leniency and R-value cutoff) have default values which may be altered if needed.

Another program useful for the practice of this invention is the FGENESB gene prediction algorithm (SoftBerry), based on Markov chain models of coding regions and translation and termination sites. The FGENESB program performs the following features: finds all potential ribosomal'RNA genes using BLAST against bacterial and/or archaeal rRNA databases, and masks detected rRNA genes; predicts tRNA genes using tRNAscan-SE program (Washington University) and masks detected tRNA genes; provides initial predictions of long ORFs that are used as a starting point for calculating parameters for gene prediction; iterates until stabilizes; generates parameters such as 5th-order in-frame Markov chains for coding regions, 2nd-order Markov models for region around start codon and upstream RBS site, stop codon and probability distributions of ORF lengths; predicts operons based only on distances between predicted genes; runs BLASTP for predicted proteins against COG database, cog-.pro; uses information about conservation of neighboring gene pairs in known genomes to improve operon prediction; runs BLASTP against NR for proteins having no COGs hits; predicts potential promoters (BPROM program) or terminators (BTERM) in upstream and downstream regions, correspondingly, of predicted genes (BTERM is the program predicting bacterial-independent terminators with energy scoring based on discriminant function of hairpin elements); and refines operon predictions using predicted promoters and terminators as additional evidences.

Synthesis of HMOs or Oligosaccharide Mimics (a) Cloning and Expression of Recombinant Proteins Encoded by HMO Catabolic Genes In another embodiment of this invention, methods for synthesizing human milk oligosaccharides or oligosaccharide mimics using SEQ ID NO: 1-22 are provided. Typically, the genes of this invention are cloned into expression vectors, and the proteins encoded by SEQ ID NO: 1-22 expressed, and the resultant proteins purified.

Standard methods in molecular biology and biochemistry can be employed to clone, express, and purify the proteins of this invention. Detailed descriptions of standard molecular biological methods techniques can be found, for example at Sambrook et al., *Molecular Cloning, A Laboratory Manual* (2nd ed. 1989); Kriegler, *Gene Transfer and Expression: A Laboratory Manual* (1990); and Current Protocols in Molecular Biology (Ausubel et al., eds., 1994)). In addition, kits for many molecular biological methods are commercially available.

To obtain high level expression of a cloned gene, the skilled artisan typically subclones the DNA sequence into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al., supra. Bacterial expression systems are available in, e.g., *E. coli, Bacillus* sp., and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the protein encoding nucleic acid in host cells. A typical expression cassette thus contains a promoter operably linked to the nucleic acid sequence encoding a monomeric subunit and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a monomeric subunit encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

(c) Purification of Proteins Encoded by HMO Catabolic Genes

Proteins and/or fragments thereof can be purified from any suitable expression system as described below. If desired, the protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra., Colley et al., *J. Biol. Chem.* 264:17619-17622 (1989); *Guide to Protein Purification, in Methods in Enzymology,* vol. 182 (Deutscher, ed., 1990)).

Recombinant proteins can be expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the expressed proteins from inclusion bodies. For example, purification of inclusion bodies typically involves the extraction, separation and/or purification of inclusion bodies by disruption of bacterial cells. The cell suspension can be lysed using 2-3 passages through a French Press; homogenized using a Polytron (Brinkman Instruments); disrupted enzymatically, e.g., by using lysozyme; or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity.

Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. One of skill in the art will recognize that optimal conditions for renaturation must be chosen for each protein. For example, if a protein is soluble only at low pH, renaturation can be done at low pH. Renaturation conditions can thus be adjusted for proteins with different solubility characteristics i.e., proteins that are soluble at neutral pH can be renatured at neutral pH. The expressed protein is separated from other bacterial proteins by standard separation techniques.

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a given protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

A protein can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

After the proteins encoded by the genes of this invention are cloned, overexpressed, and purified, they are subjected to assays for their activity that vary according to the particular function of the given enzyme. (See, e.g., the references cited in Example 1.)

The kinetic parameters associated with catalysis by each enzyme is determined in order to favor catalysis by these catabolic enzymes in the reverse direction, namely in the direction of oligosaccharide synthesis in order to generate HMOs and oligosaccharide mimics of the present invention. Because enzymes, in general, catalyze both the forward and reverse reactions depending of the concentrations of reactants and products, the skilled artisan can drive the reverse reaction in most cases by supplying a large concentration of a reaction product. (See, e.g., Tzortzis et al., *Appl. Microbiol. Biotechnol.*, 68: 412-416 (2005).) In the case of the enzymes of the present invention, the products used to drive the reverse reaction toward the synthesis of HMOs or oligosaccharide mimics include oligosaccharides containing end terminal sialic acid or fucose. The resulting oligosaccharides are used in a variety of applications as described below.

Uses of HMOS and Oligosaccharide Mimics of the Present Invention

The HMOs and oligosaccharide mimics of the present invention are used in a variety of applications. HMOs and oligosaccharide mimics can be administered directly to humans as a prebiotic food supplement to stimulate the growth of beneficial gut flora in individuals who have diminished numbers of beneficial bacteria in their gastrointestinal tracts. Examples of individuals in such need include infants, the elderly, persons with depleted gastrointestinal tract bacteria as a result of antibiotic therapy, chemotherapy, disease, or other causes.

One use of the HMOs or oligosaccharide mimics of the present invention is the supplementation of foods such as baby formula. Standard formulations for human baby formulas which can be supplemented can be found in the art, e.g., U.S. Pat. No. 5,902,617.

Other forms of administration of HMOs or oligosaccharide mimics includes the supplementation of animal milks, such as cow milk, which are normally lacking in HMOs.

EXAMPLES

The following examples are offered to illustrate, but not to limit the claimed invention.

Example 1

Identification of Genes Involved with HMO Catabolism

We received the *Bifidobacterium longum* bv. *infantis*UCD272 (ATCC15697) draft genome sequence from the Joint Genome Institute on Apr. 19, 2006 in 78 unannotated contigs. We began the in silico analysis by searching for genes whose presence we had predicted based on human milk oligosaccharide (HMO) utilization and known phenotypic traits exhibited by this strain. Specifically, we aligned previously determined sialidase genes from the phylum *Actinobacteria* (high G+C Gram-positive) of which *Bifidobacteria* are a member using the ClustalW program. This alignment yielded a nucleotide consensus sequence which was subsequently used to probe the 78 contigs for similarity utilizing bl2seq (NCBI). Contigs 69 and 77 exhibited significant similarity to the consensus sialidase and were segregated for further analysis. Gene models were created for these two contigs by FgenesB (Softberry Inc.) and the EasyGene Server 1.0 (Center for Biological Sequences Analysis) which determined potential ORFs and transcriptional orientation. The two gene models were analyzed against the non-redundant protein database at NCBI (genbank), the Pfam database, as well as Cognitor which all confirmed the presence of putative sialidase homologues. Translational start and stop were determined through further sequence analysis using the VectorNT1 (Invitrogen) suite of bioinformatic software.

Other genes of this invention were determined using methods analogous to the procedures described above. A gene model, trained on the previously sequenced *B. longum* bv. *longum* NC2705 genome, was predicted for all 78 contigs. BLASTP/Pfam was utilized to determine the potential function of each predicted ORF, in addition to known COGs in the Cognitor database (NCBI). Priority was given to identifying glycosyl hydrolases and enzymes that may be involved in the degradation and utilization of HMOs or constituents, as well as genes not found in known *bifidobacterial* sequences. These analyses yielded 22 genes involved in HMO degradation and utilization.

The extent of homology of the proteins encoded by the bifidiobacterial genes with known proteins from other species present in various databases known to involved with carbohydrate catabolism is shown in FIGS. 1-22 for each of the genes.

The functions of the proteins encoded by the gene sequences of this invention may be divided into 8 different classes which are described below.

Sialidase (EC:3.2.1.18 COG4409) is an enzyme which catalyzes the hydrolysis of alpha-(2->3)-, alpha-(2->6)-, alpha-(2->8)- glycosidic linkages of terminal sialic acid residues in oligosaccharides, glycoproteins, glycolipids, colominic acid, and synthetic substrates. Members of this family contain multiple BNR (bacterial neuraminidase repeat) repeats or Asp-boxes. The repeats are short, however the repeats are never found closer than 40 residues together suggesting that the repeat is structurally longer. These repeats are found in a variety of non-homologous proteins, including bacterial ribonucleases, sulphite oxidases, reelin, netrins, sialidases, neuraminidases, some lipoprotein receptors, and a variety of glycosyl hydrolases. See, e.g., Schauer, R. Sialic acids. Adv. Carbohydr. Chem. Biochem. 40 (1982)131-234.

Sialate O-acetylesterase (EC:3.1.1.53) acts on free and glycosidically bound N-acetyl- or N-glycoloyl-neuraminic acid; acts mainly on the 4-O- and 9-O-acetyl groups. This enzyme also acts on some other O-acetyl esters, both cyclic and acyclic compounds, which are not sialic acids. See, e.g., Shukla, A. K. and Schauer, R. High performance liquid chromatography of enzymes of sialic acid metabolism. Hoppe-Seyler's Z. Physiol. Chem. 363 (1982) 1039-1040.

N-acetylneuraminate lyase (EC:4.2.1.52 COG0329) acts on glycoloylneuraminate, and on O-acetylated sialic acids, other than 4-O-acetylated derivatives. N-acetylneuraminate lyase catalyzes the cleavage of N-acetylneuraminic acid (sialic acid) to form pyruvate and N-acetyl-D-mannosamine. The enzyme plays an important role in the regulation of sialic acid metabolism in bacteria. See, e.g., Comb, D. G. and Roseman, S. The sialic acids. I. The structure and enzymatic synthesis of N-acetylneuraminic acid. J. Biol. Chem. 235 (1960) 2529-2537.

N-acetylmannosamine-6-phosphate 2-epimerase (EC:5.1.3.9 COG3010) catalyzes the conversation of N-acyl-D-glucosamine 6-phosphate into N-acyl-D-mannosamine 6-phosphate. See, e.g., Ghosh, S, and Roseman, S. The sialic acids. IV. N-Acyl-D-glucosamine 6-phosphate 2-epimerase. J. Biol. Chem. 240 (1965) 1525-1530.

Beta-galactosidase (EC: 3.2.1.23 COG1874) catalyzes hydrolysis of terminal non-reducing beta-D-galactose residues in beta-D-galactosides. This class comprises a widespread group of enzymes that hydrolyze the glycosidic bond between two or more carbohydrates, or between a carbohydrate and a non-carbohydrate moiety. A classification system for glycosyl hydrolases, based on sequence similarity, has led to the definition of 85 different families. See, e.g., Kuby, S. A. and Lardy, H. A. Purification and kinetics of beta-D-galactosidase from *Escherichia coli*, strain K-12. J. Am. Chem. Soc. 75 (1953) 890-896.

N-acetyl-beta-hexosaminidase (EC:3.2.1.52 COG3525) catalyzes the hydrolysis of terminal non-reducing N-acetyl-D-hexosamine residues in N-acetyl-beta-D-hexosaminides. This class comprises a widespread group of enzymes that hydrolyze the glycosidic bond between two or more carbohydrates, or between a carbohydrate and a non-carbohydrate moiety. See, e.g., Isolation of beta-N-acetylhexosaminidase, beta-N-acetylglucosaminidase, and beta-N-acetylgalactosaminidase from calf brain. Biochemistry. 6 (1967) 2775-82.

Alpha-L-fucosidase (EC:3.2.1.51 COG3669) catalyzes the conversion of an alpha-L-fucoside+H2O=>L-fucose+an alcohol. See, e.g, Levvy, G. A. and McAllan, A. Mammalian fucosidases. 2. alpha-L-Fucosidase. Biochem. J. 80 (1961) 435-439.

Fucose dissimilation pathway protein (COG4154) is a protein linked to carbohydrate metabolism in *E. coli*. The gene for this protein is located in the fucose biosynthesis operon. See, e.g., Lu Z; Lin ECC., The nucleotide sequence of *Escherichia coli* genes for L-fucose dissimilation. (1989) Nucleic Acids Res., 17, 4883-4884.

Example 2

Glycosyl Hydrolase Activities in Strains of *Bifidobacteria*

This example describes experiments showing the presence of enzymatic activities corresponding to the nucleic acids and polypeptides of the present invention in strains of *Bifidobacteria*.

Methods and Materials

Glycosyl hydrolase assays. Assayed cells were incubated anaerobically at 37° C. on semi-synthetic MRS medium, with 1% (w/v) sterile filtered lactose or HMOs as the sole carbon source. Early stationary phase cells were harvested, and 200 mg of 0.1 mm diameter glass beads (BioSpec Products, Bartlesville, Okla.) were added to the suspensions which were subjected to two cycles of 45 s at a power of 6.0 m s$^{-1}$ on a Fast Prep FP120 cell disruptor (Qbiogene, Morgan Irvine, Calif.). The beads and cell debris were removed by centrifugation. Cell-free extracts were collected and kept temporarily on ice until the start of the enzyme assays. Protein concentrations were determined according to the Bradford method using bovine serum albumin as the standard. Activity of α-L-fucosidase (EC 3.2.1.51) and sialidase (EC 3.2.1.18) was assayed with the fluorogenic substrates, 4-mtheylumbelliferyl α-L-fucopyranoside, and 2'-(4-methylumbelliferyl) α-D-N-acetylneuraminic acid, respectively. Fucoasidase activity was assayed with a fluorogenic substrate concentration of 1 mM in 0.2 M phosphate-citrate buffer (pH 5.2), while the sialidase assay employed 0.5 mM of substrate mixed in equal volume with 50 µL of 0.25 M sodium acetate-acetic acid buffer (pH 4.3). The reaction mixture containing 100 µL of cell-free extract and 100 µL of substrate solution was incubated for 1 h at 37° C., and the reaction was stopped with 1.3 mL of 0.17 M glycine-carbonate buffer, pH 9.8. The fluorescence of enzymatically liberated 4-methylumbelliferone was determined in a Bio-Rad VersaFluor fluorometer (Eureka, Calif.) by excitation at 360 nm and emission measured at 460 nm. Serially diluted 4-methylumbelliferone was used to calibrate relative fluorescence units with substrate concentration. The specific activity of the glycosyl hydrolase was expressed as nanomoles of hydrolyzed substrate per milligram of protein per hour. Assays were performed in duplicates, and the standard error was reported.

Results

The catabolic activity of *bifidobacterial* strains in HMO metabolism was measured by monitoring sialidase and fucosidase activities required to deconstruct complex glycan structures. Enzymatic assays showed that *B. longum* bv. *infantis* has a 16.6- and 33.7-fold higher sialidase activity when grown on lactose as compared to *B. longum* and *B. breve*, respectively. (See Table 1.) These data suggest that *B.*

*longum* bv. *infantis* has an inherent and constitutive ability to process sialylated compounds. Furthermore, among the three strains tested, fucosidase activity was only present in *B. longum* bv. *infantis* and was only detected upon growth on HMO. As described below and elsewhere such catabolic activities may be reversed, thus assembling larger oligosaccharides from smaller ones (see, e.g., Tzortzis et al., *Appl. Microbiol. Biotechnol.*, 68: 412-416 (2005)).

TABLE 1

| | Sialidase (nmol/min/mg protein) | | Fucosidase (nmol/min/mg protein) | |
|---|---|---|---|---|
| | lactose | HMO | lactose | HMO |
| *B. infantis* ATCC 15697 | 10.8 ± 1.0 | 4.8 ± 0.7 | ND | 0.45 ± 0.04 |
| *B. longum* DJO10A | 0.65 ± 0.03 | NA | ND | NA |
| *B. breve* ATCC 15700 | 0.32 ± 0.03 | NA | ND | NA |

ND—Not detected
NA—Not available (not enough cell growth)

Example 3

Expression and Purification of the Proteins of the Invention and Synthesis of Oligosaccharide Mimics In order to utilize the genes of the invention, any of SEQ ID NO: 1-22 is cloned into an expression vector downstream of an inducible promoter using methods well known to those of skill in the art, such as the methods described herein. The gene in an appropriate expression vector is overexpressed in a suitable *E. coli* host. The resulting recombinant protein is extracted and purified using any number of established purification schemes known in the art. Because the purified enzyme is required to be native, the expressed protein is refolded if solubilized from an inclusion body. Characterization of the native protein involves a determination of reaction kinetics, specificity, and other biochemical features on carbohydrate substrate(s). Moreover, the reverse reaction is characterized (i.e., transferase activity) by assaying for enzyme activity in the presence of high molar concentrations of hydrolysis products (e.g., sialic acid). In order to optimize conditions for the reverse reaction, protein engineering is used to remove superfluous or inhibiting enzyme domains. Oligosaccharide construction can proceed de novo from soluble monomers, or from incomplete oligosaccharides isolated from plant or mammalian sources.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A purified alpha-L-fucosidase polypeptide comprising an amino acid sequence at least 90% identical to the amino acid sequence encoded by SEQ ID NO: 18.

2. A method of synthesizing human milk oligosaccharides or oligosaccharide mimics, the method comprising the steps of:
   (a) contacting an oligosaccharide containing precursor with the polypeptide of claim 1; and
   (b) isolating a modified oligosaccharide containing precursor.

3. The method of claim 2, wherein the oligosaccharide containing precursor is a carbohydrate.

4. The method of claim 2, wherein the oligosaccharide containing precursor is a glycoprotein.

5. The method of claim 2, wherein the oligosaccharide containing precursor is a glycolipid.

6. The method of claim 2, wherein the oligosaccharide containing precursor has a terminal sialic acid.

7. The method of claim 2, wherein the oligosaccharide containing precursor has a terminal fucose.

8. The method of claim 2, wherein the oligosaccharide containing precursor has a terminal N-acetyllactosamine.

9. The method of claim 2, wherein the oligosaccharide containing precursor is plant derived.

10. The method of claim 2, wherein the oligosaccharide containing precursor is human derived.

11. The method of claim 2, wherein the oligosaccharide containing precursor is animal derived.

12. The method of claim 11, wherein the animal is bovine.

13. The polypeptide of claim 1, wherein the polypeptide comprises the amino acid sequence encoded by SEQ ID NO:18.

* * * * *

UNITED STATES PATENT AND TRADEMARK OFFICE
CERTIFICATE OF CORRECTION

PATENT NO.         : 8,361,756 B2
APPLICATION NO.    : 12/441272
DATED              : January 29, 2013
INVENTOR(S)        : Mills et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 883 days.

Signed and Sealed this
Twentieth Day of August, 2013

Teresa Stanek Rea
*Acting Director of the United States Patent and Trademark Office*

```
                        SEQUENCE LISTING

<160> NUMBER OF SEQ ID NOS: 129

<210> SEQ ID NO 1
<211> LENGTH: 1185
<212> TYPE: DNA
<213> ORGANISM: Bifidobacterium longum
<220> FEATURE:
<223> OTHER INFORMATION: sialidase I, contig 23, gene 826

<400> SEQUENCE: 1
atgacggaga   acgggatgat   gaatacgaac   aatactgtgt   gcggcgcgaa   ccatgacgga      60
gcgatgagtc   tggcggcccc   aggcgattac   ggtgtggcct   gctaccggat   tccggccctt     120
gccgaggcgc   ccaacggctg   gatcctcgcg   gcgttcgacg   cgcggcccca   taactgccag     180
gatgccccgc   aagccaattc   gatcgtgcag   cgtatctcca   aagacggcgg   ccggtcattc     240
gagccgcagc   atgttgtggc   cgccgggcat   gatggcgtcg   acaaatacgg   gtattccgat     300
ccgtcctatg   tggtggaccg   gcagacggga   gaggtgttcc   tgttcttcgt   caaatcctat     360
gacgccggtt   tcggaacctc   ccaggcgggc   gtcgatccct   ctgcgcgtga   ggtgcttcaa     420
gccgccgtca   ccagttccat   cgacaatggc   gtgacgtgga   gcgagccgcg   catcatcacc     480
gccgacatca   cgaacagcga   atcatggatt   tcacggttcg   cttcttccgg   tgccggcatc     540
cagctcacgt   atggcgagca   tgcggggcgc   ctgatccagc   agtacaccat   caaggagctc     600
gacggccgct   accgtgcggt   atcggtcttc   tccgacgatc   acggtgcaac   ctggcatgca     660 ggcaccccg    tcggcgatca   catggacgag   aacaaagtcg   tggaactttc   cgatggccgt     720
gtgatgctga   actcgcgttc   ctccgatgga   aacggttgcc   gctatgtcgc   catctcccgg     780
gacggtggcg   ccacgtatgg   tccggtgatc   cgtgaaacgc   agctgcccga   tcccgagaac     840
aacgcgcaga   ttgcccgtgc   gttccccgat   gccccgagg    ggtcggcgca   ggccaaggtt     900
```

| | |
|---|---:|
| ctgctgtatt cctcctcgtc gccttcggac aggatcgatg gtctggtgcg cgtctcgatc | 960 |
| gatgacggca agacctggag tgccggccga cggttcacga cagggccgat ggcgtattcg | 1020 |
| gtgatcgccg cattgagcca caaggccggc ggcggctatg cctgctgta tgaaggtgat | 1080 |
| aataataaca ttatgtacac ccgtatctcg ctcgactggc tcaacggcca gctgaacgtc | 1140 |
| gacggaatcg gcggttttcc gctgtctggt gagggagggt gctga | 1185 |

<210> SEQ ID NO 2
<211> LENGTH: 2283
<212> TYPE: DNA
<213> ORGANISM: Bifidobacterium longum
<220> FEATURE:
<223> OTHER INFORMATION: sialidase II, contig 30, gene 1562

<400> SEQUENCE: 2

| | |
|---|---:|
| atggcagcat ccaacccgat cagctggtca cagcgaacat tcccctcacc cgaaggcacg | 60 |
| atcgcgtgca gattccgcgc acacgcggac ggccgcatct tcgatgccgt caatggatcg | 120 |
| gcgaatgacg cgccgctcct catatgcgcc atcgaacatg acgctctgcg cgtgcgcgcg | 180 |
| acgacgccac gacagcacgt cgatttcgac atcgaggaca cgacggggat agccgacggc | 240 |
| gccatgcaca cgttcgcgct cacattcggc gagttcggca cgcgcgtcta cctcgacggc | 300 |
| tcccagtgct tcagcggcac ggcgaacctg tgcccacga cgctcaccgg aaccgagggg | 360 |
| tcaggccaag gcgcgattcg cctcgcgggc ccgtccatcg acgtgaccga catgcgtctg | 420 |
| catgcaatcc ccctcacctc cgaaagcatc gccgccttga cgccgagacc cgcaccggac | 480 |
| atcgacttcg ccgcggccca gctcgccccg cgagatgtgc gccgcgtgcg cacgctacgt | 540 |
| tccggcacga tcttcatgca ttttcgtgtg cgcggacccc gccagtacgg cacgcttctc | 600 |
| gccgccggcg agcgcggcga ggaacgcctc gccgtctcga tcgacgacaa cggcatcacg | 660 |
| atgacggccg cggatggcct gtatgagcca tccacctacc atgcgcgcgg cgcatgggat | 720 |
| gacggccgat ggcatgatct gtcgattcgt tccgcgcgtg gcgccatcga catgtacgtc | 780 |
| gacggctggc acgaactgca tcaagcggga caggtgttct tcggcgactg gccgcaactg | 840 |
| gatgaggtgg ccatcgggca gaacacgaaa ggcgtcaggc tcatgggcga ggtgcgcaac | 900 |
| ggcggcgtct tcacgacccc gctcaccgac ggcgcgatcc gcaggctttc ggacgcaccg | 960 |
| gcgctaacga cgaccgcact gttcgacaag ggttaccacg gatccgtgag ttatcgcatc | 1020 |
| ccctcgatca tccgcacccc tcatggcgtg gtcgtcgccg gcgccgacca gcgcaccgcg | 1080 |
| attgcgaatg acgcgccgaa ccacatcaac ttcgtcatgc gcaggtcgct tgacggtggc | 1140 |
| cgcacctggc tcgacatgca gaccgtgatc gccaatccgg gcgaaggcgt cgacggcgcg | 1200 |
| tgcacaatcg actcatgtct tgtatgcgac gaacgcaatg gccgtctcac cgtcctcatc | 1260 |
| gaccgcttcg ccggcggcgt cgggttgccg aacaacacgc ccggcaccgg ggtcgaccgg | 1320 |
| cacgggcgac cgtgcctgta cgatcgcgca ggcacacgct atgtactcgc cgatgacggc | 1380 |
| acggtgcttg acgcggcgg cgagcgcacc ggataccggg tcgacgcgca cggcaacgtg | 1440 |
| acgcacgagg gacgggcctc gggcaacatc tacctcaagg agggcgctga ccccgacgaa | 1500 |
| tcactgctca tcgaacgcac gagcttcatc atcgaactgc attccgacga tgacggcgag | 1560 |
| acgtggagca caccacgcaa catcaaccac atgatcaagg aggattggat gcacttcctg | 1620 |
| ggcgtctcgc ccggcaacgg catccagctc caggcctccg aacatcgcgg gcgtctgctc | 1680 |
| gtcccgttct actgcaccgg cgcctcactc aagcattact cgggcggagc gctcatcagc | 1740 |
| gacgatggcg gcgacacatg gcgacgtggt tcgatgatca acgacggccg catcgtcaac | 1800 |

```
ggcaccgccg tcgacccgaa gaacatccgg gacgatgacg cgaccacgca cgaatccgtg    1860
ttcgtcgagc gcgcggatgg caccgtcgtg tgcttcttcc gcaaccagaa ccatgccggg    1920
cgcatcggcg tcgcgctcag ccacgacggc ggcgagacat gggatgacct gtacttcgac    1980
aaagacgtcc ccgacatctt ctgccaaccg aacgccgtgg cctgcgcgcc gcgatcggac    2040
acgatggtgt tcgcgaacgc aagccagatg ctgccgtatc gcggcaacgg ggtgctgcgg    2100
ctgagtctgg acgcgcacg cacatgggcg gcgcatcgct gcatcaaccc ctatcattac    2160
ggctatcagt gcatgacgat gctgccggac ggcgaactcg gattactctg ggagcgcgag    2220
accgcgggat tgtacttcac cacgctgccg ttgagcgtat tcggcgcggc cgaaacgcac    2280
tga                                                                  2283
```

<210> SEQ ID NO 3
<211> LENGTH: 1905
<212> TYPE: DNA
<213> ORGANISM: Bifidobacterium longum
<220> FEATURE:
<223> OTHER INFORMATION: sialidate O-acetylesterase, contig 15, gene 377

<400> SEQUENCE: 3

```
atgagcgcat caccacagac ggccaccggc ccagcacccg gcgccaacgc cagcggcgtg      60
gacgaaagcg cagccgaagc cgcacggaac aagccaatcg gcaccgccga gtttcggcct     120
tccgccatct tctcccatga catggtgcta aacgcggca agccaatcgt attgttcggc     180
accggcacgc ctggacggcc cgtcgtgacc gtgctgagca cggcagatgg cagcgcactg     240
attcgccgtc aatcatcgca ctccatcacg gacagtgtca gcaccatcgg atcgatcacc     300
ccggacggca cctggatggt tacgctaccg ccactggaag ccggtggacc gtacacgctg     360
accatctccg accgcaccag cgtaacgctt aagtacttta acgtcatggt cggcgaagta     420
tggattgcca gcgggcaaag caacatcgaa ttcgaactgc acaacgaccg tgatgcggat     480
tcggccatcg ccgcatccga tgatccgctg ctgcgcttct tcaatgtgcc caagttcggc     540
gtggtggaca cgcaacttat cgcggccgag aaccagtcgg cctggcgacc ctgctccccc     600
gattcctgca gcacgatgtc cgcaatcgcc tattatttcg cacgcaaact acggcgggac     660
ctgggacccg acgtaccggt cggtatcgtc gattgctata tcggcggtac gtcgatcacc     720
tcgtggatga gcgagcacat gctcaccgcc accgaggccg gcgcggcta tcttgaccgc     780 taccatcagc aaatcgacgg caaaaccgat cagcagttcc acgacgaaac cgactcctgg     840
caacgcacct ttaatgcgtg gaatgagcag atcgccgccg cacaggctgc agaaccggac     900
atcacgtggg atgtgctcga cgcccggtac ggcgagtgcc cgtggccgcc gcccgtcacc     960
ccgttctccc aatatcacgt caccggcgca ttcaacgcga tggtgcgccg gttggccccg    1020
ttctccacgc gcggcgtgct gtggtatcaa ggcgaagagg acgagcagcg gtacgcctcg    1080
tatcgcgaac tgctggggttg catgatcggt gaatggcggg cgttgtggag ccggcgcgca    1140
ggcggcgatt tcagtgatag ctacaatgtg ggacggatcg tcgccgatga tgccgcgcgc    1200
ggccacggtg ccgaaccaat cgccgacacg cctaccgcaa cggtcggaaa cgaggcggaa    1260
ctgccgttca tcatcgtgca attgccacgt tggatcgatc agaaggaata caacagtgac    1320
attgatcgca tgttctggcc tcatattcgc gaagcacaag ccgatgcagc acgtatcatt    1380
cccgacgtgt atctggcggt cacgttcgac accggcgagt tcaacaacat ccatccgacc    1440
gacaaacgtc cggttggcga gcgcatcgcg ttgcaagccg aagccatgt ctacgggctt    1500 cccgtccgcg ccgatggtcc cgtattcgtt tcgttggcat ccgctggcga aacggccgat    1560
```

```
gagctgcagg tgcgctttgg caacgccgac ggcctgcatt tcggaccgtg gtctgggagc    1620
gacgacgccg ggcacctatc ggcagttcac tcgtctggat ccggggaaac agaacccttg    1680
tggaccgtga atcgatgcga cgcggcggct tccggcttcg aaatcgctgg atcggacggc    1740
atctatcacc gtgcggacgc acggatcgag gccgataccg tggtgcttca tgccaacgcg    1800
gtatcgcatc cgatctgcgc acgttacggc tggttcagtt ggggcccggc accgctgttc    1860
aacgccttcg gcctgcctgc ggccccattc cggattcgca agtaa              1905

<210> SEQ ID NO 4
<211> LENGTH: 906
<212> TYPE: DNA
<213> ORGANISM: Bifidobacterium longum
<220> FEATURE:
<223> OTHER INFORMATION: N-acetylneuraminate lyase I, contig 15, gene
      498

<400> SEQUENCE: 4
atgagcgagc atgacatgca ccttcttgag ccagcacctt tcggccgcat tctgccggct     60
atggtcaccc cgatgaaatc cgacggcagc gtcgatttcg ccgccgcgca gaagctcgcc    120
aaatacctcg tcgccgatgg cgcggatggt ctggtggtca atggcaccac cggtgaatcg    180
cccgtcaccc atatggatga aaggtcgag ctggtcaggg ccgtcaagga ggtcgtcgac    240
gttccggtga tttccggcgc cggctccaac gacaccgcac acaccgtgcg tatggtcgaa    300
cagactcagg aagcgggcgc cgacgcggtg ctcgtcgtca tgccttacta ttcccgcccc    360
tcgcaggacg gtatcgtcgg ccactacaag gccgtcgacg aatccgccga aaagccgatc    420
atcgtctacg atgttcccgg ccgtaccggc ttgaaggtca aggtcgaaac ctacgaccga    480
ctggccggac ttgaacacgt caaggctgtc aaggacgcca ccggcgatct tgcagccgca    540
gtggagaagc agcagcgcac cggcctcgcc tggtattccg gcgatgacgg cctgttcctg    600
ccgttcctct ccatcggtgc cgtcggcatc atttcggtga ttgcccacgt cgcctccaac    660
cccatgcagc agcttgtcca ggcattcgat cgcggcgata tcaccaccgc ccgtcgcctc    720
gccaaccagc tcgccccccct tgtccacgcg ttgaatggcg acggttatca ggccgtcatg    780
gccaaggctg cgctcaaggt caagggtgtt atcccctcca ccaccatgcg tctgccgaac    840
atcggtcccg acgccactca gcttgacaag gctgaagagg gcatgcgcgc tgccggactg    900
ctgtaa                                                              906

<210> SEQ ID NO 5
<211> LENGTH: 897
<212> TYPE: DNA
<213> ORGANISM: Bifidobacterium longum
<220> FEATURE:
<223> OTHER INFORMATION: N-acetylneuraminate lyase II, contig 22, gene
      817

<400> SEQUENCE: 5
atgaccagca acgccatgtt cgaaggcgtg ttctgccccct ccatcaccat catgaacgcg     60
gacggaacca tagattacga caactggggc aagcacctcg accacctcgt cgacgcaggc    120
gtcgacggcg tgctgctgtt cggcagcatc ggcgaattct acgccatcga cgtcaagacg    180
aaggcggaag cggctcgctt cgccgtctcg aaggtcgccg gacgcatgaa ggtgctcgtc    240
ggcgtgggag acaccaacct ggacaacgtg aaggcgttgg cggcggaaag cgaagcggcc    300
ggagtcgacg cgctgctcgc cgtgtccccg tactatttcg gcccgtcccc ggattgcgcg    360
aaacggtact tctcggcggt ggccaaggcg acgaccctgc ccgtcatcct gtacaacttc    420
```

| | | | |
|---|---|---|---|
| ccggcccgaa | cgggcaacga | cctcacgccc gagctggtgg | ccgaactcgc cggcgagaac | 480 |
| ccgaacatcg | tcggcatcaa | agacaccgtc gacaccatca | gtcacaccag gaaggtcatc | 540 |
| gcggccgtcc | gcaaggtgaa | cccgtcgttc agcgtgctgt | ccggattcga cgaatactac | 600 |
| atcgtcaacc | ggatcagcgg | cggcaacggc gtgctgagtg | tctgaccaa cgtggaaccc | 660 |
| gagacgttcg | tcaaactgca | ccgcgcatgg gaggccggcg | accacgccgc ggtcgtcgaa | 720 |
| gcggccgagc | gcgtctccta | cctgatgcgc ctgtacgaca | ccgccgacct gttcatcagc | 780 |
| gccatcaagg | gcgcggtcaa | ggccaaggga ctacccatcg | acacgtccgt ccacgagccc | 840 |
| gccgtgcagc | tgaccgacga | gcagtatcgc accatccgcg | ccatcctgga caagtga | 897 |

<210> SEQ ID NO 6
<211> LENGTH: 957
<212> TYPE: DNA
<213> ORGANISM: Bifidobacterium longum
<220> FEATURE:
<223> OTHER INFORMATION: N-acetylneuraminate lyase III, contig 23, gene 827

<400> SEQUENCE: 6

| | | | |
|---|---|---|---|
| atgaatcagt | tcgtgggggt | cattcccccg gtcgtcactc | cattgaccgc ggatcatcgt | 60 |
| ctcgatgtgg | agagttaccg | gcgttcgatc gaccgtatga | ttgcggccgg ggtcaatgga | 120 |
| cttttcgttc | tcggatcctc | aagcgaagtc gtgttctcca | cggatgagcg acgtcgtgag | 180 |
| atactggccg | cggccattga | gattgccggc ggccgagtgc | cggtgctggc ggggtgcatc | 240 |
| gacacggaga | ccaatcgtgt | gatcgagcat gctcgcgcgg | ctcgtgagat gggagccgcc | 300 |
| gccatcgtgg | ccacggcgcc | gttctacgca ttgggcggcg | tggcggagat cgagaggcat | 360 |
| ttccgtctga | ttcacgccgc | ggtgcctgaa ttgccgctgt | tcgcatacga tatcccccgta | 420 |
| tgcgtgcata | ccaagctgcc | caatgatctg ctgatccgct | ggggcgtga tggcgtgctg | 480 |
| gccggggtga | aggactcgtc | gaacgatgat gtggcgttcc | gtttcctgat tggggacaac | 540 |
| gaggagaacg | gtcatccgct | gacgttgctg accggtcagg | aagtcgtcgt cgatggcgcg | 600 |
| tacatggccg | gcgcggacgg | cagcgtgcca ggcttggcca | atgtggatcc atatggctat | 660 |
| gttgcgatgt | ggaacgccta | ccggaacggt gattgggatt | cggtgcgcaa ggagcagaac | 720 |
| aaactcgccg | cattgatgcg | aatcgtcctg gcgccgtccg | gcgtccaggg attcggttcc | 780 |
| ggcgtgggcg | cgttcaagac | cgcgatggcg ttgctgggcg | tgttcgacac caaccagatg | 840 |
| cccgaaccgg | tgttggcgtt | gcatggcgac aatgtgaaag | ccattgcgga cgtgttgcgt | 900 |
| gcatgcggtt | tcgagcttgc | gcgcacggtg aacaggtcg | atgtgtccac cgagtga | 957 |

<210> SEQ ID NO 7
<211> LENGTH: 969
<212> TYPE: DNA
<213> ORGANISM: Bifidobacterium longum
<220> FEATURE:
<223> OTHER INFORMATION: N-acetylneuraminate lyase IV, contig 30, gene 1567

<400> SEQUENCE: 7

| | | | |
|---|---|---|---|
| atggcacagc | aattccacgg | cgtcattccg ccggcggtca | ccccgctcac cgcagaccag | 60 |
| gagctcgacc | tgccgagctt | cacccgctcg atcaaccgca | tgatcgacgc cggggtcaac | 120 |
| ggcatattca | cgctcggctc | gtcgggcgag gtcgcgttca | gcaccgatgc ccgccgcgag | 180 |
| gagatcattc | gcgcggcgat | tgacatcgtc gacggtcgtg | tgccggtgtt cgtcggctgc | 240 |
| atcgacaccg | aaacgaaccg | cgtgatcgaa catgcccgcc | aagcccgtga gctcggcgcg | 300 |

```
tcggcgatcg tcgcgaccgc gccgttttat gcgctcggcg gcatggccga agtcgaacgg    360
cacttccgtc tcatccacga ggcggttccc gatctgccgc tgttcgccta cgatattccg    420
gtgtgcgtgc acacgaaact gcccggcgac atgctcgtgc gtctgggact cgacggcgtt    480
cttgcgggcg tcaaggattc ctcgaacgat gatgtctcgt tccgtttcct ggtcgatgac    540
aacaacaagg cgggccatcc gctgacgctg ctcaccgggc aggaggtcgt cgtcgacggc    600
gcctacatgg ccggcgcgga cggctccgtc cccggactcg cgaatgtgga ggcgaccgca    660
tacgtgcgca tgtggaacgc ctaccggaaa ggcgattggg gttccgtgcg caccgaacag    720
gacaagatgg cggcgctcat gcgcatcacc agcgtcgtgc agggtgtgca ggggttcggc    780
gccggcgtcg gcgcattcaa gacggcgctc gcgttgctcg gcgtcttcga tacgaaccag    840
atgcccaatc cggtcgcgcc gctcgccggc gagaacgtcg aacgcatcgc cgcggtgctt    900
aaggactgcg gactgccgct cgctcgcacg ccactcgaag tgagcgaatc caccgccgtc    960
aagggctga                                                            969

<210> SEQ ID NO 8
<211> LENGTH: 1956
<212> TYPE: DNA
<213> ORGANISM: Bifidobacterium longum
<220> FEATURE:
<223> OTHER INFORMATION: N-acetyl-beta-hexosaminidase I, contig 23, gene
      833

<400> SEQUENCE: 8
atggtgcagg aaccaacatt ggaatggcat gtcataccgg agccgacgaa tgtcgagccg     60
ctggtgggaa catgctcgtt gccgttgtcg ggaacggttg tggagcaacg aggtgcggat    120
gatgcggagg ccgtgtttgc gcgtcagctt gtcgacgaca ttaagcgcgt gtgcggaggc    180
cgctggcagg tggcctccgg agaggttcag cgggaggtga cttgcggac cagtccttcg    240 ctcgatgact ggtcgtacgt gcttgaggtc tcgccgacg gcgttgtgat cactggttcg    300
gggttcgaag gcgttcgcga tggcgtgcag acattgcgtc agattattcg ccagattggt    360
ttgacgatac cgtgcatggt catcagggat cggccggcgt tctcgacccg cggttactat    420
ctggacgtga ctcgtggccg tgtgccctct atggcttggc tgaaatcgtg ggtggatcgc    480
ctgtgcttct acaagtacaa ccaattccag ttgtacatcg agcatacgtt ccagttcaat    540
ggtcttagcg aagtgtggcg tggcgccgat ccgttgactt cgtccgacat tctcgagctt    600
gattcctatt gcgcggcgcg tggcatagag ctcgtgccct ccgtgtcgac gttcggacat    660
cattacaccg cgctgcggac gcggcaacta cgtgatctgg gagagtttcc ggaggacgcg    720
gatcgtcctt tcagcctgat cgagcgaatg acgcaccata cgctcaacat caccgatgag    780
cggtcctatg agttttcgac atcattgatc gatgagctga tgccgttgtt ccgttcgcgg    840
aagttcaata tctgcgccga tgagacgttt gatctcggca aggggaggtc gaagcaggaa    900
tcggcgaaac gtggcgttgg cgcgatgtat gccgatttcg tcgagcgact gtgccgccat    960
gttgatgatc gtgggcatga tgtcatggtg tgggccgatg tcgcgctcga gcaccctgag   1020
atcatcgata cgcttcccaa gaacatcacc tggctgaatt ggcagtatga gcccaacgtg   1080
gatgatggca caacggcagc tctcgccgat gccggcgcga cgcagatggt gtgcccggcg   1140
gtgtggtgct ggaatgcgct gattccgcgg atcgacgatg cgtggaataa catcaccagg   1200
atggcgcgcc atggccgcgc ccatgatgtt tcggggatgc tggtcactga ttggggggat   1260
ttcggacacg tcaacgatcc ccgcatgtcg gttccgggca tgatcttcgg tgcgcagcaa   1320
tcctggaatc cggatgccga gctcagcgaa gtcgatatgc tgtcgcgcat atccaccatc   1380
```

```
gaatacggcg accatactgg tagcgtggtc ggtgcgctca ggggcgcttc tgccaaaggc    1440
ggattctcgt ggagcgatct cgtcacctat ctggaactgg acgacggccg tggcggatgc    1500
aatacggaga tcgtgcgggt catgggctgt ctggaagcgt atcggaatga tttgccgcag    1560
tccggtcagg caaggttggc ggatgctcgc gtttcgatgc tgcggacgtt gcgtgactcc    1620
attctcgcgg gccgggaatt gaacggcaag cttgacgatg cagccaagga tatcacccag    1680
ctgctccgcg tggccggtga tccctcctcc gctgcggtct ggtcgttggc catcgacggt    1740
cagcgtctgc tgaaccgtgt cgggttggcg ttgttggccg cgcatggcgt ggtgcggcag    1800
gatgaggccg gaatcgatgc ggcgaagctg gccgatgaac tggaatgctg gaccgaacag    1860
tattcgaggc tctggcatga ggtcagtcgg cagtcggaac tggcccgcat ccaacacgtg    1920
gtatggcgcg cggcggacgt gctgcgttcc atttag                              1956
```

<210> SEQ ID NO 9
<211> LENGTH: 2022
<212> TYPE: DNA
<213> ORGANISM: Bifidobacterium longum
<220> FEATURE:
<223> OTHER INFORMATION: N-acetyl-beta-hexosaminidase II, contig 30,
      gene 1414

<400> SEQUENCE: 9

```
atgagcgatc aagcaaccct gaagggatgg accatcatcc ccacgccgca aaccatgcag     60
cataaagcga acatcgcatt gctgccaatg tgcggacgaa tcaacgaagc gcgcgcagtc    120
ggtgacgatc ggcacatact tgccgtgcag ctcatcgacg catccgcgc agccaccgga     180 ttggaatggg atatcgccac cggcgaccgc tggccgggat tcatcacctt gacgaccttt    240
gacgaccccc atgcacaccc gtccggtgca tatacgctcg atgtcacccc ggacggcgtg    300
accgtagcgg gagcggattt cgagggtgtg cgtaacggcg tgcagacttt acgccagctc    360
atccgccaat gcgcgccgc cctgccctgc ctgcacatcg aggaccgacc cgccttcgaa    420
acgcgcggct actacctcga cgtcacccgc gggcgcgtcc ccaccctcga ctggctcaaa    480
cactgggcca caagctctg cctgtacaaa tacaaccagc tccagctcta atcgaacac     540 accttcgcgt tcgactcgat gagcgagacc tggcgcggtt ccagcccgct caccccgcgc    600
gacatcctcg cattcgacga ctactgcgcc gagcgcggca tcgagctggt cccgtcggtc    660
tccacgttcg acacctcta catggccctg cgcacgcaat ccctgcgcga cctcggcgag    720
ttccccgaaa ccgccgacga gccgttcggg ttcatcgacc gcatgcacca ccacacattg    780
aacatcggcg acgaccgcgc cttcgccctg tcgtgccggc tcatcgacga ctacctgcaa    840
ctgttccgct ccaacaaatt caacatctgc gccgacgaga ccttcgacct cggcaagggc    900
cggtccaagc cctcgccga ccgcatcggc gtcgcggcca tgtacgccga ctacgtcacc    960
cgcctgtgcc gccacctcga agcccagggc aggcggccga tgatgtgggg cgacatcgcc   1020
ctcgaacacc ccgagatcct cgaccggctc cccgaaaccg tcaccctgct caactggcag   1080
tacgaccctc aggtcacgga cgagaagatc cacaccgtcg ccgaatccgg tgccaagcag   1140
atcgtatgcc cggccgtatg gtgctggaac gcgctcctgc cgcgcatcga cgacgcctgg   1200
agcaacatca cccgcatggc ccgctacggc aggcaatacg cgcccaggg catgctcgtc    1260 accgactggg gcgacttcgg ccacgtcaac gacccacgca tggccatccc cggcatgatc   1320
atcggtgcac aggaatcatg gaacccgagg cgaatcccgg atgaggccga catgctccgc   1380
cgtatctccc gactcgaata ccacgacgcc agcggtgaac tgcttaatat tcttacgcat   1440
```

-continued

| | | |
|---|---|---|
| gcaagtcatg cggccagttt cgaatggaac cacctgatca cttggctgga acttgatgac | 1500 |
| ggacaaggcg gagtcaacac cggggtcctg caaaccatcc cgggactgct gccggaaaac | 1560 |
| gaacgaccgg acgatgtgat ccgttccctc cagaacgaaa gcaagacacc gtcacttgcg | 1620 |
| gaatcccgac gaatgctgct ccgctatctg aaacaccgca tcacgctcgg cgaaaccgca | 1680 |
| gatcaccttc tgcaggccag tgcccgtcga atctccgcga tcaccgcgac cgcaggaccg | 1740 |
| cggaacgcag gaaacgccgc tgcattccgc atagccgtcg agggacaacg actgctgaac | 1800 |
| cggggttggcc tccggcttgc gtccgagacc gggatcactg acactttgca accgaacacc | 1860 |
| acgtctcaac ataacgatga ggcgaacctt gctgaagcat tggagatctg gatgaggcg | 1920 |
| tatgcgacgc aatggagcac ggtcagccga gactccgaac tccgtcggct gcaagatacg | 1980 |
| gtgcgggagt taacggacca tctgcgcttc caatccgtct ga | 2022 |

<210> SEQ ID NO 10
<211> LENGTH: 1956
<212> TYPE: DNA
<213> ORGANISM: Bifidobacterium longum
<220> FEATURE:
<223> OTHER INFORMATION: N-acetyl-beta-hexosaminidase III, contig 30,
      gene 1639

<400> SEQUENCE: 10

| | | |
|---|---|---|
| gtgcccactt ccgaacataa ggccgacgac gcaacgcggc atcttaccct gattcccgct | 60 |
| ccggtgacat tggagtacac ccatggtacg gctttgatcg gtcctctggt gacgatcgag | 120 |
| gatgccgatc agtcttggga gacgttgccg atcgagcagc tgtccgacga acttcggcac | 180 |
| cgctacggcg tcaccgtcct gaggcgccgc acacacggca ccgtcatatc cctgggcctg | 240 |
| gattcacggc tggcccatga cgaatacacg ttggatgtgt ccgaatcgga gggcatccgt | 300 |
| gtgcgtggcg gcggcgaaag cgggctgcgg tacggtctgc agacgctgcg gcagatcatc | 360 |
| gggcagacct cgcgtgccat tccctgcctg catatccaag acaagcccgc gttcgcggtg | 420 |
| cgcgcctaca gtctcgacgt gacacgcgga cgagtgccga cgatggagtt cctcacctgg | 480 |
| ttcgtcgacc agctggcctt atataaatac aatcagttcc agctgtatgt cgagcatgcc | 540 |
| ttcgcgttcg tcgagctcag cgaggcgtgg cgcggcaccg atccgctcac ggccgccgac | 600 |
| atcacgtatc tggacgagta ctgcgcgcgt cgcggcatcg agttggtgcc gtcgttggcc | 660 |
| acgttcgggc acatgtacat gaatctgcgc acccgtgagc atcgcgggct gggtgagttt | 720 |
| cccgaagacg ccgaccgccc gttcagcttc atcgaacgca tggagcatca cacgctgaac | 780 |
| gccgccgatc ccaaggccca tgatttcgcc tcgcgcctga ttgaggaata cgcgccgctg | 840 |
| ttccgttcga agtccttcaa tatcggcggc gatgagacgt tcgacttggg acgtggcagg | 900 |
| tccgcgcagg acgcgccgga agccggccgc gatgaactgt atgccggttt cgtcagggat | 960 |
| ttgtgcgaaa cgcttgcccg tcatggtcgg caaccgatgt tgtgggcgga catcgcgctc | 1020 |
| gaaagcccgc gcacgatgga tctgctgccc ggcgacatca cgatgctcaa ctggatgtac | 1080 |
| gagccgcaga tcgacgagag caagatccag accatcgcca cgcagggccg tcgacagttc | 1140 |
| gtgtgccccg cggtgcgggc ttggagccgg ttcttccccg attatgcggg tgcctggctg | 1200 |
| aacacgtatc acatggcgtt ggcggggacc aagtacgatg cggaaggcat ggtggtcacc | 1260 |
| gattggggtg attatggcca tgtcaacgat ccgcgtctga gcgtgccggg cctgtgctat | 1320 |
| ggcgctcaga acgcttggaa tccgatcgag atcgatgcgc atgagatgaa ccgtcgaatc | 1380 |
| tccgctctgg tgtatggcga cgaatccggt cgcatcatgg attgcctcgc cgcatcgac | 1440 |
| tccgatgggg tgtcattccc ctgggacctt gccgtgcagg tgctggagct ggaatacggt | 1500 |

```
tccggcaccg gcgcgctgaa catggatgtg gcggcgtgca tggaacgttc gagcggcgga    1560
aagctcacgc tggaccgcac attgggatgc gatgacgcgc gccggcggat gctccagtgg    1620
aaccgcgagc gtatcgaacg gcgtcgggat tgcgatcagg tgctgcgtga ctgcggcgac    1680
gcgttcgccg gtctagacaa gggaggcctg accgcggagt tcctgtcggt gatgctggac    1740
gggcagcgac tgttcaacga acttggcgag gaactgctgg cgttggccga cggcaaggac    1800
gtcggcagcg gggcgaatcg tctcgccgcc gatctggagt tgtggttcga gcggtatcgc    1860
gcacagtggc tgtcggtcgg acggcatgcc gagctcgcac gtatcgccca cgtggtgtgg    1920
tctctcgcgg acattctgcg tagggcgct ctgtaa                              1956

<210> SEQ ID NO 11
<211> LENGTH: 2076
<212> TYPE: DNA
<213> ORGANISM: Bifidobacterium longum
<220> FEATURE:
<223> OTHER INFORMATION: beta-galactosiidase I, contig 15, gene 480

<400> SEQUENCE: 11
atggaacata gagcgttcaa gtggccgcag ccacttgcgg gcaacaagcc ccgcatctgg      60
tacggcggcg attacaaccc cgaccaatgg cctgaggaag tgtgggacga agatgtagcc     120
ctcatgcagc aggccggcgt caacctcgtc tccgtagcca tcttctcctg ggccaagctt     180
gagcccgaag aaggcgtgta cgacttcgat tggctcgacc gcgtcatcga caagctcggc     240
aaggccggca tcgccgtcga tctcgcctcc ggcaccgcat cccgccgat gtggatgacc      300 caggcccacc cggagatcct ctgggtcgac taccgcggcg acgtctgcca gcccggtgcc     360
cgccagcact ggcgcgccac cagcccggtc ttccttgact acgcgctcaa cctgtgccgc     420
aagatggccg agcactacaa ggacaacccc tatgtggtct cttggcatgt gagcaacgag     480
tacggctgcc acaaccgctt cgactattcc gaagacgccg agcgcgcctt ccagaagtgg     540
tgcgagaaga agtacggcac catcgacgct gtcaacgacg cctggggcac cgccttctgg     600
gcgcagcgca tgaacaattt ctccgagatc atcccgccgc gattcatcgg cgacggcaac     660
ttcatgaacc cgggcaagct gcttgattgg aagcgtttca gctccgacgc gctgctggac     720
ttctacaagg ccgagcgcga cgccctgctc gagatcgccc caagccgcaa gaccaccaac     780
ttcatggtct ccgcgggctg caccgtcctc gactacgaca agtggggtca tgacgtggac     840
ttcgtgtcca acgaccatta cttctcgccc ggcgaggccc acttgacgca gatggcctac     900
gcggcctgcc tcaccgacgg catcgcccgc aagaacccgt ggttcctcat ggaacattcc     960
acgtccgccg tcaactggcg cccgaccaac taccggctcg agcccggcga gctggtgcgc    1020
gactccctgg cccatctggc catgggcgcc gacgccatct gctacttcca gtggcgtcag    1080
tccaaggccg gcgccgagaa gtggcattcc gccatggtgc cccacgcagg cccgactcc     1140 cagatcttcc gcgatgtgtg cgagctgggt gccgacctca caagcttgc tgacgagggc    1200 ctgctgagca ccaagctggt caagtccaag gtcgccatcg tcttcgacta cgagtcccag    1260
tgggccaccg agcacaccgc cacccccacg caggaggtgc gccactggac cgagccgctg    1320
gactggttcc gcgcgctggc ggacaatggc ctgaccgccg acgtggtgcc ggtccgcggt    1380
ccttgggatg agtacgaggc cgtcgtgttg ccgagcctgg ccatcctgtc cgagcagacc    1440
acgcgccgcg tgcgcgagta tgtggcgaac ggcggcaagc tgttcgtgac ctactacacc    1500
ggtctggtgg acgacaggga tcacgtctgg ctggcggct accccggctc cattcgcgac    1560
gtggtgggcg tgcgcgtcga ggaattcgcc ccgatgggca ccgacgcccc cggcaccatg    1620
```

```
gaccaccttg acttggacaa cggaaccgtg gcgcacgatt tcgccgacgt gatcacctcc    1680
gtggccgata ccgctcacgt ggtcgcctcc ttcaaggcag ataagtggac cggtttcgac    1740
ggcgctcccg ccatcaccgt caacgacttc ggcgacggca aggccgcata cgtcggtgcc    1800
cgtctcgggc gtgagggctt ggccaagagc ctgcccgcgc tgctggagga actcggcatc    1860
gagacttcgg ctgaggacga tcgtggtgaa gtgctgcgcg tcgagcgtgc ggacgaaact    1920
ggcgagaacc acttcgtgtt cctgttcaac cgcacccacg atgttgcggt cgtggacgtg    1980
gaaggcgaac cgctggtcgc ctcgctggcc caggtcaacg agtccgagca cacggccgcc    2040
atccagccca acggcgtact cgtcgtcaag ctgtaa                              2076
```

<210> SEQ ID NO 12
<211> LENGTH: 2481
<212> TYPE: DNA
<213> ORGANISM: Bifidobacterium longum
<220> FEATURE:
<223> OTHER INFORMATION: beta-galactosiidase II, contig 18, gene 584

<400> SEQUENCE: 12

```
gtgcacaacc tgtcgacgag cgagcggcca gtagttgggt ccgatgcaga gcccacggta     60
ctggttgctc gctcgtcgaa tcaaagtcac gtcgacgctt ttctacgttt ccggtacgtc    120
tacgtttccg gtatgttcat catgataaca gcaattcttt ccctgaccga ctccatcgag    180
tatggtcagg aagatcggca agtcagaggg gccggaaccg gcggtgtgtc gcctatcggc    240
caggagtgtc catcagctag tatccggctgg tatccgatat gggccgtggc cctgcgccac    300
ctgccaaagg aggtaatcgt gcgtgcgcga cgtgacttcg catggccaaa actgctgacc    360
gcggacggac gcggcatcgc cttcggcggc gactacaatc ccgaccaatg gccggaggac    420
gtctgggatg acgacatccg cctgatgggc caggccggcg tcaacaccgt ggcccttgcc    480
atcttcagct gggatcgcct ccagcccacc gaagaccatt ggaatttcga ctggctcgat    540
cgcatcatcg acaagctcgg ccaggccggc atcgcggtcg atctggcatc cgcgacggcg    600
accgcgcccc tgtggctcta cgagaaccat cccgaggttc ttccgcgaga caagtacggt    660
cacccggtca acgccggttc gcgccaatcc tggagcccga ccagcccggt gttcaaggaa    720
tacgcgctaa ccctatgccg caaactcgcc gaacgctacg gcaccaaccc gtatgtgacg    780
gcatggcata tgggcaacga atacgggtgg aacaaccgcg acgactactc cgacaatgcg    840
ctcgaagcct tccgcgcatg gtgccgccgc aagtacggca ccatcgacgc gctcaaccaa    900
gcgtggggca ccacgttctg gggacaggag atgaccggtt tcgacgaagt cctcatccca    960
cggttcatgg gcgccgactc gatggtcaat cccggtcaga agcttgattt tgaacggttc   1020
ggcaacgaca tgctgcttga cttctataag gccgaacgtg acgcgatcgc cgaaatctgc   1080
cccgacaagc cgttcaccac gaacttcatg atctccaccg accaatgctg catggactac   1140
gccgcttggg cggaggaagt gaatttcgtg tcgaacgacc actacttcca cgaaggcgag   1200
tcccacctcg acgagctggc ctgttccgac gcgctcgtgg attcgctggc gctcggcaaa   1260
ccatggtacg tcatggaaca ttccacttcg gcggtgcagt ggaaacctct gaacacccgc   1320
aaacgcaacg ggaaacggt gcgcgactcc ctggcccacg tggccatggg cgccgacgcc   1380
atcaacttct ccaatggcg cgcatccgcg ttcggcgccg aagcgttcca ttccgccatg   1440
gttccgcacg ccggcgagaa cacgaaactg ttccgtcagg tatgcgaact gggcgcgacg   1500
ttgcaagcgc tcgccgatgc cggtgtccaa ggaagcgaat ggcgcatgc ggacacggcg   1560 atccttttca gcgccgaatc ggagtgggcc acccgctccg agacgttgcc gagcatgaaa   1620
```

```
ctcaaccatt ggcatgacgt gcgtgactgg taccgcgcgt tcctgaacgc gggtgcccgc    1680
gccgacatcg tgccgcttgc ctacgattgg agttcataca agaccatcgt cctgccgacc    1740
gtgctgatgc tgagcgacgc cgatacgcga cggctggccg gtttcgtaca ggacggaggc    1800
cgcgtggtgg tcggttacgc gaccggcctg ctcgacgagc gcttccacac gtggctcggc    1860
ggataccccg gtgcgggcga tggactgctg cgctcgatgc tgggcgttcg tggcgaggaa    1920
ttcaacattc tcggtaccga gacggaagac gagccgagcg agattcggct ggcatccacc    1980
ggggattcgc ccacgatgga cggtgccgtg acccgcctgt ggcagaacga cgtgaccgtc    2040
gccggaccgc atgtgcaggt gcttgccgcg tatgccggcg aagaagcgaa tgagtgggag    2100
cttgacggca cggccgcgat cacccgcaac acgtacggcg aaggggaggc gtatttcctc    2160
ggctgcgatc tgggcgtgag cgatctgacg cgattcgtgg gaggctggct tgccgcgcga    2220
ccacaggatg gccggcagcc ggaagccaac ctgcggtcgc cgccagcgg cgtgacctct     2280 gacgttctgc acaccgtgcg tcaatccgac gacgccatat tcgacttcta tctgacacgt    2340
ggcaaatcgg atgtcgaact gcgcgacatc gccggggagc cgatcgtcct gttccgggcg    2400
gaacggggca gtgacggcgg cgcgtatacg gtgcatcgca atggcgttct cgtgatgaaa    2460
cgcccgaacc cgtcggtgta g                                              2481

<210> SEQ ID NO 13
<211> LENGTH: 2121
<212> TYPE: DNA
<213> ORGANISM: Bifidobacterium longum
<220> FEATURE:
<223> OTHER INFORMATION: beta-galactosiidase III, contig 23, gene 887

<400> SEQUENCE: 13
atgaccgaca ccatggcaca cacccaaccc gcatcacccg catcaccgc atcgcctgca      60 ccgaccatca ccgcaccggg cggccgcttc gtcttcggcg cgactggaa ccccgagcag     120 tgggacgaat ccacctgggc ggacgacatc gccaaactcg aacgcgccgg catcaacgag    180
gccaccatca acgtgttctc ctgggcgctg atccagccgg acgagagccg ctacgacttc    240
gccatgctcg accgcatcgt cgacctgctg gtcgcgcacg acttcggctt cgtcctggcc    300
acgtccaccg gcgcgctacc cgcatggatc gcgcaacgct accccgacgc cacgcgcacc    360
gactacgaag gccgtcgcca ccgcttcggc gtgcggcaca acgcctgccc gaattcgccg    420
aacttcctgc gcctggccgg cgcgctggcc ggcaagctcg ccgaacgcta cggcgccaac    480
gaccatctga tcgcctggca catctccaac gagctcggcg gccgctgcta ctgcgacaac    540
tgcgccgccg ccttccgcgt ctggctcgaa cgcaagtacg gttcgatcga ggcgttgaac    600
cgcgcgtgga acgcgaactt ctggagccat acctacgccg atttcgccca gatcctaccg    660
ccgaacgcga tcagcgacgg actggacggc gagcgcgcca ctctgtccgc ctgcagcatc    720
gactacaagc ggttccagtc cgactcgctg ctgggcacct acgtcaccga gcgcgacgcg    780
atccgcgcgt tcgacgcgat gcatccgatc accacgaacc tcatggacac ctacgagggt    840
gccgattatt tccgttgggg gcgcgagatg gacgtgatca gctgggacga ttatccgttc    900
ccgcacacca cgccttccga caatgcgttc aagcacgatc tgatgcgcgg cgtgggcgac    960
ggcaggccgt tcatgctcat ggagtcgacg ccgaaccaga cgaactggca ggagtgcaac    1020
gtactgcgcg cgcccgggcg gatgcgtgcg gaaagctatc aggcggtcgc gcatggcgcg    1080
gataccgtgc agtattccca gctcaagcag tcgcgcggcg ggttcgagaa gtaccatggc    1140
gcggtgatct cgcacggcgg gcgcgaggac gagcgcgtgt acgcgaggt gcgtgcgctc    1200
```

```
ggcggcgagc tggcggcgca cggcgcgcgg ttcgtgggcg gtctgaccga ggcgccggtc   1260
gcgctgatgt tcgactggga ttcgtattgg tcgaccgaga acatttcgtt gctgccgaag   1320
ggcttcgact atccggatca ggtgcggcgc tggtatgcgc cgttccacca ccgcaacatc   1380
gcggtggatg tggtgccgga agacattgac gccgggcggc tggcgggcta tcgcgtgctg   1440
gtcgcgccgg cgctcatgat ggccaagccg ggcgttcgtg agctggtcga ggggttcgtg   1500
cgcgccggcg gcacgttcct ggcgacggtg atggcaggca tgcacgacga gcatgacaac   1560
gtgatcctcg gcggataccc gggcgcgttc cgtgaggtgt gcggaatgcg catggaggag   1620
atggacatga tcccggacgg ccgcgacgtg cgtgtcgtgt tcggttcggg cgagggcgag   1680
gacgcggaca cggacgggtc ccgggtctcg ctggttgccg ggctgatcaa gctcgacggc   1740
ggggcgcgcc ctctggcggc ctacgccggc gacgtgttct accggggtac gccggcggtg   1800
acggtgaacg atttcggcgc gggcacggcg tatttcgccg gtgcggtgct ggacgaggcc   1860
ggcatggacg ccgtggtcgg cgacgtgtg cgccgggccg gcgttaccgg catcgtctcg   1920
ccggagccgg tggaggtggt tacgcggcgg tacccgtcac gcggggagtc gttgacgttc   1980
gtgatcaacc atgcggatac ggccacggcg tggcaggata cgccgttcgc cggatgcgag   2040
tcggtgcttg acggcacggt actgggcagg gatctggtgc tggagccgta cggcgtgacg   2100
gtggtgcgca ccgcggcatg a                                              2121

<210> SEQ ID NO 14
<211> LENGTH: 2025
<212> TYPE: DNA
<213> ORGANISM: Bifidobacterium longum
<220> FEATURE:
<223> OTHER INFORMATION: beta-galactosiidase IV, contig 28, gene 1314

<400> SEQUENCE: 14
atgatgtcca ccgcaactgg tttcccaaat cgccagatta atctggattt tcataccagt     60
ccttacgttg agcatgtcgc cgacgatttc gacgccgagg aattcgcgga acgtctgcat    120
cgttctcacg taaactcgat aacctgtttc gcccgtgacc atcacggcta cctgttctat    180
ccctcgaagc gccatcccga gctcgtgcat ccgcaccctgt cggacaggaa tctcctgctt    240
gagcagatag acgcctgcca caagcgcggc atccgcgtcc ccgtctacac gagcgtgggc    300
tgggacgggt acagcgcgct caaccatccc gagtggcttg cccgggaccc ccaagacaat    360
gtaataaacg gatgcccgtc ggttccaaag ccgaacttct acgattcgct gtgtctgaac    420
agcaattaca gggcctatct catcgatcac ctcaacgaca tcatcgacag cctcggcccg    480
gaccgcgtcg acgggctctt cctggatatc ttctccttgg tgccgtgcga ctgcccgcgt    540
tgccgggagc agatggagcg tcatggcttt gaccacaccg atatccgcca gcgggaacgg    600
tattcggcca tcctgcttga cgagttccgt cgtgaggtcc acgacctcgt ggatgatcgg    660
gtgcctggcg cgactctgtt cttcaacggt ggcatatcg gcccctcgaa caagacctcg    720
ttggacacgt tcacccatct ggaggtcgag agcctgccaa gtggttttg gggctacgac    780 aacttcccaa tcgtgatgag gtacgtgcgc aatctcggca aacccgtggt cggcatgacg    840
ggcaagttcc acacggcttg gggtgatttc cattcgctga gaacgagga cgcgatggaa    900 tacgagtgct tccagatgct gacgatgggc gccggctgct ccatcgggga ccagctccat    960
ccgagaggcg ggttgtccga cgccaccta tgatctgatcg gacgggtcta ctcccaggtg   1020
gaggccctcg aaccgtacac gctggatacc gacacgatgg cggacatagc ggtcatgacg   1080
ccggaacgcg aatggaacat ggacagcgcg ctgtccgatt cgttgatcgg cgccaaccgg   1140
```

```
atgctcacgg aactgggatg ccagttcgac atcatcgatc cggacatgga cttcacgcgg    1200
tacgggctca tcgtccttcc cgacgagatc gtgtcctccc ccgaactcca acggaagctg    1260
ctggactacg tgcatggcgg cggcaaggtc gtcggcacgt acatgtcgat ggacaacggc    1320
tgcgacgaga ccaatccgct gtacggcaac aggatgctgg gcgattccta ttgggatcgg    1380
gatttcatca tgccgaacga cgaggtcggg gcgcgtctgc ccaaagagga gttcgtcatg    1440
tacgagcgtg gcgcgcgggt gaggacggcg ggatcgcggg tgctgctgga ttcggtcgaa    1500
ccctacttca atcgtgaggg gaggtatttc tgctcccacc tgcatgcccc ctcgaccggg    1560
agggtcgggt tccccgcggc gacgcggtac ggcgacgtcg tctatttctc ccacccgttg    1620
ttccgcatct acaaggattt cgccccgtcg tgggtcaagg cgatattcgc cgacgtcctc    1680
gatctgctga tgccgaggca gctggtgcgc aaggaggacg gcatacggt cagcgggctg     1740 gaggtgcagc tgcgccgttc gggttcgcgc aattcgttga tgctgcattg cctgtactac    1800
ccctgcaaga agtcggccgc caacctgtac acgatcgacg agaaggttcc gctgttcgac    1860
cagcgcgtgc gcgtgtatgt gggcgacgcc gagatcgagt cggtccgcgc gatccgtcag    1920
ggcgaggtga tctccgaacg ggactacacc gtggccgacg ggtatgtcga tctgaacatt    1980
cccaagatcg acgggtacga gatcatcgag ttgtcgctga aatga                   2025

<210> SEQ ID NO 15
<211> LENGTH: 648
<212> TYPE: DNA
<213> ORGANISM: Bifidobacterium longum
<220> FEATURE:
<223> OTHER INFORMATION: beta-galactosiidase V, contig 29, gene 1402

<400> SEQUENCE: 15
gtgctcgaag tatgcgacga tctcggcgaa gtggcggcgg atcggacggg ccgcctcgtt     60
cttgggccac aggcgttctg gtcccagcac gtcaacagct ttgccgaggt gctgctgcca    120
cgccacatgg gcggcgacag catggtcaac ccgccccagc ggttgggtta caaacggttc    180
ggcaacgaca tgctgctcga cttctacaag gccgaacgcg acgccatcga agcaatctgc    240
cccggcaagc cgtggtacat gatggagcac tccacctccg ccgtacaatg gaagccgttg    300
aacacgcgca gcgcgccgg tgaactttgg gagctcgacg gcgtccccgc catcaccagt    360 cacccccca cggccaaggc gccgccatct acgtgggctg cgaccttggc cgccacgaca    420
tcacccactt gctcacagaa ctcaacacaa cagcccccc gacgaaagg gctcccgacc    480 aaaggccggg tggggagag atcaacgccg caaccacgac cgcagcagcc acgactcatg    540
accccccgca tcctgcacac catccgccaa tcctcagacg gcaccatccg cttcggtttc    600
tctctgaacc gttcgaagca gcccgttgcc gtcaacggca ttgagtaa                 648

<210> SEQ ID NO 16
<211> LENGTH: 696
<212> TYPE: DNA
<213> ORGANISM: Bifidobacterium longum
<220> FEATURE:
<223> OTHER INFORMATION: N-acetylmannosamine-6-phosphate 2-epimerase I,
      contig 23, gene 875

<400> SEQUENCE: 16
atgaatacta acgatactta ttcgaaacgt cttattgatt cgctccacgg cacactgata     60
gtcagctgtc aagcatatcc cggcgagcca atgcggcatc ccgaaaccat ggcccaagtc    120
gctcaatcag tagtaatcgg cggcgctgcc gccattcgat gccaaggtct tgccgatatc    180
```

| | |
|---|---:|
| agcgccatca aaggccaagt aaaagttcca gtcatcggca tatggaagga aggcgataac | 240 |
| ggcgtataca tcacgccaac gttacgccac gccagagcct gcattatggc gggagccgac | 300 |
| attgtggcac tcgatgctac agatcggcct cggccagacg gtctaactct gcagcagacc | 360 |
| gcgcggcaac tcaaaagcga gggcgcaata ctgatggccg actgcggctg catcgaagac | 420 |
| tccgatgcag ccgtggatgc aggattcgac atcatctcca ccacgctggc tggatacacc | 480 |
| gattcccgcg ccaaaacaga aggaccggat tacgagctcc tcgctcaaat gctggagcgg | 540 |
| caccccacg taccggtgat atgcgagggt aggatacata ctccgtccga tgcggccaaa | 600 |
| gccatagaaa tgggtgcctg gcagccgta gtcggtaccg ccatcaccca ccccatgacg | 660 |
| ataacgtcat ggttcgccga tgcagtaagg tcctga | 696 |

<210> SEQ ID NO 17
<211> LENGTH: 684
<212> TYPE: DNA
<213> ORGANISM: Bifidobacterium longum
<220> FEATURE:
<223> OTHER INFORMATION: N-acetylmannosamine-6-phosphate 2-epimerase II,
      contig 30, gene 1561

<400> SEQUENCE: 17

| | |
|---|---:|
| atgatgagca ggaatccggt tatcgaacgt gtgaaaggcg gactcatcgt cagctgccag | 60 |
| gcgtaccccg gcgaaccgct gcgccacccg gagacgatgg cgcagatggc gatgcggcc | 120 |
| gtcgagggcg gcgcggtcgg catccgctgt cagggactcg ccgacatagc agcgataaag | 180 |
| ggccaggtgg acgtgccggt catcggcatc tggaaggacg gttcgcaagg cgtgtacatc | 240 |
| acgccgacgc tgcgtcatgc gcgctgttgc gcggcggcgg gcgcggacat cgtggccttg | 300 |
| gatgcgacgg gacggccgcg cccggacggg cggacctatg cgcagaccgt gcaggcgttg | 360 |
| catgatgagg gcgtcacggt catggccgat tgcggcagct tcgacgatgc gcgccgcgcc | 420 |
| gtcgatgcgg gcagcgacat catctcgacg acgctttccg ggtacacggg cgaacgggag | 480 |
| aagaccgacg gccccgatct cgagttgctc gagtacatgg tgtcgtcgtt ccccgatacg | 540 |
| cctgtgctgt gcgagggccg catccatacg cccgaacagc tgcatgacgt gatgagccgc | 600 |
| ggcgcgtggg cggccgtcgt cggcacggcg atcacccatc cgacgtcgat cacgcgctgg | 660 |
| ttcgccgccc ggctcgacca ttaa | 684 |

<210> SEQ ID NO 18
<211> LENGTH: 1437
<212> TYPE: DNA
<213> ORGANISM: Bifidobacterium longum
<220> FEATURE:
<223> OTHER INFORMATION: alpha-L-fucosidase I, contig 22, gene 815

<400> SEQUENCE: 18

| | |
|---|---:|
| atgaacaatc ctgcagatgc gggcatcaac ctgaactatc tcgcgaatgt gcgcccatcg | 60 |
| tcgcgccagc ttgcctggca gcgcatggag atgtacgcct tcctgcactt cggcatgaac | 120 |
| accatgacgg acagggagtg gggtcttggg catgaggatc cggcactgtt caacccgcgg | 180 |
| aacgtggacg tggaccagtg gatggacgcg ctggtgccgg cgggatggc cggcgtcatc | 240 |
| ctgacgtgca agcaccacga cggattctgc ctgtggccgt cccgattgac gcggcacacc | 300 |
| gtcgcctcgt cgccgtggcg tgaaggcaag ggcgacctcg ttcgtgaggt cagcgagtcc | 360 |
| gccaggcgtc acggactgaa gttcggcgtg tacctgtccc cgtgggaccg caccgaggaa | 420 |
| tcctacggca agggcaaggc gtacgacgac ttctacgtcg ccagctgac cgagctgctc | 480 |
| acccagtacg ggccgatctt ctccgtctgg cttgatggcg ccaatggcga gggcaagaac | 540 |

```
ggcaagaccc agtactacga ctgggatcgt tactacaacg tcatccgttc gctccagccc      600
gatgcggtga tttccgtgtg cggccccgac gtgcgctggg ccgggaacga agccgggcat      660
gtgcgcgaca acgaatggag cgtcgtgccc cgccgcctgc gttcggcgga actgaccatg      720
gagaagtcgc agcaggagga tgacgcatcc ttcgccacca cggtcagctc ccaggacgac      780
gacctcggca ccgtgaggc ggtcgccgga tacggggaca cgtctgctg gtacccggcc       840 gaggtcgaca cctccatccg ccccgggtgg ttctaccacc agtccgagga cgacaaggtc      900
atgagcgccg atcagctgtt cgacctctgg ctttccgcgg taggcggcaa ttcatcgttg      960
ctgctcaaca ttcctccctc gccggaaggt ctgctcgccg aaccggatgt gcagtcgctc     1020
aagggattgg gccgccgcgt cagcgagttc cgtgaagcgc tggcctcggt ccgctgcgaa     1080
gccaggacca gcagcgcatc cgccgccgcg gcgcatctcg tcgacgggaa tcgggacacg     1140
ttctggcgcc cggatgccga cgatgcggcc cccgccatca cgctcaccct cccgcagccc     1200
acgacgatca acgccatcgt gatcgaggag gccatagagc acggtcagcg catcgagcat     1260
ctgcgcgtca cgggtgcgct gcctgacggc accgagcgcg tgctcggcca ggccggcacg     1320
gtgggttacc ggaggatact ccgcttcgac gatgtcgagg tgtcctcggt caccctttcac    1380 gtggacggtt cgaggcttgc gccgatgatc agccgcgcgg ctgccgtgcg catctga       1437

<210> SEQ ID NO 19
<211> LENGTH: 1350
<212> TYPE: DNA
<213> ORGANISM: Bifidobacterium longum
<220> FEATURE:
<223> OTHER INFORMATION: alpha-L-fucosidase II, contig 25, gene 1206

<400> SEQUENCE: 19
atggtgttgt tcatggccaa tccacagcgt cccaagatgt atgagaagtt cgtgcacgat       60
acacccgaat ggttcaaggg cgccggtctc ggcatcttcg cccactgggg ttcgtattcg      120
gtgccggcat gggcggagcc gatcggtgcg cttggcacct ttgacgatcc ggtgtactgg      180
aacacccact gcccgtatgc ggaatggtat tggaacacga tgagcatcaa gggctcgccg      240
gcggccgagc atcagaagga agtctacggt gacatgccgt atgaggactt catcgacatg      300
tggaaggccg aggcgttcga ccccgcggac atggccgacc tgttcgcacg cgccggtgcc      360
cggtacttcg tgccgaccac gaagcatcac gaaggcatca cgctgtggaa ggcccccgac      420
aacgatgggt ggaataccgt ggaccgtggt ccgcatcgcg atctggtcaa ggaattcgcc      480
gacgccatgc gcgacaaggg actgaagttc ggcgtgtact actcctcggg cctcgactgg      540
cacaaggagc ccaacatgcc gattctcggc gacggggaat acgggccgca gagcgaggac      600
tacgcccgct atatgtactc gcatgtgatg gacctcatcg acgaatacca gccgtccatc      660
ctgtggggag atatcgacgt gccgaagatc tcggaggagg acaacgattt cagcgtggcc      720
cgactgttcg agcattacta cgacgtggtg ccggatggtg tggtcaacga ccgctggggc      780
ctgacccatt gggacttccg caccgtcgaa tacgaacagg gcaaggagct catgggcaag      840
ggcatgtggg agatgacccg aggcatcggc tactccttcg gctacaacca gatggaggac      900
gccgactcct acatgaccgg tccggaggcg gtgaagttgc tcgccgacgt ggtctccatg      960
ggcggcaacc tgctgctcga catcggcccc gacgccgccg acgcatccc cgaactgcag     1020 cgtcagtgcc tcgagggcat ggccgactgg atggacgtga actcgccgag tatccatgat     1080
gtcgaaccgg tgccggaagc ctcgccttcc ggagaggggg acggcagcc atgggtccgt     1140 tggaccggag acggcaagag cgtctatgcc gtcgtcgatg ctgcgggcag ggttccgctg     1200
```

```
cgcatcgccg ccgatgctgt ggacgcggat tccgccgtga cgcttggcgg atccgcagtc    1260
gccgtggacg ccgacggcga cgtgctgacc gccgatgttc cggcctcgga agtggcgggg    1320
ccgcaggtcg tgcacttcgt ccgtcgctga                                     1350
```

<210> SEQ ID NO 20
<211> LENGTH: 684
<212> TYPE: DNA
<213> ORGANISM: Bifidobacterium longum
<220> FEATURE:
<223> OTHER INFORMATION: alpha-L-fucosidase III, contig 29, gene 1394

<400> SEQUENCE: 20

```
ggagatatcg acgtgccgaa gatctcggag gaggacaacg atttcagcgt ggcccgactg     60
ttcgagcatt actacgacgt ggtgccggat ggtgtggtca acgaccgctg gggcctgacc    120
cattgggact ccgcaccgt cgaatacgaa cagggcaagg agctcatggg caagggcatg    180
tgggagatga cccgaggcat cggctactcc ttcggctaca accagatgga ggacgccgac    240
tcctacatga ccggtccgga ggcggtgaag ttgctcgccg acgtggtctc catgggcggc    300
aacctgctgc tcgacatcgg ccccgacgcc gccggacgca tccccgaact gcagcgtcag    360
tgcctcgagg gcatggccga ctggatggac gtgaactcgc cgagtatcca tgatgtcgaa    420
ccggtgccgg aagcctcgcc ttccggagag ggggacggcg agccatgggt tcgttggacc    480
ggagacggca agagcgtcta tgccgtcgtc gatgctgcgg gcagggttcc gctgcgcata    540
gatgcgggtg cggtcgatgt ggattccgca accattcttg gcggtggcaa cgttgtcgtg    600
gaggcggacg gcgatatgct gaccgtggag attcccgcga cagacgtcgc cggccctcag    660
gtcgtgcgtt ttgctcgaca ctaa                                           684
```

<210> SEQ ID NO 21
<211> LENGTH: 447
<212> TYPE: DNA
<213> ORGANISM: Bifidobacterium longum
<220> FEATURE:
<223> OTHER INFORMATION: fucose dissimilation pathway protein I (fucose
      mutarotase), contig 20, gene 785

<400> SEQUENCE: 21

```
atgctcaaag gtattccgaa aatcatcccg ccggagctgc tgaaagtgct gtgcgagatg     60
ggtcatggcg atcagctggt catcgcggac ggcaacttcc cagccgaatc aatcggcaag    120
aacgcaatcg tggttcgtat ggacggccac ggtggcggcg agatcctcaa agcgattctg    180
acggtgttcc cgcttgacac gtatgtggac aagccggcga cgctgatgga aaaagtgccg    240
ggcgatacgt tgcgacgcc gatctgggat gtgtacgcgg gcctcatcaa ggagcatgac    300
gaacgcggtg cggatgcgat tggatcgctt gagcgcttcg cgttctatga gcaggcgaag    360
aacgcctact gtgtgattgc cagcggcgag tcggcgcagt acgcgaacct aatcctgcag    420
aagggagtcg tcttcaacgc ggaataa                                        447
```

<210> SEQ ID NO 22
<211> LENGTH: 438
<212> TYPE: DNA
<213> ORGANISM: Bifidobacterium longum
<220> FEATURE:
<223> OTHER INFORMATION: fucose dissimilation pathway protein II (fucose
      mutarotase), contig 22, gene 816

<400> SEQUENCE: 22

```
atgctgaagg gaataccgcc gatcatacag cccgatctgc tgaagatact cagcgagatg     60
```

-continued

```
ggccacggcg atgccatagt ccttgcggac gcccactttc ccgccgaatc ggtgggcgtc      120
cgatcccacg tgatcaggta tgacggccag cccatcgagc cgctgctcga cgcggtgctg      180
cagctgatac cgctggacca atacacggaa cacccggtgc tgctgatgga caaggttccc      240
ggagacaccg tggacacccc gatatgggac cggtaccgtc aggtcatcga caggcacgag      300
cccggcaagc aagcgggcat cgggatgctg aacggttcg ccttctacga ggaggccggc       360
aggtcctatt gcatcgtcgc caccggcgaa caatcgcagt atgcgaacat catcatcaga      420
aaaggcgtca ttcgctaa                                                    438
```

<210> SEQ ID NO 23
<211> LENGTH: 651
<212> TYPE: PRT
<213> ORGANISM: Bifidobacterium longum
<220> FEATURE:
<223> OTHER INFORMATION: N-acetyl-beta-hexosaminidase III, contig 30, gene 1639 translation

<400> SEQUENCE: 23

| | | | | | | | | | | | | | | |
|---|---|---|---|---|---|---|---|---|---|---|---|---|---|---|
| Val | Pro | Thr | Ser | Glu | His | Lys | Ala | Asp | Asp | Ala | Thr | Arg | His | Leu | Thr |
| 1 | | | | 5 | | | | | 10 | | | | | 15 | |
| Leu | Ile | Pro | Ala | Pro | Val | Thr | Leu | Glu | Tyr | Thr | His | Gly | Thr | Ala | Leu |
| | | | 20 | | | | | 25 | | | | | 30 | | |
| Ile | Gly | Pro | Leu | Val | Thr | Ile | Glu | Asp | Ala | Asp | Gln | Ser | Trp | Glu | Thr |
| | | 35 | | | | | 40 | | | | | 45 | | | |
| Leu | Pro | Ile | Glu | Gln | Leu | Ser | Asp | Glu | Leu | Arg | His | Arg | Tyr | Gly | Val |
| | 50 | | | | | 55 | | | | | 60 | | | | |
| Thr | Val | Leu | Arg | Arg | Arg | Thr | His | Gly | Thr | Val | Ile | Ser | Leu | Gly | Leu |
| 65 | | | | | 70 | | | | | 75 | | | | | 80 |
| Asp | Ser | Arg | Leu | Ala | His | Asp | Glu | Tyr | Thr | Leu | Asp | Val | Ser | Glu | Ser |
| | | | | 85 | | | | | 90 | | | | | 95 | |
| Glu | Gly | Ile | Arg | Val | Arg | Gly | Gly | Gly | Glu | Ser | Gly | Leu | Arg | Tyr | Gly |
| | | | 100 | | | | | 105 | | | | | 110 | | |
| Leu | Gln | Thr | Leu | Arg | Gln | Ile | Ile | Gly | Gln | Thr | Ser | Arg | Ala | Ile | Pro |
| | | 115 | | | | | 120 | | | | | 125 | | | |
| Cys | Leu | His | Ile | Gln | Asp | Lys | Pro | Ala | Phe | Ala | Val | Arg | Ala | Tyr | Ser |
| | 130 | | | | | 135 | | | | | 140 | | | | |
| Leu | Asp | Val | Thr | Arg | Gly | Arg | Val | Pro | Thr | Met | Glu | Phe | Leu | Thr | Trp |
| 145 | | | | | 150 | | | | | 155 | | | | | 160 |
| Phe | Val | Asp | Gln | Leu | Ala | Leu | Tyr | Lys | Tyr | Asn | Gln | Phe | Gln | Leu | Tyr |
| | | | | 165 | | | | | 170 | | | | | 175 | |
| Val | Glu | His | Ala | Phe | Ala | Phe | Val | Glu | Leu | Ser | Glu | Ala | Trp | Arg | Gly |
| | | | 180 | | | | | 185 | | | | | 190 | | |
| Thr | Asp | Pro | Leu | Thr | Ala | Ala | Asp | Ile | Thr | Tyr | Leu | Asp | Glu | Tyr | Cys |
| | | 195 | | | | | 200 | | | | | 205 | | | |
| Ala | Arg | Arg | Gly | Ile | Glu | Leu | Val | Pro | Ser | Leu | Ala | Thr | Phe | Gly | His |
| | 210 | | | | | 215 | | | | | 220 | | | | |
| Met | Tyr | Met | Asn | Leu | Arg | Thr | Arg | Glu | His | Arg | Gly | Leu | Gly | Glu | Phe |
| 225 | | | | | 230 | | | | | 235 | | | | | 240 |
| Pro | Glu | Asp | Ala | Asp | Arg | Pro | Phe | Ser | Phe | Ile | Glu | Arg | Met | Glu | His |
| | | | | 245 | | | | | 250 | | | | | 255 | |
| His | Thr | Leu | Asn | Ala | Ala | Asp | Pro | Lys | Ala | His | Asp | Phe | Ala | Ser | Arg |
| | | | 260 | | | | | 265 | | | | | 270 | | |
| Leu | Ile | Glu | Glu | Tyr | Ala | Pro | Leu | Phe | Arg | Ser | Lys | Ser | Phe | Asn | Ile |
| | | 275 | | | | | 280 | | | | | 285 | | | |

Gly Gly Asp Glu Thr Phe Asp Leu Gly Arg Gly Arg Ser Ala Gln Asp
            290                 295                 300
Ala Pro Glu Ala Gly Arg Asp Glu Leu Tyr Ala Gly Phe Val Arg Asp
305                 310                 315                 320
Leu Cys Glu Thr Leu Ala Arg His Gly Arg Gln Pro Met Leu Trp Ala
                325                 330                 335
Asp Ile Ala Leu Glu Ser Pro Arg Thr Met Asp Leu Leu Pro Gly Asp
                340                 345                 350
Ile Thr Met Leu Asn Trp Met Tyr Glu Pro Gln Ile Asp Glu Ser Lys
                355                 360                 365
Ile Gln Thr Ile Ala Thr Gln Gly Arg Arg Gln Phe Val Cys Pro Ala
370                 375                 380
Val Arg Ala Trp Ser Arg Phe Phe Pro Asp Tyr Ala Gly Ala Trp Leu
385                 390                 395                 400
Asn Thr Tyr His Met Ala Leu Ala Gly Thr Lys Tyr Asp Ala Glu Gly
                405                 410                 415
Met Val Val Thr Asp Trp Gly Asp Tyr Gly His Val Asn Asp Pro Arg
                420                 425                 430
Leu Ser Val Pro Gly Leu Cys Tyr Gly Ala Gln Asn Ala Trp Asn Pro
                435                 440                 445
Ile Glu Ile Asp Ala His Glu Met Asn Arg Arg Ile Ser Ala Leu Val
450                 455                 460
Tyr Gly Asp Glu Ser Gly Arg Ile Met Asp Cys Leu Ala Arg Ile Asp
465                 470                 475                 480
Ser Asp Gly Val Ser Phe Pro Trp Asp Leu Ala Val Gln Val Leu Glu
                485                 490                 495
Leu Glu Tyr Gly Ser Gly Thr Gly Ala Leu Asn Met Asp Val Ala Ala
                500                 505                 510
Cys Met Glu Arg Ser Ser Gly Gly Lys Leu Thr Leu Asp Arg Thr Leu
                515                 520                 525
Gly Cys Asp Asp Ala Arg Arg Arg Met Leu Gln Trp Asn Arg Glu Arg
                530                 535                 540
Ile Glu Arg Arg Arg Asp Cys Asp Gln Val Leu Arg Asp Cys Gly Asp
545                 550                 555                 560
Ala Phe Ala Gly Leu Asp Lys Gly Gly Leu Thr Ala Glu Phe Leu Ser
                565                 570                 575
Val Met Leu Asp Gly Gln Arg Leu Phe Asn Glu Leu Gly Glu Glu Leu
                580                 585                 590
Leu Ala Leu Ala Asp Gly Lys Asp Val Gly Ser Gly Ala Asn Arg Leu
                595                 600                 605
Ala Ala Asp Leu Glu Leu Trp Phe Glu Arg Tyr Arg Ala Gln Trp Leu
                610                 615                 620
Ser Val Gly Arg His Ala Glu Leu Ala Arg Ile Ala His Val Val Trp
625                 630                 635                 640
Ser Leu Ala Asp Ile Leu Arg Arg Gly Ala Leu
                645                 650

<210> SEQ ID NO 24
<211> LENGTH: 711
<212> TYPE: PRT
<213> ORGANISM: Bifidobacterium longum
<220> FEATURE:
<223> OTHER INFORMATION: beta-hexosaminidase A, N-acetyl-beta-
      glucosaminidase, beta-N-acetylhexosaminidase; COG family,
      locus BL0056

<400> SEQUENCE: 24

```
Met Pro Thr Phe Glu Tyr Lys Ala Asp Ala Thr Pro Cys Leu Thr
1               5                   10                  15

Leu Ile Pro Ala Pro Val Thr Leu Glu Tyr Thr His Gly Thr Ala Met
            20                  25                  30

Ile Gly Ser Leu Val Thr Ile Glu Lys Arg Ile Pro Glu Tyr Ala Val
        35                  40                  45

Thr Glu Asp Ala Asp Glu Thr Trp Glu Thr Leu Pro Ile Glu Gln Leu
50                  55                  60

Ser Ser Glu Leu Glu Arg Tyr Cys Gly Val Ala Val Arg Thr Arg Arg
65              70                  75                  80

Val Leu Thr Ala Thr Asp Glu Asp Ala Gly Ala Asn Ala Ala Glu
                85                  90                  95

Lys Ala Arg Asp Ala Gly Val Gly Ala Gly Ala Gly Ala Pro
                100                 105                 110

Ala Ala Met Asn Gly Thr Val Ile Leu Leu Cys Val Asp Ala Arg Leu
            115                 120                 125

Ala His Asp Glu Tyr Thr Leu Asp Val Phe Ala Ser Asp Thr Ile Ala
        130                 135                 140

Val Arg Gly Gly Ser Glu Ser Gly Leu Arg Tyr Gly Met Gln Thr Leu
145                 150                 155                 160

Arg Gln Met Ile Arg Gln Thr Ser Arg Thr Leu Pro Cys Leu His Ile
                165                 170                 175

Gln Asp Lys Pro Ala Phe Ala Val Arg Ala Tyr Ser Leu Asp Val Thr
            180                 185                 190

Arg Gly Arg Val Pro Thr Met Ala Phe Leu Thr Trp Phe Ile Asp Gln
        195                 200                 205

Leu Ala Leu Tyr Lys Tyr Asn Gln Phe Gln Leu Tyr Val Glu His Ala
    210                 215                 220

Phe Ala Phe Gly Glu Leu Ser Glu Ala Trp Arg Gly Thr Asp Pro Leu
225                 230                 235                 240

Thr Ala Asp Asp Ile Met Phe Leu Asp Glu Tyr Cys Ala His His Gly
                245                 250                 255

Ile Glu Leu Val Pro Ser Leu Ala Thr Phe Gly His Met Tyr Met Asn
            260                 265                 270

Leu Arg Thr Arg Glu His Arg Gly Leu Gly Glu Phe Pro Glu Asp Ala
        275                 280                 285

Asp Arg Pro Phe Ser Phe Ile Glu Arg Met Glu His His Thr Leu Asn
    290                 295                 300

Ala Ala Asn Pro Lys Ser His Asp Phe Ala Ser Arg Leu Ile Glu Glu
305                 310                 315                 320

Tyr Ala Pro Leu Phe Arg Ser Arg Ser Phe Asn Ile Gly Gly Asp Glu
                325                 330                 335

Thr Phe Asp Leu Gly Arg Gly Arg Ser Val Gln Asp Ser Pro Gly Ala
            340                 345                 350

Ser Arg Asp Glu Leu Tyr Ala Asp Phe Val Lys Asp Leu Cys Ser Thr
        355                 360                 365

Leu Ala His Arg Gly Leu Gln Pro Met Leu Trp Ala Asp Ile Ala Leu
    370                 375                 380

Glu Asn Pro His Thr Met Asp Leu Leu Pro Gly Asp Ile Thr Met Leu
385                 390                 395                 400

Asn Trp Met Tyr Glu Pro Asp Ile Asp Glu Ser Lys Ile Gln Thr Ile
                405                 410                 415

Ala Ser Gln Gly Arg Arg Gln Phe Val Cys Pro Ala Val Arg Ala Trp
```

```
                       420                 425                 430
Ser Arg Phe Phe Pro Asp Tyr Asp Gly Ala Trp Leu Asn Thr Tyr Arg
    435                 440                 445

Met Ala Val Ala Gly Leu Lys Tyr Gly Ala Glu Gly Met Val Val Thr
    450                 455                 460

Asp Trp Gly Asp Tyr Gly His Val Asn Asp Pro Arg Leu Ser Val Pro
465                 470                 475                 480

Gly Leu Cys Tyr Gly Ala Gln Asn Ala Trp Asn Pro Val Ala Ile Asp
                485                 490                 495

Ala Cys Glu Met Asn His Arg Ile Ser Asn Leu Ala Tyr Gly Asp Glu
            500                 505                 510

Ser Gly Trp Leu Met Asp Ser Leu Ala Arg Ile Asp Ser Asp Gly Val
        515                 520                 525

Ser Phe Pro Trp Asp Leu Ala Val Gln Val Leu Glu Leu Glu Tyr Gly
    530                 535                 540

Ser Gly Thr Gly Met Leu Asn Thr Asp Val Ala Ser Cys Val Glu Arg
545                 550                 555                 560

Ser Cys Gly Gly Glu Leu Val Phe Asp Arg Thr Leu Gly Cys Ala Asp
                565                 570                 575

Ala Arg Arg Arg Leu Leu Arg Asn His Ala Arg Leu Glu Arg Arg
            580                 585                 590

Arg Asp Cys Asp Arg Ala Leu Ile Asp Cys Gly Ser Ala Val Val Ala
        595                 600                 605

Val Leu Asp Gly Ser Ala Arg Gly Gly Leu Asn Pro Glu Leu Leu Trp
    610                 615                 620

Val Met Leu Asp Gly Gln Arg Leu Phe Asn Arg Leu Gly Glu Glu Leu
625                 630                 635                 640

Leu Val Leu Ala Gly Gly Glu Asp Ala Cys Asp Thr Lys Asp Val Thr
                645                 650                 655

Gly Arg Ala Leu Asp Ala Ser Arg Ala Arg Leu Ala Ala Asp Leu
            660                 665                 670

Glu Leu Trp Phe Glu Arg Tyr Arg Val Gln Trp Leu Ser Ile Gly Arg
        675                 680                 685

Tyr Ala Glu Leu Ala Arg Ile Ala His Val Val Trp Ser Phe Ala Asp
    690                 695                 700

Ile Leu Arg Arg Gly Ala Leu
705                 710

<210> SEQ ID NO 25
<211> LENGTH: 17
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 25

Leu Thr Leu Ile Pro Ala Pro Val Thr Leu Glu Tyr Thr His Gly Thr
1               5                   10                  15

Ala

<210> SEQ ID NO 26
<211> LENGTH: 5
<212> TYPE: PRT
<213> ORGANISM: Artificial Sequence
<220> FEATURE:
<223> OTHER INFORMATION: N-acetyl-beta-hexosaminidase III consensus
      peptide
```

```
<400> SEQUENCE: 26

Leu Val Thr Ile Glu
 1               5

<210> SEQ ID NO 27
<211> LENGTH: 10
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 27

Trp Glu Thr Leu Pro Ile Glu Gln Leu Ser
 1               5                  10

<210> SEQ ID NO 28
<211> LENGTH: 4
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 28

Gly Thr Val Ile
 1

<210> SEQ ID NO 29
<211> LENGTH: 11
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 29

Arg Leu Ala His Asp Glu Tyr Thr Leu Asp Val
 1               5                  10

<210> SEQ ID NO 30
<211> LENGTH: 4
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 30

Val Arg Gly Gly
 1

<210> SEQ ID NO 31
<211> LENGTH: 7
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 31

Glu Ser Gly Leu Arg Tyr Gly
 1               5

<210> SEQ ID NO 32
<211> LENGTH: 5
<212> TYPE: PRT
```

```
<213> ORGANISM: Artificial Sequence
<220> FEATURE:
<223> OTHER INFORMATION: N-acetyl-beta-hexosaminidase III consensus
      peptide

<400> SEQUENCE: 32

Gln Thr Leu Arg Gln
 1               5

<210> SEQ ID NO 33
<211> LENGTH: 4
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 33

Gln Thr Ser Arg
 1

<210> SEQ ID NO 34
<211> LENGTH: 28
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 34

Pro Cys Leu His Ile Gln Asp Lys Pro Ala Phe Ala Val Arg Ala Tyr
 1               5                  10                  15

Ser Leu Asp Val Thr Arg Gly Arg Val Pro Thr Met
            20                  25

<210> SEQ ID NO 35
<211> LENGTH: 5
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 35

Phe Leu Thr Trp Phe
 1               5

<210> SEQ ID NO 36
<211> LENGTH: 21
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 36

Asp Gln Leu Ala Leu Tyr Lys Tyr Asn Gln Phe Gln Leu Tyr Val Glu
 1               5                  10                  15

His Ala Phe Ala Phe
            20

<210> SEQ ID NO 37
<211> LENGTH: 14
<212> TYPE: PRT
<213> ORGANISM: Artificial Sequence
<220> FEATURE:
<223> OTHER INFORMATION: N-acetyl-beta-hexosaminidase III consensus
      peptide
```

```
<400> SEQUENCE: 37

Glu Leu Ser Glu Ala Trp Arg Gly Thr Asp Pro Leu Thr Ala
1               5                   10

<210> SEQ ID NO 38
<211> LENGTH: 6
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 38

Leu Asp Glu Tyr Cys Ala
1               5

<210> SEQ ID NO 39
<211> LENGTH: 51
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 39

Gly Ile Glu Leu Val Pro Ser Leu Ala Thr Phe Gly His Met Tyr Met
1               5                   10                  15

Asn Leu Arg Thr Arg Glu His Arg Gly Leu Gly Glu Phe Pro Glu Asp
            20                  25                  30

Ala Asp Arg Pro Phe Ser Phe Ile Glu Arg Met Glu His His Thr Leu
        35                  40                  45

Asn Ala Ala
    50

<210> SEQ ID NO 40
<211> LENGTH: 17
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 40

His Asp Phe Ala Ser Arg Leu Ile Glu Glu Tyr Ala Pro Leu Phe Arg
1               5                   10                  15

Ser

<210> SEQ ID NO 41
<211> LENGTH: 17
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 41

Ser Phe Asn Ile Gly Gly Asp Glu Thr Phe Asp Leu Gly Arg Gly Arg
1               5                   10                  15

Ser

<210> SEQ ID NO 42
<211> LENGTH: 6
<212> TYPE: PRT
<213> ORGANISM: Artificial Sequence
```

```
<220> FEATURE:
<223> OTHER INFORMATION: N-acetyl-beta-hexosaminidase III consensus
      peptide

<400> SEQUENCE: 42

Arg Asp Glu Leu Tyr Ala
1               5

<210> SEQ ID NO 43
<211> LENGTH: 11
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 43

Gln Pro Met Leu Trp Ala Asp Ile Ala Leu Glu
1               5                   10

<210> SEQ ID NO 44
<211> LENGTH: 18
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 44

Thr Met Asp Leu Leu Pro Gly Asp Ile Thr Met Leu Asn Trp Met Tyr
1               5                   10                  15

Glu Pro

<210> SEQ ID NO 45
<211> LENGTH: 10
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 45

Ile Asp Glu Ser Lys Ile Gln Thr Ile Ala
1               5                   10

<210> SEQ ID NO 46
<211> LENGTH: 21
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 46

Gln Gly Arg Arg Gln Phe Val Cys Pro Ala Val Arg Ala Trp Ser Arg
1               5                   10                  15

Phe Phe Pro Asp Tyr
            20

<210> SEQ ID NO 47
<211> LENGTH: 7
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 47
```

```
Gly Ala Trp Leu Asn Thr Tyr
 1               5
```

<210> SEQ ID NO 48
<211> LENGTH: 35
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 48

```
Ala Glu Gly Met Val Val Thr Asp Trp Gly Asp Tyr Gly His Val Asn
 1               5                  10                  15

Asp Pro Arg Leu Ser Val Pro Gly Leu Cys Tyr Gly Ala Gln Asn Ala
             20                  25                  30

Trp Asn Pro
         35
```

<210> SEQ ID NO 49
<211> LENGTH: 6
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 49

```
Tyr Gly Asp Glu Ser Gly
 1               5
```

<210> SEQ ID NO 50
<211> LENGTH: 29
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 50

```
Leu Ala Arg Ile Asp Ser Asp Gly Val Ser Phe Pro Trp Asp Leu Ala
 1               5                  10                  15

Val Gln Val Leu Glu Leu Glu Tyr Gly Ser Gly Thr Gly
             20                  25
```

<210> SEQ ID NO 51
<211> LENGTH: 6
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 51

```
Asp Arg Thr Leu Gly Cys
 1               5
```

<210> SEQ ID NO 52
<211> LENGTH: 5
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 52

```
-continued

Asp Ala Arg Arg Arg
 1               5

<210> SEQ ID NO 53
<211> LENGTH: 7
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 53

Glu Arg Arg Arg Asp Cys Asp
 1               5

<210> SEQ ID NO 54
<211> LENGTH: 10
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 54

Val Met Leu Asp Gly Gln Arg Leu Phe Asn
 1               5                  10

<210> SEQ ID NO 55
<211> LENGTH: 6
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 55

Leu Gly Glu Glu Leu Leu
 1               5

<210> SEQ ID NO 56
<211> LENGTH: 14
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 56

Arg Leu Ala Ala Asp Leu Glu Leu Trp Phe Glu Arg Tyr Arg
 1               5                  10

<210> SEQ ID NO 57
<211> LENGTH: 4
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 57

Gln Trp Leu Ser
 1

<210> SEQ ID NO 58
<211> LENGTH: 12
<212> TYPE: PRT
<213> ORGANISM: Artificial Sequence
<220> FEATURE:
<223> OTHER INFORMATION: N-acetyl-beta-hexosaminidase III consensus
```

```
                                peptide

<400> SEQUENCE: 58

Ala Glu Leu Ala Arg Ile Ala His Val Val Trp Ser
 1               5                  10

<210> SEQ ID NO 59
<211> LENGTH: 9
<212> TYPE: PRT
<213> ORGANISM: Artificial Sequence
<220> FEATURE:
<223> OTHER INFORMATION: N-acetyl-beta-hexosaminidase III consensus
      peptide

<400> SEQUENCE: 59

Ala Asp Ile Leu Arg Arg Gly Ala Leu
 1               5

<210> SEQ ID NO 60
<211> LENGTH: 713
<212> TYPE: PRT
<213> ORGANISM: Bifidobacterium longum
<220> FEATURE:
<223> OTHER INFORMATION: beta-galactosiidase II, contig 18, gene 584
      translation positions 109-821

<400> SEQUENCE: 60

Ala Arg Arg Asp Phe Ala Trp Pro Lys Leu Leu Thr Ala Asp Gly Arg
 1               5                  10                  15

Gly Ile Ala Phe Gly Gly Asp Tyr Asn Pro Asp Gln Trp Pro Glu Asp
                20                  25                  30

Val Trp Asp Asp Ile Arg Leu Met Gly Gln Ala Gly Val Asn Thr
             35                  40                  45

Val Ala Leu Ala Ile Phe Ser Trp Asp Arg Leu Gln Pro Thr Glu Asp
         50                  55                  60

His Trp Asn Phe Asp Trp Leu Asp Arg Ile Ile Asp Lys Leu Gly Gln
 65                  70                  75                  80

Ala Gly Ile Ala Val Asp Leu Ala Ser Ala Thr Ala Thr Ala Pro Leu
                 85                  90                  95

Trp Leu Tyr Glu Asn His Pro Glu Val Leu Pro Arg Asp Lys Tyr Gly
                100                 105                 110

His Pro Val Asn Ala Gly Ser Arg Gln Ser Trp Ser Pro Thr Ser Pro
            115                 120                 125

Val Phe Lys Glu Tyr Ala Leu Thr Leu Cys Arg Lys Leu Ala Glu Arg
        130                 135                 140

Tyr Gly Thr Asn Pro Tyr Val Thr Ala Trp His Met Gly Asn Glu Tyr
145                 150                 155                 160

Gly Trp Asn Asn Arg Asp Asp Tyr Ser Asp Asn Ala Leu Glu Ala Phe
                165                 170                 175

Arg Ala Trp Cys Arg Arg Lys Tyr Gly Thr Ile Asp Ala Leu Asn Gln
            180                 185                 190

Ala Trp Gly Thr Thr Phe Trp Gly Gln Glu Met Thr Gly Phe Asp Glu
        195                 200                 205

Val Leu Ile Pro Arg Phe Met Gly Ala Asp Ser Met Val Asn Pro Gly
    210                 215                 220

Gln Lys Leu Asp Phe Glu Arg Phe Gly Asn Asp Met Leu Leu Asp Phe
225                 230                 235                 240

Tyr Lys Ala Glu Arg Asp Ala Ile Ala Glu Ile Cys Pro Asp Lys Pro
                245                 250                 255
```

```
Phe Thr Thr Asn Phe Met Ile Ser Thr Asp Gln Cys Cys Met Asp Tyr
                260                 265                 270

Ala Ala Trp Ala Glu Glu Val Asn Phe Val Ser Asn Asp His Tyr Phe
            275                 280                 285

His Glu Gly Glu Ser His Leu Asp Glu Leu Ala Cys Ser Asp Ala Leu
        290                 295                 300

Val Asp Ser Leu Ala Leu Gly Lys Pro Trp Tyr Val Met Glu His Ser
305                 310                 315                 320

Thr Ser Ala Val Gln Trp Lys Pro Leu Asn Thr Arg Lys Arg Asn Gly
                325                 330                 335

Glu Thr Val Arg Asp Ser Leu Ala His Val Ala Met Gly Ala Asp Ala
            340                 345                 350

Ile Asn Phe Phe Gln Trp Arg Ala Ser Ala Phe Gly Ala Glu Ala Phe
        355                 360                 365

His Ser Ala Met Val Pro His Ala Gly Glu Asn Thr Lys Leu Phe Arg
    370                 375                 380

Gln Val Cys Glu Leu Gly Ala Thr Leu Gln Ala Leu Ala Asp Ala Gly
385                 390                 395                 400

Val Gln Gly Ser Glu Leu Ala His Ala Asp Thr Ala Ile Leu Phe Ser
                405                 410                 415

Ala Glu Ser Glu Trp Ala Thr Arg Ser Glu Thr Leu Pro Ser Met Lys
            420                 425                 430

Leu Asn His Trp His Asp Val Arg Asp Trp Tyr Arg Ala Phe Leu Asn
        435                 440                 445

Ala Gly Ala Arg Ala Asp Ile Val Pro Leu Ala Tyr Asp Trp Ser Ser
    450                 455                 460

Tyr Lys Thr Ile Val Leu Pro Thr Val Leu Met Leu Ser Asp Ala Asp
465                 470                 475                 480

Thr Arg Arg Leu Ala Gly Phe Val Gln Asp Gly Gly Arg Val Val Val
                485                 490                 495

Gly Tyr Ala Thr Gly Leu Leu Asp Glu Arg Phe His Thr Trp Leu Gly
            500                 505                 510

Gly Tyr Pro Gly Ala Gly Asp Gly Leu Leu Arg Ser Met Leu Gly Val
        515                 520                 525

Arg Gly Glu Glu Phe Asn Ile Leu Gly Thr Glu Thr Glu Asp Glu Pro
    530                 535                 540

Ser Glu Ile Arg Leu Ala Ser Thr Gly Asp Ser Pro Thr Met Asp Gly
545                 550                 555                 560

Ala Val Thr Arg Leu Trp Gln Asn Asp Val Thr Val Ala Gly Pro His
                565                 570                 575

Val Gln Val Leu Ala Ala Tyr Ala Gly Glu Glu Ala Asn Glu Trp Glu
            580                 585                 590

Leu Asp Gly Thr Ala Ala Ile Thr Arg Asn Tyr Gly Glu Gly Glu
        595                 600                 605

Ala Tyr Phe Leu Gly Cys Asp Leu Gly Val Ser Asp Leu Thr Arg Phe
    610                 615                 620

Val Gly Gly Trp Leu Ala Ala Arg Pro Gln Asp Gly Arg Gln Pro Glu
625                 630                 635                 640

Ala Asn Leu Arg Ser Pro Ala Ser Gly Val Thr Ser Asp Val Leu His
                645                 650                 655

Thr Val Arg Gln Ser Asp Asp Ala Ile Phe Asp Phe Tyr Leu Thr Arg
            660                 665                 670

Gly Lys Ser Asp Val Glu Leu Arg Asp Ile Ala Gly Glu Pro Ile Val
        675                 680                 685
```

-continued

```
Leu Phe Arg Ala Glu Arg Gly Ser Asp Gly Ala Tyr Thr Val His
    690                 695                 700

Arg Asn Gly Val Leu Val Met Lys Arg
705                 710

<210> SEQ ID NO 61
<211> LENGTH: 699
<212> TYPE: PRT
<213> ORGANISM: Bifidobacterium adolescentis
<220> FEATURE:
<223> OTHER INFORMATION: beta-galactosidase (bGalA, bgalII) positions
      3-701

<400> SEQUENCE: 61

Ala Arg Arg Asn Phe Glu Trp Pro Glu Leu Leu Thr Ala Asp Gly Arg
  1               5                  10                  15

Gly Ile Ala Phe Gly Gly Asp Tyr Asn Pro Asp Gln Trp Ser Glu Asp
             20                  25                  30

Ile Trp Asp Asp Asp Ile Arg Leu Met Lys Gln Ala Gly Val Asn Thr
         35                  40                  45

Val Ala Leu Ala Ile Phe Ser Trp Asp Arg Ile Gln Pro Thr Glu Asp
 50                  55                  60

Arg Trp Asp Phe Gly Trp Leu Asp Arg Ile Ile Asp Lys Leu Gly Asn
 65                  70                  75                  80

Ala Gly Ile Val Val Asp Leu Ala Ser Ala Thr Ala Thr Ala Pro Leu
                 85                  90                  95

Trp Leu Tyr Glu Ser His Pro Glu Val Leu Pro Arg Asp Lys Tyr Gly
            100                 105                 110

His Pro Val Asn Ala Gly Ser Arg Gln Ser Trp Ser Pro Thr Ser Pro
        115                 120                 125

Val Phe Lys Glu Tyr Ala Leu Thr Leu Cys Arg Lys Leu Ala Glu Arg
130                 135                 140

Tyr Gly Thr Asn Pro Tyr Val Thr Ala Trp His Met Gly Asn Glu Tyr
145                 150                 155                 160

Gly Trp Asn Asn Arg Glu Asp Tyr Ser Asp Asn Ala Leu Glu Ala Phe
                165                 170                 175

Arg Ala Trp Cys Arg Arg Lys Tyr Gly Thr Ile Asp Ala Leu Asn Gln
            180                 185                 190

Ala Trp Gly Thr Thr Phe Trp Gly Gln Glu Met Asn Gly Phe Asp Glu
        195                 200                 205

Val Leu His Pro Thr Val His Gly Arg Arg Leu Arg Trp Ser Thr Pro
210                 215                 220

Ala Arg Ser Ser Thr Phe Glu Arg Phe Gly Asn Asp Met Leu Leu Asp
225                 230                 235                 240

Phe Tyr Lys Ala Glu Arg Asp Ala Ile Ala Glu Ile Cys Pro Asp Lys
                245                 250                 255

Pro Phe Thr Thr Asn Phe Met Val Ser Thr Asp Gln Cys Cys Met Asp
            260                 265                 270

Tyr Ala Ala Trp Ala Lys Glu Val Asn Phe Val Ser Asn Asp His Tyr
        275                 280                 285

Phe His Glu Gly Glu Ser His Leu Asp Glu Leu Ala Cys Ser Asp Ala
290                 295                 300

Leu Met Asp Ser Leu Ala Leu Gly Lys Pro Trp Tyr Val Met Glu His
305                 310                 315                 320

Ser Thr Ser Ala Val Gln Trp Lys Pro Leu Asn Thr Arg Lys Arg Lys
                325                 330                 335
```

Gly Glu Thr Val Arg Asp Ser Leu Ala His Val Ala Met Gly Ala Asp
            340                 345                 350

Ala Ile Asn Phe Phe Gln Trp Arg Ala Ser Ala Phe Gly Ala Glu Ala
        355                 360                 365

Phe His Ser Ala Met Val Pro His Ala Gly Glu Asp Thr Lys Leu Phe
    370                 375                 380

Arg Gln Val Cys Glu Leu Gly Ala Ser Leu His Thr Leu Ala Asp Ala
385                 390                 395                 400

Gly Val Gln Gly Thr Glu Leu Ala His Ser Asp Thr Ala Ile Leu Phe
                405                 410                 415

Ser Ala Glu Ser Glu Trp Ala Thr Arg Ser Gln Thr Leu Pro Ser Met
            420                 425                 430

Lys Leu Asn His Trp His Asp Val Arg Asp Trp Tyr Arg Ala Phe Leu
        435                 440                 445

Asp Ala Gly Ser Arg Ala Asp Ile Val Pro Leu Ala Tyr Asp Trp Ser
    450                 455                 460

Ser Tyr Lys Thr Val Val Leu Pro Thr Val Leu Ile Leu Ser Ala Ala
465                 470                 475                 480

Asp Thr Gln Arg Leu Ala Asp Phe Ala Ala Gly Gly Arg Val Val
                485                 490                 495

Val Gly Tyr Ala Thr Gly Leu Ile Asp Glu His Phe His Thr Trp Leu
            500                 505                 510

Gly Gly Tyr Pro Gly Ala Gly Asp Gly Leu Leu Arg Ser Met Leu Gly
        515                 520                 525

Val Arg Gly Glu Glu Phe Thr Ile Leu Gly Ala Glu Ala Glu Gly Glu
    530                 535                 540

Pro Gly Glu Ile Arg Leu Ser Ser Ala Asp Ser Ala Ala Leu Asp
545                 550                 555                 560

Gly Thr Thr Thr Arg Leu Trp Gln Asn Asp Val Asn Val Thr Gly Glu
                565                 570                 575

His Ala Gln Val Leu Ala Thr Tyr Ala Gly Glu Glu Ala Asp Glu Trp
            580                 585                 590

Glu Leu Asp Gly Thr Ala Ala Val Thr Arg Asn Pro Tyr Gly Ser Gly
        595                 600                 605

Glu Ala Tyr Phe Val Gly Cys Asp Leu Asp Val Ala Asp Leu Thr Lys
    610                 615                 620

Leu Val Arg Ala Tyr Leu Ala Ala Ser Ser Gln Glu Asn Ala Asp Val
625                 630                 635                 640

Leu His Thr Val Arg Ala Ser Ala Asp Ala Thr Phe Asp Phe Tyr Leu
                645                 650                 655

Pro Arg Gly Lys Lys Thr Val Glu Leu Gln Gly Ile Glu Gly Glu Pro
            660                 665                 670

Val Ile Leu Phe Gln Thr Asp Arg Glu Glu Lys Pro Gly Ser Tyr Thr
        675                 680                 685

Val Arg Arg Asn Gly Val Leu Val Arg Arg
    690                 695

<210> SEQ ID NO 62
<211> LENGTH: 20
<212> TYPE: PRT
<213> ORGANISM: Artificial Sequence
<220> FEATURE:
<223> OTHER INFORMATION: beta-galactosiidase II consensus peptide

<400> SEQUENCE: 62

```
Leu Leu Thr Ala Asp Gly Arg Gly Ile Ala Phe Gly Gly Asp Tyr Asn
 1               5                  10                  15

Pro Asp Gln Trp
            20

<210> SEQ ID NO 63
<211> LENGTH: 8
<212> TYPE: PRT
<213> ORGANISM: Artificial Sequence
<220> FEATURE:
<223> OTHER INFORMATION: beta-galactosiidase II consensus peptide

<400> SEQUENCE: 63

Trp Asp Asp Asp Ile Arg Leu Met
 1               5

<210> SEQ ID NO 64
<211> LENGTH: 16
<212> TYPE: PRT
<213> ORGANISM: Artificial Sequence
<220> FEATURE:
<223> OTHER INFORMATION: beta-galactosiidase II consensus peptide

<400> SEQUENCE: 64

Gln Ala Gly Val Asn Thr Val Ala Leu Ala Ile Phe Ser Trp Asp Arg
 1               5                  10                  15

<210> SEQ ID NO 65
<211> LENGTH: 5
<212> TYPE: PRT
<213> ORGANISM: Artificial Sequence
<220> FEATURE:
<223> OTHER INFORMATION: beta-galactosiidase II consensus peptide

<400> SEQUENCE: 65

Gln Pro Thr Glu Asp
 1               5

<210> SEQ ID NO 66
<211> LENGTH: 10
<212> TYPE: PRT
<213> ORGANISM: Artificial Sequence
<220> FEATURE:
<223> OTHER INFORMATION: beta-galactosiidase II consensus peptide

<400> SEQUENCE: 66

Trp Leu Asp Arg Ile Ile Asp Lys Leu Gly
 1               5                  10

<210> SEQ ID NO 67
<211> LENGTH: 16
<212> TYPE: PRT
<213> ORGANISM: Artificial Sequence
<220> FEATURE:
<223> OTHER INFORMATION: beta-galactosiidase II consensus peptide

<400> SEQUENCE: 67

Val Asp Leu Ala Ser Ala Thr Ala Thr Ala Pro Leu Trp Leu Tyr Glu
 1               5                  10                  15

<210> SEQ ID NO 68
<211> LENGTH: 64
<212> TYPE: PRT
<213> ORGANISM: Artificial Sequence
<220> FEATURE:
<223> OTHER INFORMATION: beta-galactosiidase II consensus peptide

<400> SEQUENCE: 68
```

```
His Pro Glu Val Leu Pro Arg Asp Lys Tyr Gly His Pro Val Asn Ala
1               5                   10                  15

Gly Ser Arg Gln Ser Trp Ser Pro Thr Ser Pro Val Phe Lys Glu Tyr
            20                  25                  30

Ala Leu Thr Leu Cys Arg Lys Leu Ala Glu Arg Tyr Gly Thr Asn Pro
            35                  40                  45

Tyr Val Thr Ala Trp His Met Gly Asn Glu Tyr Gly Trp Asn Asn Arg
    50                  55                  60
```

<210> SEQ ID NO 69
<211> LENGTH: 37
<212> TYPE: PRT
<213> ORGANISM: Artificial Sequence
<220> FEATURE:
<223> OTHER INFORMATION: beta-galactosiidase II consensus peptide

<400> SEQUENCE: 69

```
Asp Tyr Ser Asp Asn Ala Leu Glu Ala Phe Arg Ala Trp Cys Arg Arg
1               5                   10                  15

Lys Tyr Gly Thr Ile Asp Ala Leu Asn Gln Ala Trp Gly Thr Thr Phe
            20                  25                  30

Trp Gly Gln Glu Met
        35
```

<210> SEQ ID NO 70
<211> LENGTH: 6
<212> TYPE: PRT
<213> ORGANISM: Artificial Sequence
<220> FEATURE:
<223> OTHER INFORMATION: beta-galactosiidase II consensus peptide

<400> SEQUENCE: 70

```
Gly Phe Asp Glu Val Leu
1               5
```

<210> SEQ ID NO 71
<211> LENGTH: 34
<212> TYPE: PRT
<213> ORGANISM: Artificial Sequence
<220> FEATURE:
<223> OTHER INFORMATION: beta-galactosiidase II consensus peptide

<400> SEQUENCE: 71

```
Phe Glu Arg Phe Gly Asn Asp Met Leu Leu Asp Phe Tyr Lys Ala Glu
1               5                   10                  15

Arg Asp Ala Ile Ala Glu Ile Cys Pro Asp Lys Pro Phe Thr Thr Asn
            20                  25                  30

Phe Met
```

<210> SEQ ID NO 72
<211> LENGTH: 13
<212> TYPE: PRT
<213> ORGANISM: Artificial Sequence
<220> FEATURE:
<223> OTHER INFORMATION: beta-galactosiidase II consensus peptide

<400> SEQUENCE: 72

```
Ser Thr Asp Gln Cys Cys Met Asp Tyr Ala Ala Trp Ala
1               5                   10
```

<210> SEQ ID NO 73
<211> LENGTH: 27
<212> TYPE: PRT

```
<213> ORGANISM: Artificial Sequence
<220> FEATURE:
<223> OTHER INFORMATION: beta-galactosiidase II consensus peptide

<400> SEQUENCE: 73

Glu Val Asn Phe Val Ser Asn Asp His Tyr Phe His Glu Gly Glu Ser
 1               5                  10                  15

His Leu Asp Glu Leu Ala Cys Ser Asp Ala Leu
            20                  25

<210> SEQ ID NO 74
<211> LENGTH: 29
<212> TYPE: PRT
<213> ORGANISM: Artificial Sequence
<220> FEATURE:
<223> OTHER INFORMATION: beta-galactosiidase II consensus peptide

<400> SEQUENCE: 74

Asp Ser Leu Ala Leu Gly Lys Pro Trp Tyr Val Met Glu His Ser Thr
 1               5                  10                  15

Ser Ala Val Gln Trp Lys Pro Leu Asn Thr Arg Lys Arg
            20                  25

<210> SEQ ID NO 75
<211> LENGTH: 43
<212> TYPE: PRT
<213> ORGANISM: Artificial Sequence
<220> FEATURE:
<223> OTHER INFORMATION: beta-galactosiidase II consensus peptide

<400> SEQUENCE: 75

Gly Glu Thr Val Arg Asp Ser Leu Ala His Val Ala Met Gly Ala Asp
 1               5                  10                  15

Ala Ile Asn Phe Phe Gln Trp Arg Ala Ser Ala Phe Gly Ala Glu Ala
            20                  25                  30

Phe His Ser Ala Met Val Pro His Ala Gly Glu
        35                  40

<210> SEQ ID NO 76
<211> LENGTH: 12
<212> TYPE: PRT
<213> ORGANISM: Artificial Sequence
<220> FEATURE:
<223> OTHER INFORMATION: beta-galactosiidase II consensus peptide

<400> SEQUENCE: 76

Thr Lys Leu Phe Arg Gln Val Cys Glu Leu Gly Ala
 1               5                  10

<210> SEQ ID NO 77
<211> LENGTH: 8
<212> TYPE: PRT
<213> ORGANISM: Artificial Sequence
<220> FEATURE:
<223> OTHER INFORMATION: beta-galactosiidase II consensus peptide

<400> SEQUENCE: 77

Leu Ala Asp Ala Gly Val Gln Gly
 1               5

<210> SEQ ID NO 78
<211> LENGTH: 4
<212> TYPE: PRT
<213> ORGANISM: Artificial Sequence
<220> FEATURE:
<223> OTHER INFORMATION: beta-galactosiidase II consensus peptide
```

```
<400> SEQUENCE: 78

Glu Leu Ala His
1

<210> SEQ ID NO 79
<211> LENGTH: 16
<212> TYPE: PRT
<213> ORGANISM: Artificial Sequence
<220> FEATURE:
<223> OTHER INFORMATION: beta-galactosiidase II consensus peptide

<400> SEQUENCE: 79

Asp Thr Ala Ile Leu Phe Ser Ala Glu Ser Glu Trp Ala Thr Arg Ser
1               5                   10                  15

<210> SEQ ID NO 80
<211> LENGTH: 21
<212> TYPE: PRT
<213> ORGANISM: Artificial Sequence
<220> FEATURE:
<223> OTHER INFORMATION: beta-galactosiidase II consensus peptide

<400> SEQUENCE: 80

Thr Leu Pro Ser Met Lys Leu Asn His Trp His Asp Val Arg Asp Trp
1               5                   10                  15

Tyr Arg Ala Phe Leu
            20

<210> SEQ ID NO 81
<211> LENGTH: 16
<212> TYPE: PRT
<213> ORGANISM: Artificial Sequence
<220> FEATURE:
<223> OTHER INFORMATION: beta-galactosiidase II consensus peptide

<400> SEQUENCE: 81

Arg Ala Asp Ile Val Pro Leu Ala Tyr Asp Trp Ser Ser Tyr Lys Thr
1               5                   10                  15

<210> SEQ ID NO 82
<211> LENGTH: 6
<212> TYPE: PRT
<213> ORGANISM: Artificial Sequence
<220> FEATURE:
<223> OTHER INFORMATION: beta-galactosiidase II consensus peptide

<400> SEQUENCE: 82

Val Leu Pro Thr Val Leu
1               5

<210> SEQ ID NO 83
<211> LENGTH: 12
<212> TYPE: PRT
<213> ORGANISM: Artificial Sequence
<220> FEATURE:
<223> OTHER INFORMATION: beta-galactosiidase II consensus peptide

<400> SEQUENCE: 83

Gly Gly Arg Val Val Val Gly Tyr Ala Thr Gly Leu
1               5                   10

<210> SEQ ID NO 84
<211> LENGTH: 27
<212> TYPE: PRT
<213> ORGANISM: Artificial Sequence
<220> FEATURE:
```

```
<223> OTHER INFORMATION: beta-galactosiidase II consensus peptide

<400> SEQUENCE: 84

Phe His Thr Trp Leu Gly Gly Tyr Pro Gly Ala Gly Asp Gly Leu Leu
1               5                   10                  15

Arg Ser Met Leu Gly Val Arg Gly Glu Glu Phe
            20                  25

<210> SEQ ID NO 85
<211> LENGTH: 4
<212> TYPE: PRT
<213> ORGANISM: Artificial Sequence
<220> FEATURE:
<223> OTHER INFORMATION: beta-galactosiidase II consensus peptide

<400> SEQUENCE: 85

Glu Ile Arg Leu
1

<210> SEQ ID NO 86
<211> LENGTH: 8
<212> TYPE: PRT
<213> ORGANISM: Artificial Sequence
<220> FEATURE:
<223> OTHER INFORMATION: beta-galactosiidase II consensus peptide

<400> SEQUENCE: 86

Thr Arg Leu Trp Gln Asn Asp Val
1               5

<210> SEQ ID NO 87
<211> LENGTH: 4
<212> TYPE: PRT
<213> ORGANISM: Artificial Sequence
<220> FEATURE:
<223> OTHER INFORMATION: beta-galactosiidase II consensus peptide

<400> SEQUENCE: 87

Gln Val Leu Ala
1

<210> SEQ ID NO 88
<211> LENGTH: 6
<212> TYPE: PRT
<213> ORGANISM: Artificial Sequence
<220> FEATURE:
<223> OTHER INFORMATION: beta-galactosiidase II consensus peptide

<400> SEQUENCE: 88

Tyr Ala Gly Glu Glu Ala
1               5

<210> SEQ ID NO 89
<211> LENGTH: 9
<212> TYPE: PRT
<213> ORGANISM: Artificial Sequence
<220> FEATURE:
<223> OTHER INFORMATION: beta-galactosiidase II consensus peptide

<400> SEQUENCE: 89

Glu Trp Glu Leu Asp Gly Thr Ala Ala
1               5

<210> SEQ ID NO 90
<211> LENGTH: 5
<212> TYPE: PRT
<213> ORGANISM: Artificial Sequence
```

-continued

```
<220> FEATURE:
<223> OTHER INFORMATION: beta-galactosiidase II consensus peptide

<400> SEQUENCE: 90

Gly Glu Ala Tyr Phe
  1               5

<210> SEQ ID NO 91
<211> LENGTH: 4
<212> TYPE: PRT
<213> ORGANISM: Artificial Sequence
<220> FEATURE:
<223> OTHER INFORMATION: beta-galactosiidase II consensus peptide

<400> SEQUENCE: 91

Gly Cys Asp Leu
  1

<210> SEQ ID NO 92
<211> LENGTH: 7
<212> TYPE: PRT
<213> ORGANISM: Artificial Sequence
<220> FEATURE:
<223> OTHER INFORMATION: beta-galactosiidase II consensus peptide

<400> SEQUENCE: 92

Asp Val Leu His Thr Val Arg
  1               5

<210> SEQ ID NO 93
<211> LENGTH: 5
<212> TYPE: PRT
<213> ORGANISM: Artificial Sequence
<220> FEATURE:
<223> OTHER INFORMATION: beta-galactosiidase II consensus peptide

<400> SEQUENCE: 93

Phe Asp Phe Tyr Leu
  1               5

<210> SEQ ID NO 94
<211> LENGTH: 6
<212> TYPE: PRT
<213> ORGANISM: Artificial Sequence
<220> FEATURE:
<223> OTHER INFORMATION: beta-galactosiidase II consensus peptide

<400> SEQUENCE: 94

Arg Asn Gly Val Leu Val
  1               5

<210> SEQ ID NO 95
<211> LENGTH: 215
<212> TYPE: PRT
<213> ORGANISM: Bifidobacterium longum
<220> FEATURE:
<223> OTHER INFORMATION: N-acetylmannosamine-6-phosphate 2-epimerase II,
      contig 30, gene 1561 translation positions 7-221

<400> SEQUENCE: 95

Val Ile Glu Arg Val Lys Gly Gly Leu Ile Val Ser Cys Gln Ala Tyr
  1               5                  10                  15

Pro Gly Glu Pro Leu Arg His Pro Glu Thr Met Ala Gln Met Ala Met
                 20                  25                  30

Ala Ala Val Glu Gly Gly Ala Val Gly Ile Arg Cys Gln Gly Leu Ala
             35                  40                  45
```

```
Asp Ile Ala Ala Ile Lys Gly Gln Val Asp Val Pro Val Ile Gly Ile
        50                  55                  60

Trp Lys Asp Gly Ser Gln Gly Val Tyr Ile Thr Pro Thr Leu Arg His
 65                  70                  75                  80

Ala Arg Cys Cys Ala Ala Gly Ala Asp Ile Val Ala Leu Asp Ala
                 85                  90                  95

Thr Gly Arg Pro Arg Pro Asp Gly Arg Thr Tyr Ala Gln Thr Val Gln
                100                 105                 110

Ala Leu His Asp Glu Gly Val Thr Val Met Ala Asp Cys Gly Ser Phe
            115                 120                 125

Asp Asp Ala Arg Arg Ala Val Asp Ala Gly Ser Asp Ile Ile Ser Thr
        130                 135                 140

Thr Leu Ser Gly Tyr Thr Gly Glu Arg Glu Lys Thr Asp Gly Pro Asp
145                 150                 155                 160

Leu Glu Leu Leu Glu Tyr Met Val Ser Ser Phe Pro Asp Thr Pro Val
                165                 170                 175

Leu Cys Glu Gly Arg Ile His Thr Pro Glu Gln Leu His Asp Val Met
                180                 185                 190

Ser Arg Gly Ala Trp Ala Ala Val Val Gly Thr Ala Ile Thr His Pro
            195                 200                 205

Thr Ser Ile Thr Arg Trp Phe
    210                 215

<210> SEQ ID NO 96
<211> LENGTH: 217
<212> TYPE: PRT
<213> ORGANISM: Propionibacterium acnes
<220> FEATURE:
<223> OTHER INFORMATION: N-acetylmannosamine-6-phosphate 2-epimerase
      (ManNAc-6-P epimerase, nanE), locus PPA1997,
      positions 8-224

<400> SEQUENCE: 96

Ile Ile Ala Ser Met Ala Gly Gly Leu Val Val Ser Cys Gln Ala Tyr
 1               5                  10                  15

Pro Gly Glu Pro Leu Arg His Pro Glu Thr Met Ala Gln Met Ala Ala
                20                  25                  30

Ala Val Glu Ala Gly Gly Ala Val Ala Val Arg Ala Gln Gly Leu Ser
            35                  40                  45

Asp Val Ser Ala Val Lys Gly Arg Val Ser Val Pro Val Val Gly Ile
        50                  55                  60

Trp Lys Glu Gly Asp Glu Gly Ile Tyr Ile Thr Pro Thr Leu Arg His
 65                  70                  75                  80

Ala Arg Cys Val Ser Ala Ala Gly Ala Asp Val Val Ala Leu Asp Gly
                 85                  90                  95

Thr Arg Arg Glu Arg Ala Asp Gly Leu Ser Leu Ala Glu Thr Ile Glu
                100                 105                 110

Arg Leu Lys Arg Glu Tyr Asp Val Val Met Ala Asp Cys Gly Ser
            115                 120                 125

Val Asp Asp Gly Leu Phe Ala Ala Glu Ala Gly Ala Asp Leu Ile Gly
        130                 135                 140

Thr Thr Leu Cys Gly Tyr Thr Gly Glu Arg Pro Lys Thr Asp Gly Pro
145                 150                 155                 160

Asp Tyr Glu Val Ile Glu Ala Leu Val Lys Lys Leu Asp Gly Asp Arg
                165                 170                 175

Pro Val Ile Ala Glu Gly Arg Ile His Thr Pro Asp Gln Ala Arg Arg
                180                 185                 190
```

```
Ala Met Asp Leu Gly Ala His Ala Val Val Val Gly Thr Ala Ile Thr
        195                 200                 205

His Pro Thr Ser Ile Thr Gly Trp Phe
    210                 215

<210> SEQ ID NO 97
<211> LENGTH: 21
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 97

Val Ser Cys Gln Ala Tyr Pro Gly Glu Pro Leu Arg His Pro Glu Thr
1               5                   10                  15

Met Ala Gln Met Ala
            20

<210> SEQ ID NO 98
<211> LENGTH: 4
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 98

Gly Gly Ala Val
1

<210> SEQ ID NO 99
<211> LENGTH: 4
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 99

Gly Ile Trp Lys
1

<210> SEQ ID NO 100
<211> LENGTH: 11
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 100

Tyr Ile Thr Pro Thr Leu Arg His Ala Arg Cys
1               5                   10

<210> SEQ ID NO 101
<211> LENGTH: 5
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 101

Ala Ala Gly Ala Asp
1               5
```

```
<210> SEQ ID NO 102
<211> LENGTH: 4
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 102

Val Ala Leu Asp
1

<210> SEQ ID NO 103
<211> LENGTH: 7
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 103

Val Met Ala Asp Cys Gly Ser
1               5

<210> SEQ ID NO 104
<211> LENGTH: 6
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 104

Gly Tyr Thr Gly Glu Arg
1               5

<210> SEQ ID NO 105
<211> LENGTH: 6
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 105

Lys Thr Asp Gly Pro Asp
1               5

<210> SEQ ID NO 106
<211> LENGTH: 7
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 106

Glu Gly Arg Ile His Thr Pro
1               5

<210> SEQ ID NO 107
<211> LENGTH: 13
<212> TYPE: PRT
<213> ORGANISM: Artificial Sequence
<220> FEATURE:
<223> OTHER INFORMATION: N-acetylmannosamine-6-phosphate 2-epimerase II
      consensus peptide

<400> SEQUENCE: 107
```

Val Val Gly Thr Ala Ile Thr His Pro Thr Ser Ile Thr
1               5                   10

<210> SEQ ID NO 108
<211> LENGTH: 301
<212> TYPE: PRT
<213> ORGANISM: Bifidobacterium longum
<220> FEATURE:
<223> OTHER INFORMATION: N-acetylneuraminate lyase I, contig 15, gene
      498 translation

<400> SEQUENCE: 108

Met Ser Glu His Asp Met His Leu Leu Glu Pro Ala Pro Phe Gly Arg
1               5                   10                  15

Ile Leu Pro Ala Met Val Thr Pro Met Lys Ser Asp Gly Ser Val Asp
                20                  25                  30

Phe Ala Ala Ala Gln Lys Leu Ala Lys Tyr Leu Val Ala Asp Gly Ala
            35                  40                  45

Asp Gly Leu Val Val Asn Gly Thr Thr Gly Glu Ser Pro Val Thr His
        50                  55                  60

Met Asp Glu Lys Val Glu Leu Val Arg Ala Val Lys Glu Val Val Asp
65                  70                  75                  80

Val Pro Val Ile Ser Gly Ala Gly Ser Asn Asp Thr Ala His Thr Val
                85                  90                  95

Arg Met Val Glu Gln Thr Gln Glu Ala Gly Ala Asp Ala Val Leu Val
            100                 105                 110

Val Met Pro Tyr Tyr Ser Arg Pro Ser Gln Asp Gly Ile Val Gly His
        115                 120                 125

Tyr Lys Ala Val Asp Glu Ser Ala Glu Lys Pro Ile Ile Val Tyr Asp
130                 135                 140

Val Pro Gly Arg Thr Gly Leu Lys Val Lys Val Glu Thr Tyr Asp Arg
145                 150                 155                 160

Leu Ala Gly Leu Glu His Val Lys Ala Val Lys Asp Ala Thr Gly Asp
                165                 170                 175

Leu Ala Ala Ala Val Glu Lys Gln Gln Arg Thr Gly Leu Ala Trp Tyr
            180                 185                 190

Ser Gly Asp Asp Gly Leu Phe Leu Pro Phe Leu Ser Ile Gly Ala Val
        195                 200                 205

Gly Ile Ile Ser Val Ile Ala His Val Ala Ser Asn Pro Met Gln Gln
    210                 215                 220

Leu Val Gln Ala Phe Asp Arg Gly Asp Ile Thr Thr Ala Arg Arg Leu
225                 230                 235                 240

Ala Asn Gln Leu Ala Pro Leu Val His Ala Leu Asn Gly Asp Gly Tyr
                245                 250                 255

Gln Ala Val Met Ala Lys Ala Leu Lys Val Lys Gly Val Ile Pro
            260                 265                 270

Ser Thr Thr Met Arg Leu Pro Asn Ile Gly Pro Asp Ala Thr Gln Leu
        275                 280                 285

Asp Lys Ala Glu Glu Gly Met Arg Ala Ala Gly Leu Leu
    290                 295                 300

<210> SEQ ID NO 109
<211> LENGTH: 301
<212> TYPE: PRT
<213> ORGANISM: Bifidobacterium longum
<220> FEATURE:
<223> OTHER INFORMATION: dihydrodipicolinate synthase (DHDPS, dapA,
      DhdPS, COG family), N-acetylneuraminate lyase, locus BL1193

<400> SEQUENCE: 109

Met Ser Glu His Asp Met His Leu Leu Asp Ser Ala Pro Phe Gly Arg
1               5                   10                  15

Ile Leu Pro Ala Met Val Thr Pro Met Lys Ser Asp Gly Ser Val Asp
            20                  25                  30

Phe Ala Ala Ala Gln Lys Leu Ala Lys Tyr Leu Val Ala Asp Gly Ala
        35                  40                  45

Asp Gly Leu Val Val Asn Gly Thr Thr Gly Glu Ser Pro Val Thr His
    50                  55                  60

Met Asp Glu Lys Val Glu Leu Val Arg Ala Val Lys Glu Val Val Asp
65                  70                  75                  80

Val Pro Val Ile Ser Gly Ala Gly Ser Asn Asp Thr Ala His Thr Val
                85                  90                  95

Arg Met Val Glu Gln Thr Gln Glu Ala Gly Ala Asp Ala Val Leu Val
            100                 105                 110

Val Met Pro Tyr Tyr Ser Arg Pro Ser Gln Asp Gly Ile Val Gly His
        115                 120                 125

Tyr Lys Ala Val Asp Glu Ser Ala Glu Lys Pro Ile Ile Val Tyr Asp
    130                 135                 140

Val Pro Gly Arg Thr Gly Leu Lys Val Lys Val Gly Thr Tyr Asp Arg
145                 150                 155                 160

Leu Ala Glu Leu Glu His Val Lys Ala Val Lys Asp Ala Thr Gly Asp
                165                 170                 175

Leu Ala Ala Val Glu Lys Gln Gln Arg Thr Gly Leu Ala Trp Tyr
            180                 185                 190

Ser Gly Asp Asp Gly Leu Phe Leu Pro Phe Leu Ser Ile Gly Ala Val
        195                 200                 205

Gly Ile Ile Ser Val Ile Ala His Val Ala Ser Asn Pro Met Gln Gln
    210                 215                 220

Leu Val Gln Ala Phe Asp Arg Gly Asp Ile Thr Thr Ala Arg Arg Leu
225                 230                 235                 240

Ala Asn Gln Leu Ala Pro Leu Val His Ala Leu Asn Gly Asp Gly Tyr
                245                 250                 255

Gln Ala Val Met Ala Lys Ala Ala Leu Lys Val Lys Gly Val Ile Pro
            260                 265                 270

Ser Thr Thr Met Arg Leu Pro Asn Ile Gly Pro Asp Ala Thr Gln Leu
        275                 280                 285

Asp Lys Ala Glu Glu Gly Met Arg Ala Ala Gly Leu Leu
    290                 295                 300

<210> SEQ ID NO 110
<211> LENGTH: 9
<212> TYPE: PRT
<213> ORGANISM: Artificial Sequence
<220> FEATURE:
<223> OTHER INFORMATION: N-acetylneuraminate lyase I consensus peptide

<400> SEQUENCE: 110

Met Ser Glu His Asp Met His Leu Leu
1               5

<210> SEQ ID NO 111
<211> LENGTH: 144
<212> TYPE: PRT
<213> ORGANISM: Artificial Sequence
<220> FEATURE:
<223> OTHER INFORMATION: N-acetylneuraminate lyase I consensus peptide

<400> SEQUENCE: 111

```
Ala Pro Phe Gly Arg Ile Leu Pro Ala Met Val Thr Pro Met Lys Ser
 1               5                  10                  15

Asp Gly Ser Val Asp Phe Ala Ala Gln Lys Leu Ala Lys Tyr Leu
             20                  25                  30

Val Ala Asp Gly Ala Asp Gly Leu Val Val Asn Gly Thr Thr Gly Glu
         35                  40                  45

Ser Pro Val Thr His Met Asp Glu Lys Val Glu Leu Val Arg Ala Val
     50                  55                  60

Lys Glu Val Val Asp Val Pro Val Ile Ser Gly Ala Gly Ser Asn Asp
 65                  70                  75                  80

Thr Ala His Thr Val Arg Met Val Glu Gln Thr Gln Glu Ala Gly Ala
                 85                  90                  95

Asp Ala Val Leu Val Val Met Pro Tyr Tyr Ser Arg Pro Ser Gln Asp
             100                 105                 110

Gly Ile Val Gly His Tyr Lys Ala Val Asp Glu Ser Ala Glu Lys Pro
         115                 120                 125

Ile Ile Val Tyr Asp Val Pro Gly Arg Thr Gly Leu Lys Val Lys Val
     130                 135                 140
```

<210> SEQ ID NO 112
<211> LENGTH: 6
<212> TYPE: PRT
<213> ORGANISM: Artificial Sequence
<220> FEATURE:
<223> OTHER INFORMATION: N-acetylneuraminate lyase I consensus peptide

<400> SEQUENCE: 112

```
Thr Tyr Asp Arg Leu Ala
 1               5
```

<210> SEQ ID NO 113
<211> LENGTH: 138
<212> TYPE: PRT
<213> ORGANISM: Artificial Sequence
<220> FEATURE:
<223> OTHER INFORMATION: N-acetylneuraminate lyase I consensus peptide

<400> SEQUENCE: 113

```
Leu Glu His Val Lys Ala Val Lys Asp Ala Thr Gly Asp Leu Ala Ala
 1               5                  10                  15

Ala Val Glu Lys Gln Gln Arg Thr Gly Leu Ala Trp Tyr Ser Gly Asp
             20                  25                  30

Asp Gly Leu Phe Leu Pro Phe Leu Ser Ile Gly Ala Val Gly Ile Ile
         35                  40                  45

Ser Val Ile Ala His Val Ala Ser Asn Pro Met Gln Gln Leu Val Gln
     50                  55                  60

Ala Phe Asp Arg Gly Asp Ile Thr Thr Ala Arg Arg Leu Ala Asn Gln
 65                  70                  75                  80

Leu Ala Pro Leu Val His Ala Leu Asn Gly Asp Gly Tyr Gln Ala Val
                 85                  90                  95

Met Ala Lys Ala Ala Leu Lys Val Lys Gly Val Ile Pro Ser Thr Thr
             100                 105                 110

Met Arg Leu Pro Asn Ile Gly Pro Asp Ala Thr Gln Leu Asp Lys Ala
         115                 120                 125

Glu Glu Gly Met Arg Ala Ala Gly Leu Leu
     130                 135
```

<210> SEQ ID NO 114
<211> LENGTH: 301
<212> TYPE: PRT
<213> ORGANISM: Bifidobacterium longum
<220> FEATURE:
<223> OTHER INFORMATION: N-acetylneuraminate lyase III, contig 23, gene
      827 translation positions 3-303

<400> SEQUENCE: 114

Gln Phe Arg Gly Val Ile Pro Pro Val Val Thr Pro Leu Thr Ala Asp
 1               5                  10                  15

His Arg Leu Asp Val Glu Ser Tyr Arg Arg Ser Ile Asp Arg Met Ile
            20                  25                  30

Ala Ala Gly Val Asn Gly Leu Phe Val Leu Gly Ser Ser Ser Glu Val
        35                  40                  45

Val Phe Ser Thr Asp Glu Arg Arg Glu Ile Leu Ala Ala Ile
    50                  55                  60

Glu Ile Ala Gly Gly Arg Val Pro Val Leu Ala Gly Cys Ile Asp Thr
65                  70                  75                  80

Glu Thr Asn Arg Val Ile Glu His Ala Arg Ala Ala Arg Glu Met Gly
                85                  90                  95

Ala Ala Ala Ile Val Ala Thr Ala Pro Phe Tyr Ala Leu Gly Gly Val
            100                 105                 110

Ala Glu Ile Glu Arg His Phe Arg Leu Ile His Ala Ala Val Pro Glu
        115                 120                 125

Leu Pro Leu Phe Ala Tyr Asp Ile Pro Val Cys Val His Thr Lys Leu
    130                 135                 140

Pro Asn Asp Leu Leu Ile Arg Leu Gly Arg Asp Gly Val Leu Ala Gly
145                 150                 155                 160

Val Lys Asp Ser Ser Asn Asp Val Ala Phe Arg Phe Leu Ile Gly
                165                 170                 175

Asp Asn Glu Glu Asn Gly His Pro Leu Thr Leu Leu Thr Gly Gln Glu
            180                 185                 190

Val Val Val Asp Gly Ala Tyr Met Ala Gly Ala Asp Gly Ser Val Pro
        195                 200                 205

Gly Leu Ala Asn Val Asp Pro Tyr Gly Tyr Val Ala Met Trp Asn Ala
    210                 215                 220

Tyr Arg Asn Gly Asp Trp Asp Ser Val Arg Lys Glu Gln Asn Lys Leu
225                 230                 235                 240

Ala Ala Leu Met Arg Ile Val Leu Ala Pro Ser Gly Val Gln Gly Phe
                245                 250                 255

Gly Ser Gly Val Gly Ala Phe Lys Thr Ala Met Ala Leu Leu Gly Val
            260                 265                 270

Phe Asp Thr Asn Gln Met Pro Glu Pro Val Leu Ala Leu His Gly Asp
        275                 280                 285

Asn Val Lys Ala Ile Ala Asp Val Leu Arg Ala Cys Gly
    290                 295                 300

<210> SEQ ID NO 115
<211> LENGTH: 300
<212> TYPE: PRT
<213> ORGANISM: Bifidobacterium longum
<220> FEATURE:
<223> OTHER INFORMATION: dihydrodipicolinate synthase, locus PPA1998,
      positions 4-303

<400> SEQUENCE: 115

Lys Phe His Gly Val Ile Pro Pro Val Val Thr Pro Leu Thr Pro Asn

-continued

```
                1               5                  10                 15
Gly Asp Leu Asp Val Ala Ser Tyr Glu Lys Leu Ile Asn Arg Leu Ile
                20                  25                  30

Gly Gln Gly Val Asp Gly Leu Phe Val Leu Gly Ser Thr Ser Glu Val
                35                  40                  45

Ala Phe Phe Asp Asp Glu Met Arg Gly Arg Val Leu Ser Glu Ala Lys
                50                  55                  60

Arg Ile Ile Asp Gly Arg Val Pro Leu Leu Ala Gly Val Ile Asp Thr
65                  70                  75                  80

Glu Thr Leu Arg Val Ile Arg His Ile Gly Gln Ala Glu Glu Ile Gly
                85                  90                  95

Val Asp Ala Val Val Ala Thr Ala Pro Phe Tyr Ala Ile Thr Gly Pro
                100                 105                 110

Thr Glu Ile Glu Asn His Phe Arg Ala Leu His Glu Ala Thr Asp Leu
                115                 120                 125

Pro Leu Phe Val Tyr Asp Ile Pro Val Cys Val His Val Lys Val Pro
                130                 135                 140

Val Asp Leu Met Met Lys Leu Gly Arg Glu Gly Val Ile Ala Gly Cys
145                 150                 155                 160

Lys Asp Ser Ser Ala Asp Asp Val Ser Phe Arg Leu Ala Leu Ala
                165                 170                 175

Asn Arg Ala Ala Gly Ser Pro Leu Ser Leu Phe Thr Gly His Glu Val
                180                 185                 190

Val Val Asp Gly Ala Phe Met Ser Gly Ala Asp Gly Val Val Pro Gly
                195                 200                 205

Leu Ala Asn Val Asp Ala Thr Ser Tyr Val Ala Met Tyr Lys Ala Tyr
                210                 215                 220

Arg Glu Gly Asp Trp Glu Thr Val Arg Ile Glu Gln Asp Lys Ala Ala
225                 230                 235                 240

Glu Leu Met Glu Ile Ala Phe Ala Pro Gln Gly Val Val Gly Pro Ala
                245                 250                 255

Ala Gly Val Gly Ala Phe Lys Thr Ala Met Gln Leu Leu Gly Ile Ile
                260                 265                 270

Glu Thr Asn Thr Met Ser Val Pro Leu Pro Thr Leu Thr Gly Asp Asn
                275                 280                 285

Val Glu Arg Val Ala Glu Val Leu Arg Arg Val Gly
                290                 295                 300

<210> SEQ ID NO 116
<211> LENGTH: 11
<212> TYPE: PRT
<213> ORGANISM: Artificial Sequence
<220> FEATURE:
<223> OTHER INFORMATION: N-acetylneuraminate lyase III consensus peptide

<400> SEQUENCE: 116

Gly Val Ile Pro Pro Val Val Thr Pro Leu Thr
1               5                   10

<210> SEQ ID NO 117
<211> LENGTH: 7
<212> TYPE: PRT
<213> ORGANISM: Artificial Sequence
<220> FEATURE:
<223> OTHER INFORMATION: N-acetylneuraminate lyase III consensus peptide

<400> SEQUENCE: 117

Gly Leu Phe Val Leu Gly Ser
```

```
<210> SEQ ID NO 118
<211> LENGTH: 4
<212> TYPE: PRT
<213> ORGANISM: Artificial Sequence
<220> FEATURE:
<223> OTHER INFORMATION: N-acetylneuraminate lyase III consensus peptide

<400> SEQUENCE: 118

Gly Arg Val Pro
1

<210> SEQ ID NO 119
<211> LENGTH: 5
<212> TYPE: PRT
<213> ORGANISM: Artificial Sequence
<220> FEATURE:
<223> OTHER INFORMATION: N-acetylneuraminate lyase III consensus peptide

<400> SEQUENCE: 119

Ile Asp Thr Glu Thr
1               5

<210> SEQ ID NO 120
<211> LENGTH: 8
<212> TYPE: PRT
<213> ORGANISM: Artificial Sequence
<220> FEATURE:
<223> OTHER INFORMATION: N-acetylneuraminate lyase III consensus peptide

<400> SEQUENCE: 120

Val Ala Thr Ala Pro Phe Tyr Ala
1               5

<210> SEQ ID NO 121
<211> LENGTH: 4
<212> TYPE: PRT
<213> ORGANISM: Artificial Sequence
<220> FEATURE:
<223> OTHER INFORMATION: N-acetylneuraminate lyase III consensus peptide

<400> SEQUENCE: 121

Leu Pro Leu Phe
1

<210> SEQ ID NO 122
<211> LENGTH: 8
<212> TYPE: PRT
<213> ORGANISM: Artificial Sequence
<220> FEATURE:
<223> OTHER INFORMATION: N-acetylneuraminate lyase III consensus peptide

<400> SEQUENCE: 122

Tyr Asp Ile Pro Val Cys Val His
1               5

<210> SEQ ID NO 123
<211> LENGTH: 4
<212> TYPE: PRT
<213> ORGANISM: Artificial Sequence
<220> FEATURE:
<223> OTHER INFORMATION: N-acetylneuraminate lyase III consensus peptide

<400> SEQUENCE: 123

Lys Asp Ser Ser
1
```

```
<210> SEQ ID NO 124
<211> LENGTH: 7
<212> TYPE: PRT
<213> ORGANISM: Artificial Sequence
<220> FEATURE:
<223> OTHER INFORMATION: N-acetylneuraminate lyase III consensus peptide

<400> SEQUENCE: 124

Glu Val Val Val Asp Gly Ala
 1               5

<210> SEQ ID NO 125
<211> LENGTH: 4
<212> TYPE: PRT
<213> ORGANISM: Artificial Sequence
<220> FEATURE:
<223> OTHER INFORMATION: N-acetylneuraminate lyase III consensus peptide

<400> SEQUENCE: 125

Gly Ala Asp Gly
 1

<210> SEQ ID NO 126
<211> LENGTH: 8
<212> TYPE: PRT
<213> ORGANISM: Artificial Sequence
<220> FEATURE:
<223> OTHER INFORMATION: N-acetylneuraminate lyase III consensus peptide

<400> SEQUENCE: 126

Val Pro Gly Leu Ala Asn Val Asp
 1               5

<210> SEQ ID NO 127
<211> LENGTH: 4
<212> TYPE: PRT
<213> ORGANISM: Artificial Sequence
<220> FEATURE:
<223> OTHER INFORMATION: N-acetylneuraminate lyase III consensus peptide

<400> SEQUENCE: 127

Tyr Val Ala Met
 1

<210> SEQ ID NO 128
<211> LENGTH: 9
<212> TYPE: PRT
<213> ORGANISM: Artificial Sequence
<220> FEATURE:
<223> OTHER INFORMATION: N-acetylneuraminate lyase III consensus peptide

<400> SEQUENCE: 128

Gly Val Gly Ala Phe Lys Thr Ala Met
 1               5

<210> SEQ ID NO 129
<211> LENGTH: 4
<212> TYPE: PRT
<213> ORGANISM: Artificial Sequence
<220> FEATURE:
<223> OTHER INFORMATION: N-acetylneuraminate lyase III consensus peptide

<400> SEQUENCE: 129

Gly Asp Asn Val
 1
```